(12) United States Patent
Ellis et al.

(10) Patent No.: US 12,723,255 B2
(45) **Date of Patent: *Sep. 1, 2026**

(54) HERBICIDE TOLERANCE GENES AND METHODS OF USE THEREOF

(71) Applicant: Monsanto Technology LLC, St. Louis, MO (US)

(72) Inventors: Christine M. Ellis, Manchester, MO (US); Artem G. Evdokimov, Orchard Park, NY (US); Paul C.C. Feng, Creve Coeur, MO (US); Xiaoran Fu, Belmont, MA (US); Clayton T. Larue, Chesterfield, MO (US); Jeffrey R. Nageotte, Billerica, MA (US); Andrew C. Read, Ithaca, NY (US); Lei Shi, San Diego, CA (US); Andrew W. Wollacott, Boston, MA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/753,627

(22) Filed: Jun. 25, 2024

(65) Prior Publication Data

US 2024/0409952 A1 Dec. 12, 2024

Related U.S. Application Data

(63) Continuation of application No. 18/301,106, filed on Apr. 14, 2023, now Pat. No. 12,049,636, which is a (Continued)

(51) Int. Cl.

*C12N 15/82* (2006.01)
*A01H 5/10* (2018.01)

(Continued)

(52) U.S. Cl.

CPC .......... *C12N 15/8274* (2013.01); *A01H 5/10* (2013.01); *A01N 57/00* (2013.01); *A01N 63/10* (2020.01);

(Continued)

(58) Field of Classification Search

None

See application file for complete search history.

(56) References Cited

U.S. PATENT DOCUMENTS 6,153,401 A 11/2000 Streber et al.
7,838,733 B2 * 11/2010 Wright ................ C12N 9/0069 800/300

(Continued)

FOREIGN PATENT DOCUMENTS

ES 2528914 2/2015
WO 2005107437 11/2005

(Continued)

OTHER PUBLICATIONS

GenBank Accession No. AF516752, dated Sep. 7, 2004.

(Continued)

*Primary Examiner* — Weihua Fan

(74) *Attorney, Agent, or Firm* — Dentons US LLP; Elizabeth Millard

(57) ABSTRACT

Polypeptides and recombinant DNA molecules useful for conferring tolerance to AOPP herbicides, phenoxy acid herbicides, and pyridinyloxy acid herbicides are provided in the present invention, as well as herbicide tolerant transgenic plants, seeds, cells, and plant parts containing the recombinant DNA molecules, as well as methods of using the same.

6 Claims, 11 Drawing Sheets

Specification includes a Sequence Listing.

Untreated Quizalofop Untreated Quizalofop

LH244 SEQ ID NO:11

Related U.S. Application Data continuation of application No. 17/150,604, filed on Jan. 15, 2021, now Pat. No. 11,655,480, which is a continuation of application No. 16/016,364, filed on Jun. 22, 2018, now Pat. No. 10,900,050, which is a continuation of application No. 14/871,768, filed on Sep. 30, 2015, now Pat. No. 10,023,874.

(60) Provisional application No. 62/064,343, filed on Oct. 15, 2014.

(51) Int. Cl.

| | |
|---|---|
| ***A01N 57/00*** | (2006.01) |
| ***A01N 63/10*** | (2020.01) |
| ***C07K 14/195*** | (2006.01) |
| ***C12N 9/02*** | (2006.01) |

(52) U.S. Cl.

CPC .......... *C07K 14/195* (2013.01); *C12N 9/0071* (2013.01); *C12Y 113/00* (2013.01); *C07K 2319/08* (2013.01); *C12Y 114/11033* (2013.01)

(56) References Cited

U.S. PATENT DOCUMENTS

| | | | |
|---|---|---|---|
| 8,598,413 | B2 | 12/2013 | Cui et al. |
| 8,748,700 | B2 | 6/2014 | Hanger et al. |
| 9,127,289 | B2 | 9/2015 | Wright et al. |
| 10,023,874 | B2 | 7/2018 | Ellis et al. |
| 2003/0041357 | A1 | 2/2003 | Jepson et al. |
| 2006/0150270 | A1 | 7/2006 | Hammer et al. |
| 2009/0093366 | A1 | 4/2009 | Wright et al. |
| 2012/0042412 | A1 | 2/2012 | Albert et al. |
| 2012/0222153 | A1 | 8/2012 | Cui et al. |
| 2013/0219552 | A1 | 8/2013 | Lira et al. |
| 2014/0256548 | A1 | 9/2014 | Braxton et al. |
| 2015/0344903 | A1 | 12/2015 | Wright et al. |

FOREIGN PATENT DOCUMENTS

| | | |
|---|---|---|
| WO | 2007053482 | 5/2007 |
| WO | 2011022469 | 2/2011 |
| WO | 2011022470 | 2/2011 |
| WO | 2012115968 | 8/2012 |
| WO | 2012142371 | 10/2012 |

OTHER PUBLICATIONS

GenBank Accession No. AJ628859, dated Apr. 15, 2005.

Kohler, "Sphingobium herbicidovorans MH: a versatile phenoxyalkanoic acid herbicide degrader," J. Industrial Microbiology & Biotechnology 23:336-340, 1999.

Müller et al., "Genetic analysis of phenoxyalkanoic acid degradation in Sphingomonas herbicidovorans MH," Applied Environmental Microbiology 70(10):6066-75, 2004.

Müller et al., "Purification and characterization of two enantioselective alpha-Ketoglutarate-Dependent Dioxygenases, RdPA and SdpA, from Sphingomonas herbicidovorans MH," Applied and Environmental Microbiology 72(7):4853-4861, 2006.

Müller et al., "Structural basis for the enantiospecificities of R- and S-specific phenoxypropionate/alpha-ketoglutarate dioxygenases," Protein Science 15(6):1356-68, 2006.

Nickel et al., "Involvement of two α-ketoglutarate-dependent dioxygenases in enantioselective Degradation of (R)- and (S)-Mecoprop by Sphingobium herbiciovorans MH," Journal of Bacteriology 179(21):6674-6679, 1997.

Schleinitz et al., "Localization and characterization of two novel genes encoding stereospecific dioxygenases catalyzing 2(2,4-dichlorophenoxy)propionate cleavage in Delftia acidovorans MC1," Applied and Environmental Microbiology 70(9):5357-5365, 2004.

UniProtKB/Swiss-Prot Accession No. Q8KSC8, dated Nov. 11, 2015.

Westendorf et al., "Purification and characterisation of the Enantiospecific Dioxygenases from Delftia acidovorans MC1 Initiating the Degradation of Phenoxypropionate and Phenoxyacetate Herbicides," Acta Biotechnologica 23(1):3-17, 2003.

Westendorf et al., "The two enantiospecific dichlorprop/α-ketoglutarate-dioxygenases from Delftia acidovorans MC1—protein and sequence data of RdpA and SdpA," Microbial Research 157:317-322, 2002.

Wright et al., "Robust crop resistance to broadleaf and grass herbicides provided by aryloxyalkanoate dioxygenase transgenes," Proceedings of the National Academy of Science 107(47):20240-20245, 2010.

Zipper et al., "Enantioselective uptake and degradation of the chiral herbicide dichlorprop [(RS)-2-(2,4-dichlorophenoxy)propanoic acid] by Sphingomonas herbicidovorans MH," Journal of Bacteriology 180(13):3368-3374, 1998.

Supplementary Partial European Search Report regarding European Application No. 15850754, dated Mar. 22, 2018.

Leibeling et al., "Posttranslational oxidative modification of (R)-2-(2,4-dichlorophenoxy)propionate/α-ketoglutarate-dependent dioxygenases (RdpA) leads to improved degradation of 2,4-dichlorophenoxyacetate (2,4-D)," Engineering in Life Sciences 13(3):278-291, 2013.13(3):278-291, 2013.

Kukorelli et al., "ACCase inhibitor herbicides—selectivity, weed resistance and fitness cost: a review," International Journal of Pest Management 59(3):165-173, 2013.

Hogan et al., "Site-directed mutagenesis of 2,4-dichlorophenoxyacetic acid/alpha-ketoglutarate dioxygenase: Identification of residues involved in metallocenter formation and substrate binding," Journal of Biological Chemistry 275(17):12400-12409, 2000.

Kim et al., "Assembly of mutations for improving thermostability of *Escherichia coli* AppA2 phytase," Applied Microbiology and Biotechnology 79(5):751-758, 2008.

Skinner et al., "Potential use of additivity of mutational effects in simplifying protein engineering," Proceedings of the National Academy of Sciences 93(20):10753-10757, 1996.

Wright et al., "Robust crop resistance to broadleaf and grass herbicides provided by aryloxyalkanoate dioxygenase transgenes," Proceedings of the National Academy of Sciences 107(47):20240-20245, 2010.

NCBI Reference Sequence No. WP_031942865, dated Jul. 4, 2015.

International Search Report and Written Opinion for International Application No. PCT/US2015/053123, dated Feb. 9, 2016.

Extended European Search Report regarding European Application No. 15850754, dated Jun. 29, 2018.

EMBL Accession No. EF373545, dated Mar. 5, 2007.

Que et al., "Maize transformation technology development for commercial event generation," Frontiers in Plant Science 5:Jan. 19, 2014.

Wang et al., "Comparative analysis of expressed sequences reveals a conserved pattern of optimal codon usage in plants," Plant Molecular Biology 61:699-710, 2006.

Extended European Search Report and Opinion regarding European App. No. 20211532.5, dated May 19, 2021.

Saari (1998). Substrate specificity and spectroscopic properties of 2,4-Dichlorophenoxyacetic acid/[alpha]-ketoglutarate dioxygenase. [Doctoral dissertation, Michigan State University]. MSU Libraries Digital Repository. https://d.lib.msu.edu/etd/27088.

Saari et al., "Stereospecific degradation of the phenoxypropionate herbicide dichlorprop." Journal of Molecular Catalysis B: Enzymatic 6(4):421-428, 1999.

Bolivian Office Action regarding Bolivian App. No SP-0216-2015, dated Feb. 20, 2024.

* cited by examiner

MHAALSPLSQRFERIAVQPLTGVLGAEITGVDLREPLDDSTWNEIL
DAFHTYQVIYFPGQAITNEQHIAFSRRFGPVDPVPLLKSIEGYPEV
QMIRREANESGRVIGDDWHTDSTFLDAPPAAVVMRAIDVPEHGGDT
GFLSMYTAWETLSPTMQATIEGLNVVHSATRVFGSLYQAQNRRFSN
TSVKVMDVDAGDRETVHPLVVTHPGSGRKGLYVNQVYCQRIEGMTD
AESKPLLQFLYEHATRFDFTCRVRWKKDQVLVWDNLCTMHRAVPDY
AGKFRYLTRTTVGGVRPAR

FIG.3

Quizalofop

F1 Control MON-HT2 +CTP

Quizalofop

MON-HT2 no CTP F1 Control

FIG.6E
SEQ ID NO:60 RYLTRTTVGGVRPAR 295
SEQ ID NO:1 RILHRTTVGGVRPAR 295
SEQ ID NO:4 RILHRTTVGGVRPAR 295
SEQ ID NO:7 RILHRTTVGGVRPAR 295
SEQ ID NO:9 RILHRTTVGGVRPAR 295
SEQ ID NO:11 RYLTRTTVGGVRPAR 295
SEQ ID NO:14 RYLTRTTVAGDKPSR 295
SEQ ID NO:18 RYLTRTTVAGDKPSR 295
SEQ ID NO:22 RYLTRTTVGGVRPAR 295
SEQ ID NO:25 RYLTRTTVAGDKPSR 295
SEQ ID NO:28 RYLTRTTVAGDKPSR 295
SEQ ID NO:31 RYLTRTTVAGDKPSR 295
SEQ ID NO:34 RYLTRTTVAGDKPSR 295
SEQ ID NO:37 RYLTRTTVAGDKPSR 295
SEQ ID NO:40 RYLTRTTVAGDRPAR 295
SEQ ID NO:43 RYLTRTTVAGDKPSR 295
SEQ ID NO:46 RYLTRTTVAGDKPSR 295
SEQ ID NO:47 RYLTRTTVAGDKPSR 295
SEQ ID NO:48 RYLTRTTVAGDKPSR 295
SEQ ID NO:49 RYLTRTTVAGDKPSR 295
SEQ ID NO:50 RYLTRTTVAGDKPSR 295
SEQ ID NO:51 RYLTRTTVAGDKPSR 295
SEQ ID NO:52 RYLTRTTVAGDKPSR 295
Consensus RyLtRTTV·G··P·R 295

SEQUENCE LISTING

```
Sequence total quantity: 61
SEQ ID NO: 1            moltype = AA  length = 295
FEATURE                 Location/Qualifiers
source                  1..295
                        mol_type = protein
                        note = Recombinant
                        organism = synthetic construct
SEQUENCE: 1
MHAALSPLSQ RFERIAVQPL TGVLGAEITG VDLREPLSDS TWNEILDAFH TYQVIYFPGQ  60
```

```
AITNEQHIAF SRRFGPVDPV PLLKSIEGYP EVQMIRREAN ESGRVIGDDW HTDSSFLDAP  120
PAAVVMRAID VPEHGGDTGF LSMYTAYDAL SDGLKKLISG LNVVHSATRV FGSLYQAQNR  180
RFSNTSVKVM DVADGDRETV HPLVVTHPGS GRKGLYVNQV YCQRIEGMSE KESEPLLSFL  240
FAHATKPEFT CRVRWKKDQV LVWDNLCTMH YAINDYHGQT RILHRTTVGG VRPAR       295

SEQ ID NO: 2            moltype = DNA  length = 906
FEATURE                 Location/Qualifiers
source                  1..906
                        mol_type = other DNA
                        note = Recombinant
                        organism = synthetic construct
SEQUENCE: 2
atgcatgctg cactgtcccc cctctcccag cgctttgagc gcatcgcggt ccagccgctg  60
accggcgtcc tgggcgccga gatcaccggc gtcgacctgc gcgagccgct cagcgacagc  120
acctggaacg aaatcctcga cgcgttccac acttaccagg tcatctattt tcccggccag  180
gcgatcacca acgaacagca catcgccttc agccggcgct tcggccccgt cgatcccgtg  240
cccctgctca agagcatcga agggtatcca gaggtgcaga tgatccgccg cgaagccaac  300
gaaagcgggc gtgtgatcgg tgatgactgg cacaccgaca gcagcttcct ggacgcaccg  360
ccggccgccg tggtgatgcg cgcgatcgac gtgcccgagc atggcggcga caccggtttt  420
ctgagcatgt acaccgcgta tgatgcgctg tcggatggcc tgaagaaact gatcagcggg  480
ttgaacgtag tgcacagcgc cacgcgtgtg ttcggctcgc tctaccaggc ccagaaccgg  540
cgcttcagca acaccagcgt caaggtgatg gacgtcgcag atggcgaccg tgaaaccgtg  600
cacccccctgg tggtgaccca tccgggcagc ggccgcaagg gcctgtacgt gaaccaggtc  660
tattgccagc gcatcgaggg catgagcgaa aaagaaagcg aaccgctgct gagcttcctg  720
tttgcgcatg cgacaaaacc ggaattcacc tgccgcgtgc gctggaagaa ggaccaggtc  780
ctggtctggg acaacctgtg cacgatgcac tatgccatta acgactacca tggccagacc  840
cgcattctgc atcgcaccac ggtcggtggc gtgcgcccgg cgcgccatca tcaccatcat  900
cactag                                                            906

SEQ ID NO: 3            moltype = DNA  length = 888
FEATURE                 Location/Qualifiers
source                  1..888
                        mol_type = other DNA
                        note = Recombinant
                        organism = synthetic construct
SEQUENCE: 3
atgcacgccg ctctgagccc gcttagccag cgcttcgagc gcatcgccgt gcagccgctg  60
accggcgtgc taggcgctga gatcaccggc gttgacctga gggagccgct tagcgactcc  120
acctggaacg agatcctcga cgccttccac acttaccaag ttatctactt cccaggacag  180
gctatcacga acgaacagca catcgccttc tcgcggaggt tcgggccagt ggacccagtc  240
ccgctgctta agtctatcga aggctaccct gaggtgcaaa tgatccgccg cgaggcgaac  300
gaatccggga gggttattgg cgacgattgg cacactgact ccagcttcct cgatgctcct  360
ccagcagccg tcgtgatgcg ggccatcgac gtgccggagc acggcggcga tacgggtttc  420
ctgtccatgt acactgctta cgacgctctt tctgatggcc tcaagaaact catcagcgga  480
ctcaatgtgg tccactctgc gacccgtgtc tttggctcgc tctatcaggc gcagaatagg  540
cgcttcagca acacctccgt gaaggtcatg gacgtggcgg atggagacag ggagactgtc  600
cacccgctcg tcgttactca ccctgggtcc ggccgtaagg gtctgtacgt gaaccaggtg  660
tactgtcagc gaattgaggg tatgagtgag aaggagtccg agccgctgct cagtttcctc  720
ttcgcgcacg ccaccaagcc cgagttcacc tgccgcgtcc gctggaagaa ggatcaagtc  780
ctggtgtggg acaacctctg caccatgcac tacgccatca atgactatca tggtcaaacc  840
cggattcttc atcgcacaac ggttggcggc gtgagacctg cccggtga              888

SEQ ID NO: 4            moltype = AA  length = 295
FEATURE                 Location/Qualifiers
source                  1..295
                        mol_type = protein
                        note = Recombinant
                        organism = synthetic construct
SEQUENCE: 4
MHAALSPLSQ RFERIAVQPL TGVLGAEITG VDLREPLDDS TWNEILDAFH TYQVIYFPGQ  60
AITNEQQIAF SRRFGPVDPV PLLKSIEGYP EVQMIRREAN ESGRVIGDDW HTDSTFLDAP  120
PAAVVMRAID VPEHGGDTGF LSMYTAYDAL SDGLKKLISG LNVVHSATRV FGSLYQAQNR  180
RFSNTSVKVM DVADGDRETV HPLVVTHPGS GRKGLYVNQV YCQRIEGMSE KESEPLLSFL  240
FAHATKPEFT CRVRWKKDQV LVWDNLCTMH YAINDYHGQT RILHRTTVGG VRPAR       295

SEQ ID NO: 5            moltype = DNA  length = 906
FEATURE                 Location/Qualifiers
source                  1..906
                        mol_type = other DNA
                        note = Recombinant
                        organism = synthetic construct
SEQUENCE: 5
atgcatgctg cactgtcccc cctctcccag cgctttgagc gcatcgcggt ccagccgctg  60
accggcgtcc tgggcgccga gatcaccggc gtcgacctgc gcgagccgct cgacgacagc  120
acctggaacg aaatcctcga cgcgttccac acttaccagg tcatctattt tcccggccag  180
gcgatcacca acgaacagca gatcgccttc agccggcgct tcggccccgt cgatcccgtg  240
cccctgctca agagcatcga agggtatcca gaggtgcaga tgatccgccg cgaagccaac  300
gaaagcgggc gtgtgatcgg tgatgactgg cacaccgaca gcaccttcct ggacgcaccg  360
ccggccgccg tggtgatgcg cgcgatcgac gtgcccgagc atggcggcga caccggtttt  420
```

```
ctgagcatgt acaccgcgta tgatgcgctg tcggatggcc tgaagaaact gatcagcggg  480
ttgaacgtag tgcacagcgc cacgcgtgtg ttcggctcgc tctaccaggc ccagaaccgg  540
cgcttcagca acaccagcgt caaggtgatg gacgtcgacg cgggcgaccg tgaaaccgtg  600
cacccccctgg tggtgaccca tccgggcagc ggccgcaagg gcctgtacgt gaaccaggtc  660
tattgccagc gcatcgaggg catgagcgaa aaagaaagcg aaccgctgct gagcttcctg  720
tttgcgcatg cgacaaaacc ggaattcacc tgccgcgtgc gctggaagaa ggaccaggtc  780
ctggtctggg acaacctgtg cacgatgcac tatgccatta acgactacca tggccagacc  840
cgcattctgc atcgcaccac ggtcggtggc gtgcgcccgg cgcgccatca tcaccatcat  900
cactag                                                             906

SEQ ID NO: 6            moltype = DNA  length = 888
FEATURE                 Location/Qualifiers
source                  1..888
                        mol_type = other DNA
                        note = Recombinant
                        organism = synthetic construct
SEQUENCE: 6
atgcacgccg ctctgagccc gcttagccag cgcttcgagc gcatcgccgt gcagccgctg  60
accggcgtgc taggcgctga gatcaccggc gttgacctga gggagccgct tgacgactcc  120
acctggaacg agatcctcga cgccttccac acttaccaag ttatctactt cccaggacag  180
gctatcacga acgaacagca gatcgccttc tcgcggaggt tcgggccagt ggacccagtc  240
ccgctgctta agtctatcga aggctaccct gaggtgcaaa tgatccgccg cgaggcgaac  300
gaatccggga gggttattgg cgacgattgg cacactgact ccaccttcct cgatgctcct  360
ccagcagccg tcgtgatgcg ggccatcgac gtgccggagc acggcggcga tacgggtttc  420
ctgtccatgt acactgctta cgacgctctt tctgatggcc tcaagaaact catcagcgga  480
ctcaatgtgg tccactctgc gacccgtgtc tttggctcgc tctatcaggc gcagaatagg  540
cgcttcagca acacctccgt gaaggtcatg gacgtggacg cgggagacag ggagactgtc  600
cacccgctcg tcgttactca ccctgggtcc ggccgtaagg gtctgtacgt gaaccaggtg  660
tactgtcagc gaattgaggg tatgagtgag aaggagtccg agccgctgct cagtttcctc  720
ttcgcgcacg ccaccaagcc cgagttcacc tgccgcgtcc gctggaagaa ggatcaagtc  780
ctggtgtggg acaacctctg caccatgcac tacgccatca atgactatca tggtcaaacc  840
cggattcttc atcgcacaac ggttggcggc gtgagacctg cccggtga                888

SEQ ID NO: 7            moltype = AA  length = 295
FEATURE                 Location/Qualifiers
source                  1..295
                        mol_type = protein
                        note = Recombinant
                        organism = synthetic construct
SEQUENCE: 7
MHAALSPLSQ RFERIAVQPL TGVLGAEITG VDLREPLSDS TWNEILDAFH TYQVIYFPGQ  60
AITNEQHIAF SRRFGPVDPV PLLKSIEGYP EVQMIRREAN ESGRVIGDDW HSDSTFLDAP  120
PAAVVMRAID VPEHGGDTGF LSMYTAYDAL SDGLKKLISG LNVVHSATRV FGSLYQAQNR  180
RFSNTSVKVM DVDAGDRETV HPLVVTHPGS GRKGLYVNQV YCQRIEGMSE KESEPLLSFL  240
FAHATKPEFT CRVRWKKDQV LVWDNLCTMH YAINDYHGQT RILHRTTVGG VRPAR       295

SEQ ID NO: 8            moltype = DNA  length = 906
FEATURE                 Location/Qualifiers
source                  1..906
                        mol_type = other DNA
                        note = Recombinant
                        organism = synthetic construct
SEQUENCE: 8
atgcatgctg cactgtcccc cctctcccag cgctttgagc gcatcgcggt ccagccgctg  60
accggcgtcc tgggcgccga gatcaccggc gtcgacctgc gcgagccgct cagcgacagc  120
acctggaacg aaatcctcga cgcgttccac acttaccagg tcatctattt tcccggccag  180
gcgatcacca acgaacagca catcgccttc agccggcgct tcggccccgt cgatcccgtg  240
cccctgctca agagcatcga agggtatcca gaggtgcaga tgatccgccg cgaagccaac  300
gaaagcgggc gtgtgatcgg tgatgactgg cacagcgaca gcaccttcct ggacgcaccg  360
ccggccgccg tggtgatgcg cgcgatcgac gtgcccgagc atggcggcga caccggtttt  420
ctgagcatgt acaccgcgta tgatgcgctg tcggatggcc tgaagaaact gatcagcggg  480
ttgaacgtag tgcacagcgc cacgcgtgtg ttcggctcgc tctaccaggc ccagaaccgg  540
cgcttcagca acaccagcgt caaggtgatg gacgtcgacg cgggcgaccg tgaaaccgtg  600
cacccccctgg tggtgaccca tccgggcagc ggccgcaagg gcctgtacgt gaaccaggtc  660
tattgccagc gcatcgaggg catgagcgaa aaagaaagcg aaccgctgct gagcttcctg  720
tttgcgcatg cgacaaaacc ggaattcacc tgccgcgtgc gctggaagaa ggaccaggtc  780
ctggtctggg acaacctgtg cacgatgcac tatgccatta acgactacca tggccagacc  840
cgcattctgc atcgcaccac ggtcggtggc gtgcgcccgg cgcgccatca tcaccatcat  900
cactag                                                             906

SEQ ID NO: 9            moltype = AA  length = 295
FEATURE                 Location/Qualifiers
source                  1..295
                        mol_type = protein
                        note = Recombinant
                        organism = synthetic construct
SEQUENCE: 9
MHAALSPLSQ RFERIAVQPL TGVLGAEITG VDLREPLDDS TWNEILDAFH TYQVIYFPGQ  60
AITNEQHIAF SRRFGPVDPV PLLKSIEGYP EVQMIRREAN ESGRVLGDDW HTDSTFLDAP  120
```

```
PAAVVMRAID VPEHGGDTGF LSMYTAYDAL SDGLKKLISG LNVVHSATRV FGSLYQAQNR  180
RFSNTSVKVM DVADGDRETV HPLVVTHPGS GRKGLYVNQV YCQRIEGMSE KESEPLLSFL  240
FAHATKPEFT CRVRWKKDQV VVWDNLCTMH YAINDYHGQT RILHRTTVGG VRPAR       295

SEQ ID NO: 10          moltype = DNA  length = 906
FEATURE                Location/Qualifiers
source                 1..906
                       mol_type = other DNA
                       note = Recombinant
                       organism = synthetic construct
SEQUENCE: 10
atgcatgctg cactgtcccc cctctcccag cgctttgagc gcatcgcggt ccagccgctg  60
accggcgtcc tgggcgccga gatcaccggc gtcgacctgc gcgagccgct cgacgacagc  120
acctggaacg aaatcctcga cgcgttccac acttaccagg tcatctattt tcccggccag  180
gcgatcacca acgaacagca catcgccttc agccggcgct tcggccccgt cgatcccgtg  240
cccctgctca agagcatcga agggtatcca gaggtgcaga tgatccgccg cgaagccaac  300
gaaagcgggc gtgtgctggg tgatgactgg cacaccgaca gcaccttcct ggacgcaccg  360
ccggccgccg tggtgatgcg cgcgatcgac gtgcccgagc atggcggcga caccggtttt  420
ctgagcatgt acaccgcgta tgatgcgctg tcggatggcc tgaagaaact gatcagcggg  480
ttgaacgtag tgcacagcgc cacgcgtgtg ttcggctcgc tctaccaggc ccagaaccgg  540
cgcttcagca acaccagcgt caaggtgatg gacgtcgcag atggcgaccg tgaaaccgtg  600
cacccccctgg tggtgaccca tccgggcagc ggccgcaagg gcctgtacgt gaaccaggtc  660
tattgccagc gcatcgaggg catgagcgaa aagaaaagcg aaccgctgct gagcttcctg  720
tttgcgcatg cgacaaaacc ggaattcacc tgccgcgtgc gctggaagaa ggaccaggtc  780
gtggtctggg acaacctgtg cacgatgcac tatgccatta acgactacca tggccagacc  840
cgcattctgc atcgcaccac ggtcggtggc gtgcgcccgg cgcgccatca tcaccatcat  900
cactag                                                             906

SEQ ID NO: 11          moltype = AA  length = 295
FEATURE                Location/Qualifiers
source                 1..295
                       mol_type = protein
                       note = Recombinant
                       organism = synthetic construct
SEQUENCE: 11
MHAALSPLSQ RFERIAVQPL TGVLGAEITG VDLREPLDDS TWNEILDAFH TYQVIYFPGQ  60
AITNEQHIAF SRRFGPVDPV PLLKSIEGYP EVQMIRREAN ESGRVIGENW HTDSTFLDAP  120
PAAVVMYAKE IPPYGGDTLF TSMYTAWETL SPTMQATIEG LNVVHSATRV FGSLYQAQNR  180
RFSNTSVKVM DVDAGDRETV HPLVVTHPET GRKGLYVNQV YCQRIEGMSE KESEPLLSFL  240
FAHATKPEFT CRVRWQEGDV LVWDNLCTQH YAVPDYAGKF RYLTRTTVGG VRPAR       295

SEQ ID NO: 12          moltype = DNA  length = 906
FEATURE                Location/Qualifiers
source                 1..906
                       mol_type = other DNA
                       note = Recombinant
                       organism = synthetic construct
SEQUENCE: 12
atgcatgctg cactgtcccc cctctcccag cgctttgagc gcatcgcggt ccagccgctg  60
accggcgtcc tgggcgccga gatcaccggc gtcgacctgc gcgagccgct cgacgacagc  120
acctggaacg aaatcctcga cgcgttccac acttaccagg tcatctattt tcccggccag  180
gcgatcacca acgaacagca catcgccttc agccggcgct tcggccccgt cgatcccgtg  240
cccctgctca agagcatcga agggtatcca gaggtgcaga tgatccgccg cgaagccaac  300
gaaagcgggc gtgtgatcgg tgaaaactgg cacaccgaca gcaccttcct ggacgcaccg  360
ccggccgccg tggtgatgta tgcgaaagaa attccccccgt atggcggcga caccctgttt  420
accagcatgt acaccgcgtg ggagacgctg tcgcccacca tgcaggccac catcgaaggg  480
ttgaacgtag tgcacagcgc cacgcgtgtg ttcggctcgc tctaccaggc ccagaaccgg  540
cgcttcagca acaccagcgt caaggtgatg gacgtcgacg cgggcgaccg tgaaaccgtg  600
cacccccctgg tggtgaccca tccggaaacc ggccgcaagg gcctgtacgt gaaccaggtc  660
tattgccagc gcatcgaggg catgagcgaa aagaaaagcg aaccgctgct gagcttcctg  720
tttgcgcatg cgacaaaacc ggaattcacc tgccgcgtgc gctggcagga aggcgatgtc  780
ctggtctggg acaacctgtg cacgcagcac tatgccgtac ccgactacgc gggcaagttc  840
cgctacctga cgcgcaccac ggtcggtggc gtgcgcccgg cgcgccatca tcaccatcat  900
cactag                                                             906

SEQ ID NO: 13          moltype = DNA  length = 888
FEATURE                Location/Qualifiers
source                 1..888
                       mol_type = other DNA
                       note = Recombinant
                       organism = synthetic construct
SEQUENCE: 13
atgcacgccg ctctgagccc gcttagccag cgcttcgagc gcatcgccgt gcagccgctg  60
accggcgtgc taggcgctga gatcaccggc gttgacctga gggagccgct tgacgactcc  120
acctggaacg agatcctcga cgccttccac acttaccaag ttatctactt cccaggacag  180
gctatcacga acgaacagca catcgccttc tcgcggaggt tcgggccagt ggacccagtc  240
ccgctgctta agtctatcga aggctaccct gaggtgcaaa tgatccgccg cgaggcgaac  300
gaatccggga gggttattgg cgagaactgg cacactgact cccaccttcct cgatgctcct  360
ccagcagccg tcgtgatgta cgccaaggag atcccgccct acggcggcga tacgctcttc  420
```

```
acctccatgt acactgcttg ggagaccctt tctccgacca tgcaagccac catcgaggga  480
ctcaatgtgg tccactctgc gacccgtgtc tttggctcgc tctatcaggc gcagaatagg  540
cgcttcagca acacctccgt gaaggtcatg gacgtggacg ccggagacag ggagactgtc  600
cacccgctcg tcgttactca ccctgagacc ggccgtaagg gtctgtacgt gaaccaggtg  660
tactgtcagc gaattgaggg tatgagtgag aaggagtccg agccgctgct cagtttcctc  720
ttcgcgcacg ccaccaagcc cgagttcacc tgccgcgtcc gctggcaaga gggcgacgtc  780
ctggtgtggg acaacctctg cacccagcac tacgccgtgc cggactatgc cgggaagttc  840
cgctacctta cccgcacaac ggttggcggc gtgagacctg cccggtga              888

SEQ ID NO: 14          moltype = AA  length = 295
FEATURE                Location/Qualifiers
source                 1..295
                       mol_type = protein
                       note = Recombinant
                       organism = synthetic construct
SEQUENCE: 14
MHAALTPLTN KYRFIDVQPL TGVLGAEITG VDLREPLDDS TWNEILDAFH TYQVIYFPGQ  60
AITNEQHIAF SRRFGPVDPV PILKSIEGYP EVQMIRREAN ESSRFIGDDW HTDSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATKFDFT CRVRWKKDQV LVWDNLCTMH RAVPDYAGKF RYLTRTTVAG DKPSR       295

SEQ ID NO: 15          moltype = DNA  length = 906
FEATURE                Location/Qualifiers
source                 1..906
                       mol_type = other DNA
                       note = Recombinant
                       organism = synthetic construct
SEQUENCE: 15
atgcacgcgg ctctgacccc gcttaccaac aaataccgtt tcatcgacgt tcagccgctg  60
accggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgattctca aatctatcga aggttacccg gaagttcaga tgatccgtcg cgaagcgaac  300
gaatctagcc gttttattgg tgacgattgg cacaccgact ccaccttcct ggacgcgccg  360
ccagctgcag ttgtgatgcg tgctattgaa gttccggaat acggtggcga caccggtttc  420
ctgtccatgt actctgcttg ggaaaccctg tccccgacca tgcaggctac cattgaaggt  480
ctgaacgttg tgcactccgc aaccaaagtg ttcggcagcc tgtaccaggc aaccaactgg  540
cgcttcagca acactagtgt gaaagtgatg gatgtggatg caggcgatcg tgagactgtg  600
cacccgctgg tggtaactca cccggttacc ggccgtcgtg cgctgtactg caaccaggta  660
tattgccaga aaattcaggg catgactgat gcagagtcaa aatctctgct ccaatttctg  720
tatgagcacg ccactaaatt tgattttact tgccgtgtcc gttggaaaaa ggatcaagta  780
ctggtatggg ataatctgtg tacgatgcac cgcgccgtac ctgattatgc cggcaaattt  840
cgctatttga cgcgcacgac agtcgcgggg gacaaacctt ctcgccatca ccatcatcat  900
cattag                                                             906

SEQ ID NO: 16          moltype = DNA  length = 888
FEATURE                Location/Qualifiers
source                 1..888
                       mol_type = other DNA
                       note = Recombinant
                       organism = synthetic construct
SEQUENCE: 16
atgcacgcgg cgctgactcc tctcaccaac aagtatcgct ttatcgacgt gcagccgctg  60
acaggcgtcc tcggtgcaga gattacaggc gtggatctgc gggagcctct cgatgacagc  120
acttggaatg agatcctgga cgcctttcac acctaccaag tgatctactt tccgggtcaa  180
gctatcacta acgagcagca catcgcgttc tcccgccggt tcggccctgt ggacccggtg  240
ccgatcttaa agagtatcga gggctatcca gaggtgcaga tgatacggcg cgaggcgaac  300
gagagcagcc ggttcatcgg agatgactgg cacaccgatt ccaccttcct ggacgctccg  360
cctgccgccg tggtgatgag agctatcgaa gtgccggagt atggaggtga cacaggcttc  420
ctctccatgt acagtgcctg ggagacactc tcgcctacga tgcaagctac catcgaaggc  480
ttaaacgtgg tccactcggc gacgaaggtc ttcgggtcat tgtaccaggc gactaattgg  540
cgcttctcga acaccagcgt gaaagtgatg gacgtggacg ccggagatag agagactgtg  600
cacccactcg tcgtgacgca tcctgttacg ggaaggcgcg cactctactg caaccaggtg  660
tactgccaga agatccaggg aatgacggac gcggagtcga agtccctgtt gcaattcctt  720
tacgagcacg ccaccaagtt cgacttcacc tgccgggtcc ggtggaagaa ggaccaagtc  780
ctggtgtggg acaacctgtg taccatgcac cgcgccgtcc cggactacgc tgggaaattc  840
agatacctga cccgcaccac cgtggcggga gacaagccgt cgcgttga              888

SEQ ID NO: 17          moltype = DNA  length = 888
FEATURE                Location/Qualifiers
source                 1..888
                       mol_type = other DNA
                       note = Recombinant
                       organism = synthetic construct
SEQUENCE: 17
atgcacgcgg ctttgacacc tttgaccaac aagtatcggt tcatcgacgt tcaaccactc  60
acaggcgtgc tcggcgcaga gattaccgga gtggacctga gggagccctt agacgactcc  120
acttggaacg agatcctcga cgcctttcac acctaccaag ttatctactt tcctggacag  180
```

```
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggttcatagg cgacgattgg cacacagaca gcaccttcct tgacgctcct  360
ccggctgccg tggttatgcg cgcaatagag gtgccggagt acggcggcga taccggtttc  420
ctatcaatgt actctgcatg ggagacgctc tcaccaacga tgcaagccac cattgaaggt  480
ctaaacgtgg ttcactcagc tactaaggtc ttcggaagtc tttaccaggc gacgaattgg  540
aggttcagta acaccagtgt gaaggtgatg gatgtggacg ctggagacag ggagacggtg  600
catccactcg tagttacaca ccctgtaact ggacgcagag ccctttactg caaccaggtt  660
tactgccaga agatccaggg aatgactgat gcggagtcta agtccctgct tcaattcctc  720
tacgaacacg ccaccaaatt cgacttcact tgtcgtgttc ggtggaagaa ggaccaagtg  780
ctcgtgtggg ataacctttg caccatgcac cgagcagtac cagactacgc cgggaaattc  840
cgctatctca cccgcactac agtggccgga gacaagccta gccgctga             888

SEQ ID NO: 18          moltype = AA  length = 295
FEATURE                Location/Qualifiers
source                 1..295
                       mol_type = protein
                       note = Recombinant
                       organism = synthetic construct
SEQUENCE: 18
MHAALTPLTN KYRFIDVQPL TGVLGAEITG VDLREPLDDS TWNEILDAFH TYQVIYFPGQ  60
AITNEQHIAF SRRFGPVDPV PLLKSIEGYP EVQMIRREAN ESSRVIGDDW HSDSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATKFDFT CRVRWKKDQV LVWDNLCTMH RAAPDYAGKF RYLTRTTVAG DKPSR       295

SEQ ID NO: 19          moltype = DNA  length = 906
FEATURE                Location/Qualifiers
source                 1..906
                       mol_type = other DNA
                       note = Recombinant
                       organism = synthetic construct
SEQUENCE: 19
atgcacgcgg ctctgacccc gcttaccaac aaataccgtt tcatcgacgt tcagccgctg  60
accggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgctgctca aatctatcga aggttacccg gaagttcaga tgatccgtcg cgaagcgaac  300
gaatctagcc gtgttattgg tgacgattgg cacagcgact ccaccttcct ggacgcgccg  360
ccagctgcag ttgtgatgcg tgctattgaa gttccggaat acggtggcga caccggtttc  420
ctgtccatgt actctgcttg ggaaaccctg tccccgacca tgcaggctac cattgaaggt  480
ctgaacgttg tgcactccgc aaccaaagtg ttcggcagcc tgtaccaggc aaccaactgg  540
cgcttcagca acactagtgt gaaagtgatg gatgtggatg caggcgatcg tgagactgtg  600
cacccgctgg tggtaactca cccggttacc ggccgtcgtg cgctgtactg caaccaggta  660
tattgccaga aaattcaggg catgactgat gcagagtcaa aatctctgct ccaatttctg  720
tatgagcacg ccactaaatt tgattttact tgccgtgtcc gttggaaaaa ggatcaagta  780
ctggtatggg ataatctgtg tacgatgcac cgcgccgcgc ctgattatgc cggcaaattt  840
cgctatttga cgcgcacgac agtcgcgggg gacaaacctt ctcgccatca ccatcatcat  900
cattag                                                            906

SEQ ID NO: 20          moltype = DNA  length = 888
FEATURE                Location/Qualifiers
source                 1..888
                       mol_type = other DNA
                       note = Recombinant
                       organism = synthetic construct
SEQUENCE: 20
atgcacgcgg cgctgactcc tctcaccaac aagtatcgct ttatcgacgt gcagccgctg  60
acaggcgtcc tcggtgcaga gattacaggc gtggatctgc gggagcctct cgatgacagc  120
acttggaatg agatcctgga cgcctttcac acctaccaag tgatctactt tccgggtcaa  180
gctatcacta acgagcagca catcgcgttc tcccgccggt tcggccctgt ggacccggtg  240
ccgctgttaa agagtatcga gggctatcca gaggtgcaga tgatacggcg cgaggcgaac  300
gagagcagcc gggtgatcgg agatgactgg cactccgatt ccaccttcct ggacgctccg  360
cctgccgccg tggtgatgag agctatcgaa gtgccggagt atggaggtga cacaggcttc  420
ctctccatgt acagtgcctg ggagacactc tcgcctacga tgcaagctac catcgaaggc  480
ttaaacgtgg tccactcggc gacgaaggtc ttcgggtcat tgtaccaggc gactaattgg  540
cgcttctcga acaccagcgt gaaagtgatg gacgtggacg ccggagatag agagactgtg  600
cacccactcg tcgtgacgca tcctgttacg ggaaggcgcg cactctactg caaccaggtg  660
tactgccaga agatccaggg aatgacggac gcggagtcga agtccctgtt gcaattcctt  720
tacgagcacg ccaccaagtt cgacttcacc tgccgggtcc ggtggaagaa ggaccaagtc  780
ctggtgtggg acaacctgtg taccatgcac cgcgccgccc cggactacgc tgggaaattc  840
agatacctga cccgcaccac cgtggcggga gacaagccgt cgcgttga             888

SEQ ID NO: 21          moltype = DNA  length = 888
FEATURE                Location/Qualifiers
source                 1..888
                       mol_type = other DNA
                       note = Recombinant
                       organism = synthetic construct
```

```
SEQUENCE: 21
atgcacgcag cccttactcc actgacgaac aagtatcgct tcatcgacgt gcagccactc  60
acgggtgtac tcggagccga gatcacggga gtggatctgc gcgagccgct cgatgactct  120
acatggaacg agatcctaga cgctttccac acttatcaag ttatctactt tccaggacaa  180
gccatcacta acgagcaaca catcgcgttc tcacgtcggt tcgggcctgt tgatcctgtg  240
ccgctcctca agtcaatcga gggttatcca gaagttcaga tgatccggcg cgaggctaat  300
gagtcatccc gtgttatcgg tgatgactgg cactcggaca gtacattcct cgacgcacca  360
ccggccgcag ttgtgatgag ggctatcgaa gtgccggaat acggtggtga cactgggttc  420
ctgtcaatgt actctgcatg ggagaccctt agtcccacta tgcaagcaac catcgaaggg  480
ctcaacgttg tgcattcagc tactaaagta ttcggttccc tttatcaggc gacaaactgg  540
cggttcagca ataccagtgt taaagttatg gatgtggatg ctggagacag ggaaacggtc  600
caccctcttg tcgtcacgca cccagttaca gggcgtcgag cgctttactg caatcaggtg  660
tactgtcaga agattcaagg aatgaccgat gcggagtcca aatcactgtt acaattcttg  720
tacgagcacg ccactaagtt cgatttcacg tgccgagtgc gctggaagaa ggatcaagtg  780
ctcgtttggg acaacttgtg caccatgcac cgggcagctc ccgactacgc gggcaagttc  840
cgttatctca ctcgcacaac tgtcgctgga gacaagccct cccgatga               888

SEQ ID NO: 22          moltype = AA  length = 295
FEATURE                Location/Qualifiers
source                 1..295
                       mol_type = protein
                       note = Recombinant
                       organism = synthetic construct
SEQUENCE: 22
MHAALSPLSQ RFERIAVQPL TGVLGAEITG VDLREPLDDS TWNEILDAFH TYQVIYFPGQ  60
AITNEQHIAF SRRFGPVDPV PLLKSIEGYP EVQMIRREAN ESGRVIGDDW HTDSTFLDAP  120
PAAVVMYAKE VPPYGGDTLF ASMYTAWETL SPTMQATIEG LNVVHSATRV FGSLYQAQNR  180
RFSNTSVKVM DVDAGDRETV HPLVVTHPET GRKGLYVNQV YCQRIEGMSE KESEPLLSFL  240
FAHATKPEFT CRVRWQEGQV LVWDNLCTQH FAVPDYAGKF RYLTRTTVGG VRPAR       295

SEQ ID NO: 23          moltype = DNA  length = 906
FEATURE                Location/Qualifiers
source                 1..906
                       mol_type = other DNA
                       note = Recombinant
                       organism = synthetic construct
SEQUENCE: 23
atgcacgcgg ctctgagccc gcttagccag cgtttcgaac gtatcgcggt tcagccgctg  60
accggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgctgctca aatctatcga aggttacccg gaagttcaga tgatccgtcg cgaagcgaac  300
gaatctggtc gtgttattgg tgacgactgg cacaccgact ctaccttcct ggacgcgccg  360
ccagctgcag ttgtgatgta cgctaaagaa gtgccgccat acggtggcga caccctgttc  420
gcgtccatgt acaccgcttg ggaaaccctg tccccgacca tgcaggctac cattgaaggt  480
ctgaacgttg tgcactccgc aactcgtgtt ttcggctccc tgtaccaggc acagaaccgt  540
cgcttcagca acactagcgt taaagtgatg gatgtggatg caggcgatcg tgaaactgtg  600
cacccgctgg tggtaactca cccggaaact ggccgtaaag gcctgtacgt gaaccaggta  660
tattgccagc gtattgaagg catgagtgag aaagagtcgg agccgctgct ctcatttctg  720
tttgcacacg ccactaaacc agagtttact tgccgtgtcc gttggcaaga gggccaggta  780
ctggtatggg ataatctgtg tacgcaacac ttcgccgtac ctgattatgc cggcaagttt  840
cgctatttga cgcgcacgac agtcggcggg gtccgccctg cccgccatca ccatcaccat  900
cattag                                                             906

SEQ ID NO: 24          moltype = DNA  length = 888
FEATURE                Location/Qualifiers
source                 1..888
                       mol_type = other DNA
                       note = Recombinant
                       organism = synthetic construct
SEQUENCE: 24
atgcacgcgg ccctgtctcc tctgtcccag cggttcgagc gcatcgcggt ccagccgcta  60
acgggtgtcc tgggcgcgga aatcaccgga gttgatctga gagagccttt agacgacagc  120
acctggaacg agatcctcga tgcctttcac acataccaag ttatctactt tcccggccaa  180
gccatcacga acgagcagca catcgcgttt agccggaggt ttggcccggt tgatccggtt  240
cctctgctta agtcaattga gggttaccca gaggtgcaga tgatccgccg cgaggccaac  300
gaatctgggc gtgtcatagg cgacgattgg catacggaca gcacctttct cgacgctcct  360
ccggccgcag tcgtgatgta cgcgaaggag gtgccgcctt acggcggcga taccctgttc  420
gcgtcgatgt acacggcctg ggagacgctc agcccgacca tgcaagccac aatagagggt  480
ctaaatgtgg tccactccgc gacgcgggtg ttcgggagcc tctaccaggc gcagaacaga  540
cggttctcga acacatcagt caaggtgatg gacgtggatg ccggagatcg tgaaactgtt  600
cacccacttg tggtcaccca tccagagacg ggaaggaaag gactttacgt gaaccaggtg  660
tactgccagc ggatcgaggg catgtccgag aaggagagtg agccattgct gagctttcta  720
ttcgcgcacg caactaagcc cgagttcacg tgccgcgtcc gatggcaaga gggccaagtt  780
ctcgtctggg ataacttgtg cacacagcac ttcgcggttc ccgattacgc cggaaagttc  840
cgctatctca cacgcaccac tgtgggaggc gttcgtcccg cgcggtga               888

SEQ ID NO: 25          moltype = AA  length = 295
FEATURE                Location/Qualifiers
```

-continued

```
source                1..295
                      mol_type = protein
                      note = Recombinant
                      organism = synthetic construct
SEQUENCE: 25
MHAALTPLTN KYRFIDVQPL TGVLGAEITG VDLREPLDDS TWNEILDAFH TYQVIYFPGQ  60
AITNEQHIAF SRRFGPVDPV PLLKSIEGYP EVQMIRREAN ESGRVIGDDW HTDSTFLDAP  120
PAAVVMYARE VPPYGGDTGF LSMYTAWETL SPTMQATIEG LNVVHSATRV FGSLYQAQNR  180
RYSNTSVKVM DVDAGDRETV HPLVVSHPVT GRRALYCNQV YCQRIEGMTD AESKSLLQFL  240
YEHATKFDFT CRVRWKKDQV LVWDNLCTMH RAVPDYAGKF RYLTRTTVAG DKPSR       295

SEQ ID NO: 26         moltype = DNA  length = 906
FEATURE               Location/Qualifiers
source                1..906
                      mol_type = other DNA
                      note = Recombinant
                      organism = synthetic construct
SEQUENCE: 26
atgcacgcgg ctctgacccc gcttaccaac aaataccgtt tcatcgacgt tcagccgctg  60
accggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgctgctca aatctatcga aggttacccg gaagttcaga tgatccgtcg cgaagcgaac  300
gaatctggtc gtgttattgg tgacgattgg cacaccgact ccaccttcct ggacgcgccg  360
ccagctgcag ttgtgatgta cgctcgtgaa gttccgccgt acggtggcga caccggtttc  420
ctgtccatgt acaccgcttg ggaaaccctg tccccgacca tgcaggctac cattgaaggt  480
ctgaacgttg tgcactccgc aacccgtgtg ttcggcagcc tgtaccaggc acagaaccgt  540
cgctacagca acactagtgt gaaagtgatg gatgtggatg caggcgatcg tgagactgtg  600
cacccgctgg tggtatctca cccggttacc ggccgtcgtg cgctgtactg caaccaggta  660
tattgccagc gtattgaggg catgactgat gcagagtcaa aatctctgct ccaatttctg  720
tatgagcacg ccactaaatt tgattttact tgccgtgtcc gttggaaaaa ggatcaagta  780
ctggtatggg ataatctgtg tacgatgcac cgcgccgtac ctgattatgc cggcaaattt  840
cgctatttga cgcgcacgac agtcgcgggg gacaaacctt ctcgccatca ccatcatcat  900
cattag                                                             906

SEQ ID NO: 27         moltype = DNA  length = 888
FEATURE               Location/Qualifiers
source                1..888
                      mol_type = other DNA
                      note = Recombinant
                      organism = synthetic construct
SEQUENCE: 27
atgcacgctg ctctgactcc actcacaaac aagtaccggt tcatcgacgt gcaaccgctg  60
accggcgtct tgggtgcgga aatcaccggc gtggacttgc gggagccgct ggatgacagc  120
acatggaacg agatcctcga tgcgttccac acctaccaag tgatctattt cccaggccag  180
gccattacga acgagcagca catcgcgttc agtcgaaggt tcgggcctgt ggacccggtt  240
ccgctgctta agagtatcga gggctacccg gaagtacaga tgattcgccg cgaagcgaat  300
gagtccgggc gagtgatcgg cgatgactgg cacaccgaca gcacgttcct cgacgcgccg  360
cctgccgctg tcgtgatgta cgcacgggag gtgccaccct acggcggaga tacgggattc  420
ctttcaatgt acacggcatg ggagacactc tctccgacca tgcaagcaac gatagagggc  480
ttgaacgtgg tgcactccgc cacgagggtc ttcggcagcc tctaccaagc ccagaaccgc  540
cggtactcca acactagcgt gaaagtgatg gacgtggatg cgggcgaccg ggagaccgtg  600
catcctctag ttgtgagcca cccggtgact ggccgacggg cgctgtactg caaccaggtc  660
tattgccagc gcatcgaggg catgaccgac gcggagtcga aatctctgct ccaattcctg  720
tacgagcacg ccacgaagtt cgacttcacc tgccgggttc gctggaagaa ggatcaagtg  780
ctagtgtggg acaacctctg cactatgcac aggctgtgc cggactatgc tggcaaattc  840
cgttacctta cccggaccac tgtggcgggc gacaagccaa gcagatga               888

SEQ ID NO: 28         moltype = AA  length = 295
FEATURE               Location/Qualifiers
source                1..295
                      mol_type = protein
                      note = Recombinant
                      organism = synthetic construct
SEQUENCE: 28
MHAALTPLTN KYRFIDVQPL TGVLGAEITG VDLREPLDDS TWNEILDAFH TYQVIYFPGQ  60
AITNEQHIAF SRRFGPVDPV PLLKSIEGYP EVQMIRREAN ESGRVIGDDW HTDSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATKFDFT CRVRWKKDQV LVWDNLCTMH RAVPDYAGKF RYLTRTTVAG DKPSR       295

SEQ ID NO: 29         moltype = DNA  length = 906
FEATURE               Location/Qualifiers
source                1..906
                      mol_type = other DNA
                      note = Recombinant
                      organism = synthetic construct
SEQUENCE: 29
atgcacgcgg ctctgacccc gcttaccaac aaataccgtt tcatcgacgt tcagccgctg  60
```

```
accggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgctgctca aatctatcga aggttacccg gaagttcaga tgatccgtcg cgaagcgaac  300
gaatctggtc gtgttattgg tgacgattgg cacaccgact ccaccttcct ggacgcgccg  360
ccagctgcag ttgtgatgcg tgctattgaa gttccggaat acggtggcga caccggtttc  420
ctgtccatgt actctgcttg ggaaaccctg tccccgacca tgcaggctac cattgaaggt  480
ctgaacgttg tgcactccgc aaccaaagtg ttcggcagcc tgtaccaggc aaccaactgg  540
cgcttcagca acactagtgt gaaagtgatg gatgtggatg caggcgatcg tgagactgtg  600
cacccgctgg tggtaactca cccggttacc ggccgtcgtg cgctgtactg caaccaggta  660
tattgccaga aaattcaggg catgactgat gcagagtcaa aatctctgct ccaatttctg  720
tatgagcacg ccactaaatt tgattttact tgccgtgtcc gttggaaaaa ggatcaagta  780
ctggtatggg ataatctgtg tacgatgcac cgcgccgtac ctgattatgc cggcaaattt  840
cgctatttga cgcgcacgac agtcgcgggg gacaaacctt ctcgccatca ccatcatcat  900
cattag                                                             906
```

```
SEQ ID NO: 30          moltype = DNA  length = 888
FEATURE                Location/Qualifiers
source                 1..888
                       mol_type = other DNA
                       note = Recombinant
                       organism = synthetic construct
SEQUENCE: 30
atgcacgcgg cgctgactcc tctcaccaac aagtatcgct ttatcgacgt gcagccgctg  60
acaggcgtcc tcggtgcaga gattacaggc gtggatctgc gggagcctct cgatgacagc  120
acttggaatg agatcctgga cgcctttcac acctaccaag tgatctactt tccgggtcaa  180
gctatcacta acgagcagca catcgcgttc tcccgccggt tcggccctgt ggacccggtg  240
ccgctgttaa agagtatcga gggctatcca gaggtgcaga tgatacggcg cgaggcgaac  300
gagagcggcc gggtgatcgg agatgactgg cacaccgatt ccaccttcct ggacgctccg  360
cctgccgccg tggtgatgag agctatcgaa gtgccggagt atggaggtga cacaggcttc  420
ctctccatgt acagtgcctg ggagacactc tcgcctacga tgcaagctac catcgaaggc  480
ttaaacgtgg tccactcggc gacgaaggtc ttcgggtcat tgtaccaggc gactaattgg  540
cgcttctcga acaccagcgt gaaagtgatg gacgtggacg ccggagatag agagactgtg  600
cacccactcg tcgtgacgca tcctgttacg ggaaggcgcg cactctactg caaccaggtg  660
tactgccaga agatccaggg aatgacggac gcggagtcga agtccctgtt gcaattcctt  720
tacgagcacg ccaccaagtt cgacttcacc tgccgggtcc ggtggaagaa ggaccaagtc  780
ctggtgtggg acaacctgtg taccatgcac cgcgccgtcc cggactacgc tgggaaattc  840
agatacctga cccgcaccac cgtggcggga gacaagccgt cgcgttga               888
```

```
SEQ ID NO: 31          moltype = AA  length = 295
FEATURE                Location/Qualifiers
source                 1..295
                       mol_type = protein
                       note = Recombinant
                       organism = synthetic construct
SEQUENCE: 31
MHAALSPLSQ KYRFIDVQPL TGVLGAEITG VTLREPLDDN TWNEILDAFH TYQVIYFPGQ  60
AITNEQHIAF SRRFGPVDPV PLLKSIEGYP EVQMIRREAN ESGRVIGDDW HTDSTFLDAP  120
PAAVVMYARE VPPYGGDTGF LSMYSAWDTL SDTMKATIEG LNVVHSATRV FGSLYQAQNR  180
RFSNTSVKVM DVDAGDRETV HPLVVSHPVT GRRALYCNQV YCQRIEGMTD AESKPLLQFL  240
YEHATRFDFT CRVRWKKDQV LVWDNLCTMH RAVPDYAGKF RYLTRTTVAG DKPSR        295
```

```
SEQ ID NO: 32          moltype = DNA  length = 906
FEATURE                Location/Qualifiers
source                 1..906
                       mol_type = other DNA
                       note = Recombinant
                       organism = synthetic construct
SEQUENCE: 32
atgcacgcgg ctctgagccc gcttagccag aaataccgtt tcatcgacgt tcagccgctg  60
accggtgttt taggtgctga aatcaccggt gttaccctgc gtgaaccgct ggacgacaac  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgctgctca aatctatcga aggttacccg gaagttcaga tgatccgtcg cgaagcgaac  300
gaatctggtc gtgttattgg tgacgattgg cacaccgact ccaccttcct ggacgcgccg  360
ccagctgcag ttgtgatgta cgctcgtgaa gttccgccgt acggtggcga caccggtttc  420
ctgtccatgt actctgcttg ggacaccctg tccgacacca tgaaagctac cattgaaggt  480
ctgaacgttg tgcactccgc aacccgtgtg ttcggcagcc tgtaccaggc acagaaccgt  540
cgcttcagca acactagtgt gaaagtgatg gatgtggatg caggcgatcg tgagactgtg  600
cacccgctgg tggtatctca cccggttacc ggccgtcgtg cgctgtactg caaccaggta  660
tattgccagc gtattgaggg catgactgat gcagagtcaa aaccactgct ccaatttctg  720
tatgagcacg ccactcgttt tgattttact tgccgtgtcc gttggaaaaa ggatcaagta  780
ctggtatggg ataatctgtg tacgatgcac cgcgccgtac ctgattatgc cggcaaattt  840
cgctatttga cgcgcacgac agtcgcgggg gacaaacctt ctcgccatca ccatcatcat  900
cattag                                                             906
```

```
SEQ ID NO: 33          moltype = DNA  length = 888
FEATURE                Location/Qualifiers
source                 1..888
```

```
                        mol_type = other DNA
                        note = Recombinant
                        organism = synthetic construct
SEQUENCE: 33
atgcacgccg ccctctctcc tcttagccag aagtaccgat tcatcgacgt ccagccgctc  60
actggcgtac tgggcgctga gataacgggt gtgaccctga gggagccgct ggacgacaac  120
acttggaacg agatccttga cgccttccat acttatcaag ttatctactt tcctggacaa  180
gcgattacga atgagcagca catcgcgttc tcccggaggt tcgggccagt cgatccggtg  240
ccgctactca agtccatcga aggataccca gaagtccaga tgatccgtcg tgaggcaaac  300
gagtccggcc gggtcatcgg cgacgattgg cacaccgact ctaccttcct tgacgcgcct  360
ccggccgcag tggtcatgta cgcccgcgag gtgcctccct acggcggcga tacgggcttc  420
ctcagtatgt actctgcatg ggacacccta agcgacacca tgaaggccac catcgaaggt  480
ctgaacgtcg tgcactcggc aacacgagtc ttcggatcac tctaccaagc acagaatcgc  540
cgcttctcga acacctcggt taaggtgatg gacgtggatg cgggtgacag ggaaaccgtt  600
catcctctgg tggtctcgca tccggttacg ggacgccgcg ctctctactg caaccaggtg  660
tactgtcaaa ggatcgaagg aatgacagat gctgagagca agccgttgct ccaattcctc  720
tatgaacacg caacaaggtt cgacttcacc tgccgggttc gatggaagaa ggatcaagtg  780
ctagtctggg acaacctctg caccatgcac cgggccgtgc cggactatgc tgggaaattc  840
cgttacctga cccgcacgac cgtcgcggga gacaagccgt cgagatga              888

SEQ ID NO: 34           moltype = AA  length = 295
FEATURE                 Location/Qualifiers
source                  1..295
                        mol_type = protein
                        note = Recombinant
                        organism = synthetic construct
SEQUENCE: 34
MHAALTPLTN KYRFIDVQPL TGVLGAEITG VDLREPLDDS TWNEILDAFH TYQVIYFPGQ  60
AITNEQHIAF SRRFGPVDPV PLLKSIEGYP EVQMIRREAN ESGRVIGDDW HADSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATKFDFT CRVRWKKDQV LVWDNLCTMH RSVPDYAGKF RYLTRTTVAG DKPSR       295

SEQ ID NO: 35           moltype = DNA  length = 906
FEATURE                 Location/Qualifiers
source                  1..906
                        mol_type = other DNA
                        note = Recombinant
                        organism = synthetic construct
SEQUENCE: 35
atgcacgcgg ctctgacccc gcttaccaac aaataccgtt tcatcgacgt tcagccgctg  60
accggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgctgctca aatctatcga aggttacccg gaagttcaga tgatccgtcg cgaagcgaac  300
gaatctggtc gtgttattgg tgacgattgg cacgcggact ccaccttcct ggacgcgccg  360
ccagctgcag ttgtgatgcg tgctattgaa gttccggaat acggtggcga caccggtttc  420
ctgtccatgt actctgcttg ggaaaccctg tccccgacca tgcaggctac cattgaaggt  480
ctgaacgttg tgcactccgc aaccaaagtg ttcggcagcc tgtaccaggc aaccaactgg  540
cgcttcagca acactagtgt gaaagtgatg gatgtggatg caggcgatcg tgagactgtg  600
cacccgctgg tggtaactca cccggttacc ggccgtcgtg cgctgtactg caaccaggta  660
tattgccaga aaattcaggg catgactgat gcagagtcaa aatctctgct ccaatttctg  720
tatgagcacg ccactaaatt tgattttact tgccgtgtcc gttggaaaaa ggatcaagta  780
ctggtatggg ataatctgtg tacgatgcac cgcagcgtac ctgattatgc cggcaaattt  840
cgctatttga cgcgcacgac agtcgcgggg gacaaacctt ctcgccatca ccatcatcat  900
cattag                                                             906

SEQ ID NO: 36           moltype = DNA  length = 888
FEATURE                 Location/Qualifiers
source                  1..888
                        mol_type = other DNA
                        note = Recombinant
                        organism = synthetic construct
SEQUENCE: 36
atgcacgcgg cgctgactcc tctcaccaac aagtatcgct ttatcgacgt gcagccgctg  60
acaggcgtcc tcggtgcaga gattacaggc gtggatctgc gggagcctct cgatgacagc  120
acttggaatg agatcctgga cgcctttcac acctaccaag tgatctactt tccgggtcaa  180
gctatcacta acgagcagca catcgcgttc tcccgccggt tcggccctgt ggacccggtg  240
ccgctgttaa agagtatcga gggctatcca gaggtgcaga tgatacggcg cgaggcgaac  300
gagagcggcc gggtgatcgg agatgactgg cacgccgatt ccaccttcct ggacgctccg  360
cctgccgccg tggtgatgag agctatcgaa gtgccggagt atggaggtga cacaggcttc  420
ctctccatgt acagtgcctg ggagacactc tcgcctacga tgcaagctac catcgaaggc  480
ttaaacgtgg tccactcggc gacgaaggtc ttcgggtcat tgtaccaggc gactaattgg  540
cgcttctcga acaccagcgt gaaagtgatg gacgtggacg ccggagatag agagactgtg  600
cacccactcg tcgtgacgca tcctgttacg ggaaggcgcg cactctactg caaccaggtg  660
tactgccaga agatccaggg aatgacggac gcggagtcga agtccctgtt gcaattcctt  720
tacgagcacg ccaccaagtt cgacttcacc tgccgggtcc ggtggaagaa ggaccaagtc  780
ctggtgtggg acaacctgtg taccatgcac cgctccgtcc cggactacgc tgggaaattc  840
agatacctga cccgcaccac cgtggcggga gacaagccgt cgcgttga              888
```

```
SEQ ID NO: 37          moltype = AA  length = 295
FEATURE                Location/Qualifiers
source                 1..295
                       mol_type = protein
                       note = Recombinant
                       organism = synthetic construct
SEQUENCE: 37
MHAALTPLTN KYRFIDVQPL TGVLGAEITG VDLREPLDDS TWNEILDAFH TYQVIYFPGQ  60
AITNEQHIAF SRRFGPVDPV PILKSIEGYP EVQMIRREAN ESGRVIGDDW HTDSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATKFDFT CRVRWKKDQV LVWDNLCTMH RSVPDYGNAF RYLTRTTVAG DKPSR       295

SEQ ID NO: 38          moltype = DNA  length = 906
FEATURE                Location/Qualifiers
source                 1..906
                       mol_type = other DNA
                       note = Recombinant
                       organism = synthetic construct
SEQUENCE: 38
atgcacgcgg ctctgacccc gcttaccaac aaataccgtt tcatcgacgt tcagccgctg  60
accggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgattctca aatctatcga aggttacccg gaagttcaga tgatccgtcg cgaagcgaac  300
gaatctggtc gtgttattgg tgacgattgg cacaccgact ccaccttcct ggacgcgccg  360
ccagctgcag ttgtgatgcg tgctattgaa gttccggaat acggtggcga caccggtttc  420
ctgtccatgt actctgcttg ggaaaccctg tccccgacca tgcaggctac cattgaaggt  480
ctgaacgttg tgcactccgc aaccaaagtg ttcggcagcc tgtaccaggc aaccaactgg  540
cgcttcagca acactagtgt gaaagtgatg gatgtggatg caggcgatcg tgagactgtg  600
cacccgctgg tggtaactca cccggttacc ggccgtcgtg cgctgtactg caaccaggta  660
tattgccaga aaattcaggg catgactgat gcagagtcaa aatctctgct ccaatttctg  720
tatgagcacg ccactaaatt tgattttact tgccgtgtcc gttggaaaaa ggatcaagta  780
ctggtatggg ataatctgtg tacgatgcac cgcagcgtac ctgattatgg caatgcgttt  840
cgctatttga cgcgcacgac agtcgcgggg gacaaacctt ctcgccatca ccatcatcat  900
cattag                                                             906

SEQ ID NO: 39          moltype = DNA  length = 888
FEATURE                Location/Qualifiers
source                 1..888
                       mol_type = other DNA
                       note = Recombinant
                       organism = synthetic construct
SEQUENCE: 39
atgcacgcgg cgctgactcc tctcaccaac aagtatcgct ttatcgacgt gcagccgctg  60
acaggcgtcc tcggtgcaga gattacaggc gtggatctgc gggagcctct cgatgacagc  120
acttggaatg agatcctgga cgcctttcac acctaccaag tgatctactt tccgggtcaa  180
gctatcacta acgagcagca catcgcgttc tcccgccggt tcggccctgt ggacccggtg  240
ccgatcttaa agagtatcga gggctatcca gaggtgcaga tgatacggcg cgaggcgaac  300
gagagcggcc gggtgatcgg agatgactgg cacaccgatt ccaccttcct ggacgctccg  360
cctgccgccg tggtgatgag agctatcgaa gtgccggagt atggaggtga cacaggcttc  420
ctctccatgt acagtgcctg ggagacactc tcgcctacga tgcaagctac catcgaaggc  480
ttaaacgtgg tccactcggc gacgaaggtc ttcgggtcat tgtaccaggc gactaattgg  540
cgcttctcga acaccagcgt gaaagtgatg gacgtggacg ccggagatag agagactgtg  600
cacccactcg tcgtgacgca tcctgttacg ggaaggcgcg cactctactg caaccaggtg  660
tactgccaga agatccaggg aatgacggac gcggagtcga agtccctgtt gcaattcctt  720
tacgagcacg ccaccaagtt cgacttcacc tgccgggtcc ggtggaagaa ggaccaagtc  780
ctggtgtggg acaacctgtg taccatgcac cgctccgtcc cggactacgg caacgccttc  840
agatacctga cccgcaccac cgtggcggga gacaagccgt cgcgttga               888

SEQ ID NO: 40          moltype = AA  length = 295
FEATURE                Location/Qualifiers
source                 1..295
                       mol_type = protein
                       note = Recombinant
                       organism = synthetic construct
SEQUENCE: 40
MHAALTPLTN KYRFIDVQPL TGVLGAEITG VDLREPLDDS TWNEILDAFH TYQVIYFPAQ  60
QITNEQHISF SRRFGPVDPV PLLKSIEGYP EVQMIRREAN ESGRILGDDW HTDSTFLDAP  120
PAAVVMRAIE VPEYGGDTGF LSMYSAWDTL SDTMKATIEG LNVVHSATRV FGSLYQAQNW  180
RFSNTSVKVM DVDAGDRETV HPLVVSHPVT GRRALYCNQV YCQRIEGMTD AESKCLLQFL  240
YEHATKFDFT CRVRWKKDQV LVWDNLCTMH RAVPDYAGKF RYLTRTTVAG DRPAR       295

SEQ ID NO: 41          moltype = DNA  length = 906
FEATURE                Location/Qualifiers
source                 1..906
                       mol_type = other DNA
                       note = Recombinant
```

```
                        organism = synthetic construct
SEQUENCE: 41
atgcacgcgg ctctgacccc gcttaccaac aaataccgtt tcatcgacgt tcagccgctg  60
accggtgttt taggtgctga aatcaccggt gttgacctgc gtgaaccgct ggacgactct  120
acctggaacg aaatcctgga cgcgttccac acctaccagg ttatctactt cccggcgcag  180
cagatcacca acgaacagca catctctttc tctcgtcgct tcggtccggt tgacccggtt  240
ccgctgctca aatctatcga aggttacccg gaagttcaga tgatccgtcg cgaagcgaac  300
gaatctggtc gtatcctggg tgacgattgg cacaccgact ccaccttcct ggacgcgccg  360
ccagctgcag ttgtgatgcg tgctattgaa gttccggaat acggtggcga caccggtttc  420
ctgtccatgt actctgcttg ggacaccctg tccgacacca tgaaagctac cattgaaggt  480
ctgaacgttg tgcactccgc aacccgtgtg ttcggcagcc tgtaccaggc acagaactgg  540
cgcttcagca acactagtgt gaaagtgatg gatgtggatg caggcgatcg tgagactgtg  600
cacccgctgg tggtatctca cccggttacc ggccgtcgtg cgctgtactg caaccaggta  660
tattgccagc gtattgaggg catgactgat gcagagtcaa aatgcctgct ccaatttctg  720
tatgagcacg ccactaaatt tgattttact tgccgtgtcc gttggaaaaa ggatcaagta  780
ctggtatggg ataatctgtg tacgatgcac cgcgccgtac ctgattatgc cggcaaattt  840
cgctatttga cgcgcacgac agtcgcgggg gaccgccctg cccgccatca ccatcatcat  900
cattag                                                             906

SEQ ID NO: 42           moltype = DNA  length = 888
FEATURE                 Location/Qualifiers
source                  1..888
                        mol_type = other DNA
                        note = Recombinant
                        organism = synthetic construct
SEQUENCE: 42
atgcacgccg ccttaacgcc actcacgaac aagtatcgct tcatcgacgt ccagccgctc  60
actggcgtgc taggtgctga gatcaccggc gttgatctcc gcgagcctct tgacgactcg  120
acctggaacg agatcctgga tgccttccac acttaccaag tgatctactt cccggcccaa  180
cagatcacaa acgagcagca catctccttt agtaggcgat tcggtccagt cgatccggtg  240
ccgctcctca agtcgattga gggctacccg gaggtccaga tgattcgtag ggaagccaac  300
gagtcaggcc gtattctggg cgacgactgg catacggact ccactttcct agacgcacct  360
ccggctgccg tcgtcatgag ggctattgaa gtgccggagt acggcggcga taccggattc  420
ctctctatgt actccgcctg ggacacgctc tcagacacca tgaaggccac gatagagggc  480
ctgaacgttg tgcactccgc aacgagagta ttcggatctc tgtaccaggc acagaactgg  540
cggttcagta acacgagcgt gaaagtcatg gacgtggacg ctggcgacag ggaaactgtt  600
cacccgttgg tcgtttccca ccctgtcact ggtcgccggg cactttactg caaccaggtg  660
tactgtcagc gcattgaggg catgacggat gctgagtcga agtgccttct ccaattcttg  720
tacgagcacg cgacaaagtt cgatttcacg tgccgggtcc gatggaagaa ggaccaagtg  780
ctagtgtggg acaacctttg cacgatgcac cgcgctgtcc cggattacgc cggaaagttc  840
cgttacctca ccagaacaac agttgccggt gacagacccg cgagatga                888

SEQ ID NO: 43           moltype = AA  length = 295
FEATURE                 Location/Qualifiers
source                  1..295
                        mol_type = protein
                        note = Recombinant
                        organism = synthetic construct
SEQUENCE: 43
MHAALTPLTN KYRFIDVQPL CGVLGAEITG VDLREPLDDS TWNEILDAFH TYQVIYFPGQ  60
AITNEQHIAF SRRFGPVDPV PLLKSIEGYP EVQMIRREAN ESGRILGDDW HTDSTFLDAP  120
PAAVVMRAIE VPEYGGDTGF LSMYSAWDTL SDTMKATIEG LNVVHSATRV FGSLYQAQNW  180
RFSNTSVKVM DVDAGDRETV HPLVVSHPVT GRRALYCNQV YCQRIEGMTD AESKCLLQFL  240
YEHATKFDFT CRVRWKKDQV LVWDNLCTMH LAVPDYDGKF RYLTRTTVAG DKPSR        295

SEQ ID NO: 44           moltype = DNA  length = 906
FEATURE                 Location/Qualifiers
source                  1..906
                        mol_type = other DNA
                        note = Recombinant
                        organism = synthetic construct
SEQUENCE: 44
atgcacgcgg ctctgacccc gcttaccaac aaataccgtt tcatcgacgt tcagccgctg  60
tgcggtgttt taggtgctga aatcaccggt gttgacctgc gtgaaccgct ggacgactct  120
acctggaacg aaatcctgga cgcgttccac acctaccagg ttatctactt cccgggtcag  180
gcgatcacca acgaacagca catcgcgttc tctcgtcgct tcggtccggt tgacccggtt  240
ccgctgctca aatctatcga aggttacccg gaagttcaga tgatccgtcg cgaagcgaac  300
gaatctggtc gtatcctggg tgacgattgg cacaccgact ccaccttcct ggacgcgccg  360
ccagctgcag ttgtgatgcg tgctattgaa gttccggaat acggtggcga caccggtttc  420
ctgtccatgt actctgcttg ggacaccctg tccgacacca tgaaagctac cattgaaggt  480
ctgaacgttg tgcactccgc aacccgtgtg ttcggcagcc tgtaccaggc acagaactgg  540
cgcttcagca acactagtgt gaaagtgatg gatgtggatg caggcgatcg tgagactgtg  600
cacccgctgg tggtatctca cccggttacc ggccgtcgtg cgctgtactg caaccaggta  660
tattgccagc gtattgaggg catgactgat gcagagtcaa aatgcctgct ccaatttctg  720
tatgagcacg ccactaaatt tgattttact tgccgtgtcc gttggaaaaa ggatcaagta  780
ctggtatggg ataatctgtg tacgatgcac ctggccgtac ctgattatga cggcaaattt  840
cgctatttga cgcgcacgac agtcgcgggg gacaaacctt ctcgccatca ccatcatcat  900
cattag                                                             906
```

```
SEQ ID NO: 45          moltype = DNA  length = 888
FEATURE                Location/Qualifiers
source                 1..888
                       mol_type = other DNA
                       note = Recombinant
                       organism = synthetic construct
SEQUENCE: 45
atgcacgcgg ctctcacacc gctcacaaac aagtaccgct tcattgacgt gcagccgctg  60
tgtggcgtcc tgggcgcaga aatcacgggc gtggatctcc gcgagcctct ggacgacagc  120
acctggaacg aaatcctgga tgctttccac acttaccaag tgatctactt tcccggacaa  180
gccatcacta acgagcagca catcgctttc tcacggcgct tcggcccggt agatccggtg  240
ccgctactca agtcaattga aggctatccg gaggtgcaaa tgattcgccg cgaagctaac  300
gagagcgggc gcatactggg cgacgactgg catactgact ccaccttcct cgatgctcca  360
ccagccgcag tggtgatgcg tgccatcgaa gttcccgagt atggtggcga cacgggtttc  420
ctgtctatgt actccgcttg ggatacactg tctgacacga tgaaggctac catcgagggc  480
ctgaatgtcg tccacagtgc tacgcgcgtg ttcggctcac tgtaccaggc gcagaactgg  540
aggttcagca acaccagtgt caaggtgatg gacgttgatg ctggagacag ggaaactgtg  600
catcctcttg tggtctccca tccagttacc gggaggagag cactctactg caaccaggtt  660
tactgccagc gcatcgaggg catgaccgat gcggagtcga agtgtctgtt acagttcttg  720
tacgagcacg cgacgaagtt cgacttcacg tgccgggtgc ggtggaagaa ggaccaagtt  780
ctcgtctggg acaatctctg cacgatgcac ctcgccgttc ccgactacga cggcaaattc  840
agatacttga cccgaacaac agtagcggga gataagcctt cccgttga                888

SEQ ID NO: 46          moltype = AA  length = 295
FEATURE                Location/Qualifiers
source                 1..295
                       mol_type = protein
                       note = Recombinant
                       organism = synthetic construct
SEQUENCE: 46
MHAALTPLTN KYRFIDVQPL TGVLGAEITG VDLREPLDDS TWNEILDAFH TYQVIYFPGQ  60
AITNEQHIAF SRRFGPVDPV PILKSIEGYP EVQMIRREAN ESSRYIGDDW HADSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATKFDFT CRVRWKKDQV LVWDNLCTMH RAVPDYAGKF RYLTRTTVAG DKPSR       295

SEQ ID NO: 47          moltype = AA  length = 295
FEATURE                Location/Qualifiers
source                 1..295
                       mol_type = protein
                       note = Recombinant
                       organism = synthetic construct
SEQUENCE: 47
MHAALTPLTN KYRFIDVQPL TGVLGAEITG VDLREPLDDS TWNEILDAFH TYQVIYFPGQ  60
AITNEQHIAF SRRFGPVDPV PILKSIEGYP EVQMIRREAN ESSRYIGDDW HADSTFLDAP  120
PAAVVMRAIE VPEYGGDTGF LSMYSAWETL SPTMQATIEG LNVVHSATKV FGSLYQATNW  180
RFSGTSVKVM DVDAGDRETV HPLVVTHPVT GRRALYCNQV YCQKIQGMTD AESKSLLQFL  240
YEHATQFDFT CRVRWKKDQV LVWDNLCTMH RAVPDYAGKF RYLTRTTVAG DKPSR       295

SEQ ID NO: 48          moltype = AA  length = 295
FEATURE                Location/Qualifiers
source                 1..295
                       mol_type = protein
                       note = Recombinant
                       organism = synthetic construct
SEQUENCE: 48
MHAALTPLTN KYRHIDVQPL TGVLGAEITG VDLREPLDDS TWNEILDAFH TYQVIYFPGQ  60
AITNEQHIAF SRRFGPVDPV PILKSIEGYP EVQMIRREAN ESSRYIGDDW HADSTFLDAP  120
PAAVVMRAIE VPEYGGDTGF LSMYSAWETL SPTMQATIEG LNVVHSATKV FGSLYQATNW  180
RFSGTSVKVM DVDAGDRETV HPLVVTHPVT GRRALYCNQV YCQKIQGMTD AESKSLLQFL  240
YEHATQFDFT CRVRWKKDQV LVWDNLCTMH RAVPDYAGKF RYLTRTTVAG DKPSR       295

SEQ ID NO: 49          moltype = AA  length = 295
FEATURE                Location/Qualifiers
source                 1..295
                       mol_type = protein
                       note = Recombinant
                       organism = synthetic construct
SEQUENCE: 49
MHAALTPLTN KYRHIDVQPL TGVLGAEITG VDLREPLDDS TWNEILDAFH TYQVIYFPGQ  60
AITNEQHIAF SRRFGPVDPV PILKSIEGYP EVQMIRREAN ESSRYIGDDW HADSTFLDAP  120
PAAVVMRAIE VPEYGGDTGF LSMYSAWETL SPAMQATIEG LNVVHSATKV FGSLYQATNW  180
RFSNTSVKVM DVDAGDRETV HPLVVTHPVT GRRALYCNQI YCQKIQGMTD AESKSLLQFL  240
YEHATQFDFT CRVRWKKDQV LVWDNLCTMH RAVPDYAGKF RYLTRTTVAG DKPSR       295

SEQ ID NO: 50          moltype = AA  length = 295
FEATURE                Location/Qualifiers
source                 1..295
                       mol_type = protein
```

```
                          note = Recombinant
                          organism = synthetic construct
SEQUENCE: 50
MHAALTPLTN KYRFIDVQPL TGVLGAEITG VDLREPLDDS TWNEILDAFH TYQVIYFPGQ  60
AITNEQHIAF SRRFGPVDPV PILKSIEGYP EVQMIRREAN ESSRYIGDDW HADSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQI YCQKIQGMTD AESKSLLQFL  240
YEHATQFDFT CRVRWKKDQV LVWDNLCTMH RAVPDYAGKF RYLTRTTVAG DKPSR       295

SEQ ID NO: 51             moltype = AA  length = 295
FEATURE                   Location/Qualifiers
source                    1..295
                          mol_type = protein
                          note = Recombinant
                          organism = synthetic construct
SEQUENCE: 51
MHAALTPLTN KYRFIDVQPL TGVLGAEITG VDLREPLDDS TWNEILDAFH TYQVIYFPGQ  60
AITNEQHIAF SRRFGPVDPV PILKSIEGYP EVQMIRREAN ESSRYIGDDW HADSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATQFDFT CRVRWKKDQV LVWDNLCTMH RAVPDYAGKF RYLTRTTVAG DKPSR       295

SEQ ID NO: 52             moltype = AA  length = 295
FEATURE                   Location/Qualifiers
source                    1..295
                          mol_type = protein
                          note = Recombinant
                          organism = synthetic construct
SEQUENCE: 52
MHAALTPLTN KYRHIDVQPL TGVLGAEITG VDLREPLDDS TWNEILDAFH TYQVIYFPGQ  60
AITNEQHIAF SRRFGPVDPV PILKSIEGYP EVQMIRREAN ESSRYIGDDW HADSTFLDAP  120
PAAVVMRAIE VPEYGGDTGF LSMYSAWETL SPTMQATIEG LNVVHSATKV FGSLYQATNW  180
RFSNTSVKVM DVDAGDRETV HPLVVTHPVT GRRALYCNQV YCQKIQGMTD AESKSLLQFL  240
YEHATQFDFT CRVRWKKDQV LVWDNLCTMH RAVPDYAGKF RYLTRTTVAG DKPSR       295

SEQ ID NO: 53             moltype = DNA  length = 888
FEATURE                   Location/Qualifiers
source                    1..888
                          mol_type = other DNA
                          note = Recombinant
                          organism = synthetic construct
SEQUENCE: 53
atgcacgcgg ctttgacacc tttgaccaac aagtatcggt tcatcgacgt tcaaccactc  60
acaggcgtgc tcggcgcaga gattaccgga gtggacctga gggagccctt agacgactcc  120
acttggaacg agatcctcga cgcctttcac acctaccaag ttatctactt tcctggacag  180
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggtacatagg cgacgattgg cacgcagaca gcaccttcct tgacgctcct  360
ccggctgccg tggttatgcg cgcaatagag gtgccggagt acggcggcga taccggtttc  420
ctatcaatgt actctgcatg ggagacgctc tcaccaacga tgcaagccac cattgaaggt  480
ctaaacgtgg ttcactcagc tactaaggtc ttcggaagtc tttaccaggc gacgaattgg  540
aggttcagta acaccagtgt gaaggtgatg gatgtggacg ctggagacag ggagacggtg  600
catccactcg tagttacaca ccctgtaact ggacgcagag ccctttactg caaccaggtt  660
tactgccaga agatccaggg aatgactgat gcggagtcta agtccctgct tcaattcctc  720
tacgaacacg ccaccaaatt cgacttcact tgtcgtgttc ggtggaagaa ggaccaagtg  780
ctcgtgtggg ataacctttg caccatgcac cgagcagtac cagactacgc cgggaaattc  840
cgctatctca cccgcactac agtggccgga gacaagccta gccgctga              888

SEQ ID NO: 54             moltype = DNA  length = 888
FEATURE                   Location/Qualifiers
source                    1..888
                          mol_type = other DNA
                          note = Recombinant
                          organism = synthetic construct
SEQUENCE: 54
atgcacgcgg ctttgacacc tttgaccaac aagtatcggt tcatcgacgt tcaaccactc  60
acaggcgtgc tcggcgcaga gattaccgga gtggacctga gggagccctt agacgactcc  120
acttggaacg agatcctcga cgcctttcac acctaccaag ttatctactt tcctggacag  180
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggtacatagg cgacgattgg cacgcagaca gcaccttcct tgacgctcct  360
ccggctgccg tggttatgcg cgcaatagag gtgccggagt acggcggcga taccggtttc  420
ctatcaatgt actctgcatg ggagacgctc tcaccaacga tgcaagccac cattgaaggt  480
ctaaacgtgg ttcactcagc tactaaggtc ttcggaagtc tttaccaggc gacgaattgg  540
aggttcagtg gaaccagtgt gaaggtgatg gatgtggacg ctggagacag ggagacggtg  600
catccactcg tagttacaca ccctgtaact ggacgcagag ccctttactg caaccaggtt  660
tactgccaga agatccaggg aatgactgat gcggagtcta agtccctgct tcaattcctc  720
tacgaacacg ccacccaatt cgacttcact tgtcgtgttc ggtggaagaa ggaccaagtg  780
ctcgtgtggg ataacctttg caccatgcac cgagcagtac cagactacgc cgggaaattc  840
```

```
cgctatctca cccgcactac agtggccgga gacaagccta gccgctga              888

SEQ ID NO: 55          moltype = DNA  length = 888
FEATURE                Location/Qualifiers
source                 1..888
                       mol_type = other DNA
                       note = Recombinant
                       organism = synthetic construct
SEQUENCE: 55
atgcacgcgg ctttgacacc tttgaccaac aagtatcggc atatcgacgt tcaaccactc  60
acaggcgtgc tcggcgcaga gattaccgga gtggacctga gggagccctt agacgactcc  120
acttggaacg agatcctcga cgcctttcac acctaccaag ttatctactt tcctggacag  180
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggtacatagg cgacgattgg cacgcagaca gcaccttcct tgacgctcct  360
ccggctgccg tggttatgcg cgcaatagag gtgccggagt acggcggcga taccggtttc  420
ctatcaatgt actctgcatg ggagacgctc tcaccaacga tgcaagccac cattgaaggt  480
ctaaacgtgg ttcactcagc tactaaggtc ttcggaagtc tttaccaggc gacgaattgg  540
aggttcagtg gaaccagtgt gaaggtgatg gatgtggacg ctggagacag ggagacggtg  600
catccactcg tagttacaca ccctgtaact ggacgcagag ccctttactg caaccaggtt  660
tactgccaga agatccaggg aatgactgat gcggagtcta agtccctgct tcaattcctc  720
tacgaacacg ccacccaatt cgacttcact tgtcgtgttc ggtggaagaa ggaccaagtg  780
ctcgtgtggg ataacctttg caccatgcac cgagcagtac cagactacgc cgggaaattc  840
cgctatctca cccgcactac agtggccgga gacaagccta gccgctga              888

SEQ ID NO: 56          moltype = DNA  length = 888
FEATURE                Location/Qualifiers
source                 1..888
                       mol_type = other DNA
                       note = Recombinant
                       organism = synthetic construct
SEQUENCE: 56
atgcacgcgg ctttgacacc tttgaccaac aagtatcggc atatcgacgt tcaaccactc  60
acaggcgtgc tcggcgcaga gattaccgga gtggacctga gggagccctt agacgactcc  120
acttggaacg agatcctcga cgcctttcac acctaccaag ttatctactt tcctggacag  180
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggtacatagg cgacgattgg cacgcagaca gcaccttcct tgacgctcct  360
ccggctgccg tggttatgcg cgcaatagag gtgccggagt acggcggcga taccggtttc  420
ctatcaatgt actctgcatg ggagacgctc tcaccagcta tgcaagccac cattgaaggt  480
ctaaacgtgg ttcactcagc tactaaggtc ttcggaagtc tttaccaggc gacgaattgg  540
aggttcagta acaccagtgt gaaggtgatg gatgtggacg ctggagacag ggagacggtg  600
catccactcg tagttacaca ccctgtaact ggacgcagag ccctttactg caaccagatt  660
tactgccaga agatccaggg aatgactgat gcggagtcta agtccctgct tcaattcctc  720
tacgaacacg ccacccaatt cgacttcact tgtcgtgttc ggtggaagaa ggaccaagtg  780
ctcgtgtggg ataacctttg caccatgcac cgagcagtac cagactacgc cgggaaattc  840
cgctatctca cccgcactac agtggccgga gacaagccta gccgctga              888

SEQ ID NO: 57          moltype = DNA  length = 888
FEATURE                Location/Qualifiers
source                 1..888
                       mol_type = other DNA
                       note = Recombinant
                       organism = synthetic construct
SEQUENCE: 57
atgcacgcgg ctttgacacc tttgaccaac aagtatcggt tcatcgacgt tcaaccactc  60
acaggcgtgc tcggcgcaga gattaccgga gtggacctga gggagccctt agacgactcc  120
acttggaacg agatcctcga cgcctttcac acctaccaag ttatctactt tcctggacag  180
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggtacatagg cgacgattgg cacgcagaca gcaccttcct tgacgctcct  360
ccggctgccg tggttatgcg cgcaatagag gtgccggagt acggcggcga taccggtttc  420
ctatcaatgt actctgcatg ggagacgctc tcaccaacga tgcaagccac cattgaaggt  480
ctaaacgtgg ttcactcagc tactaaggtc ttcggaagtc tttaccaggc gacgaattgg  540
aggttcagta acaccagtgt gaaggtgatg gatgtggacg ctggagacag ggagacggtg  600
catccactcg tagttacaca ccctgtaact ggacgcagag ccctttactg caaccagatt  660
tactgccaga agatccaggg aatgactgat gcggagtcta agtccctgct tcaattcctc  720
tacgaacacg ccacccaatt cgacttcact tgtcgtgttc ggtggaagaa ggaccaagtg  780
ctcgtgtggg ataacctttg caccatgcac cgagcagtac cagactacgc cgggaaattc  840
cgctatctca cccgcactac agtggccgga gacaagccta gccgctga              888

SEQ ID NO: 58          moltype = DNA  length = 888
FEATURE                Location/Qualifiers
source                 1..888
                       mol_type = other DNA
                       note = Recombinant
                       organism = synthetic construct
SEQUENCE: 58
atgcacgcgg ctttgacacc tttgaccaac aagtatcggt tcatcgacgt tcaaccactc  60
```

```
acaggcgtgc tcggcgcaga gattaccgga gtggacctga gggagccctt agacgactcc  120
acttggaacg agatcctcga cgcctttcac acctaccaag ttatctactt tcctggacag  180
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggtacatagg cgacgattgg cacgcagaca gcaccttcct tgacgctcct  360
ccggctgccg tggttatgcg cgcaatagag gtgccggagt acggcggcga taccggtttc  420
ctatcaatgt actctgcatg ggagacgctc tcaccaacga tgcaagccac cattgaaggt  480
ctaaacgtgg ttcactcagc tactaaggtc ttcggaagtc tttaccaggc gacgaattgg  540
aggttcagta acaccagtgt gaaggtgatg gatgtggacg ctggagacag ggagacggtg  600
catccactcg tagttacaca ccctgtaact ggacgcagag ccctttactg caaccaggtt  660
tactgccaga agatccaggg aatgactgat gcggagtcta agtccctgct tcaattcctc  720
tacgaacacg ccacccaatt cgacttcact tgtcgtgttc ggtggaagaa ggaccaagtg  780
ctcgtgtggg ataacctttg caccatgcac cgagcagtac cagactacgc cgggaaattc  840
cgctatctca cccgcactac agtggccgga gacaagccta gccgctga               888

SEQ ID NO: 59          moltype = DNA  length = 888
FEATURE                Location/Qualifiers
source                 1..888
                       mol_type = other DNA
                       note = Recombinant
                       organism = synthetic construct
SEQUENCE: 59
atgcacgcgg ctttgacacc tttgaccaac aagtatcggc atatcgacgt tcaaccactc  60
acaggcgtgc tcggcgcaga gattaccgga gtggacctga gggagccctt agacgactcc  120
acttggaacg agatcctcga cgcctttcac acctaccaag ttatctactt tcctggacag  180
gcgatcacca acgagcagca cattgccttc tcaaggaggt tcggaccggt agatccagtt  240
ccaattctca aatccattga gggttatccc gaggtgcaga tgattagacg agaagccaac  300
gagtcctcac ggtacatagg cgacgattgg cacgcagaca gcaccttcct tgacgctcct  360
ccggctgccg tggttatgcg cgcaatagag gtgccggagt acggcggcga taccggtttc  420
ctatcaatgt actctgcatg ggagacgctc tcaccaacga tgcaagccac cattgaaggt  480
ctaaacgtgg ttcactcagc tactaaggtc ttcggaagtc tttaccaggc gacgaattgg  540
aggttcagta acaccagtgt gaaggtgatg gatgtggacg ctggagacag ggagacggtg  600
catccactcg tagttacaca ccctgtaact ggacgcagag ccctttactg caaccaggtt  660
tactgccaga agatccaggg aatgactgat gcggagtcta agtccctgct tcaattcctc  720
tacgaacacg ccacccaatt cgacttcact tgtcgtgttc ggtggaagaa ggaccaagtg  780
ctcgtgtggg ataacctttg caccatgcac cgagcagtac cagactacgc cgggaaattc  840
cgctatctca cccgcactac agtggccgga gacaagccta gccgctga               888

SEQ ID NO: 60          moltype = AA  length = 295
FEATURE                Location/Qualifiers
source                 1..295
                       mol_type = protein
                       organism = Sphingobium herbicidovorans
SEQUENCE: 60
MHAALSPLSQ RFERIAVQPL TGVLGAEITG VDLREPLDDS TWNEILDAFH TYQVIYFPGQ  60
AITNEQHIAF SRRFGPVDPV PLLKSIEGYP EVQMIRREAN ESGRVIGDDW HTDSTFLDAP  120
PAAVVMRAID VPEHGGDTGF LSMYTAWETL SPTMQATIEG LNVVHSATRV FGSLYQAQNR  180
RFSNTSVKVM DVDAGDRETV HPLVVTHPGS GRKGLYVNQV YCQRIEGMTD AESKPLLQFL  240
YEHATRFDFT CRVRWKKDQV LVWDNLCTMH RAVPDYAGKF RYLTRTTVGG VRPAR       295

SEQ ID NO: 61          moltype = AA  length = 295
FEATURE                Location/Qualifiers
VARIANT                6
                       note = X can be any naturally occurring amino acid
VARIANT                9..14
                       note = X can be any naturally occurring amino acid
VARIANT                16
                       note = X can be any naturally occurring amino acid
VARIANT                21
                       note = Thr can be Cys
VARIANT                32
                       note = Asp can be Thr
VARIANT                38
                       note = Asp can be Ser
VARIANT                40
                       note = Ser can be Asn
VARIANT                59
                       note = Gly can be Ala
VARIANT                61
                       note = Ala can be Gln
VARIANT                67
                       note = His can be Gln
VARIANT                69
                       note = Ala can be Ser
VARIANT                82
                       note = X can be any naturally occurring amino acid
VARIANT                103
                       note = X can be any naturally occurring amino acid
VARIANT                105
```

```
                        note = X can be any naturally occurring amino acid
VARIANT                 106
                        note = Ile can be Leu
VARIANT                 108
                        note = Asp can be Glu
VARIANT                 112
                        note = X can be any naturally occurring amino acid
VARIANT                 115
                        note = Thr can be Ser
VARIANT                 127
                        note = Arg can be Tyr
VARIANT                 129
                        note = Ile can be Arg or Lys
VARIANT                 130
                        note = Glu can be Asp
VARIANT                 131
                        note = Val can be Ile
VARIANT                 133
                        note = Glu can be Pro
VARIANT                 134
                        note = Tyr can be His
VARIANT                 139
                        note = Gly can be Leu
VARIANT                 145
                        note = X can be any naturally occurring amino acid
VARIANT                 147
                        note = Trp can be Tyr
VARIANT                 148
                        note = X can be any naturally occurring amino acid
VARIANT                 149
                        note = Thr can be Ala
VARIANT                 152
                        note = X can be any naturally occurring amino acid
VARIANT                 153
                        note = Thr can be Gly or Ala
VARIANT                 154
                        note = Met can be Leu
VARIANT                 156
                        note = Ala can be Lys
VARIANT                 157
                        note = Thr can be Leu
VARIANT                 159
                        note = Glu can be Ser
VARIANT                 169
                        note = X can be any naturally occurring amino acid
VARIANT                 178
                        note = X can be any naturally occurring amino acid
VARIANT                 180
                        note = X can be any naturally occurring amino acid
VARIANT                 182
                        note = Phe can be Tyr
VARIANT                 184
                        note = Asn can be Gly
VARIANT                 193
                        note = Asp can be Ala
VARIANT                 194
                        note = Ala can be Asp
VARIANT                 206
                        note = Thr can be Ser
VARIANT                 209
                        note = X can be any naturally occurring amino acid
VARIANT                 210
                        note = Thr can be Ser
VARIANT                 213..214
                        note = X can be any naturally occurring amino acid
VARIANT                 220
                        note = Val can be Ile
VARIANT                 224
                        note = X can be any naturally occurring amino acid
VARIANT                 226
                        note = X can be any naturally occurring amino acid
VARIANT                 229
                        note = Thr can be Ser
VARIANT                 230
                        note = Asp can be Glu
VARIANT                 231
                        note = Ala can be Lys
VARIANT                 234
                        note = Lys can be Glu
```

-continued

```
VARIANT                 235
                        note = X can be any naturally occurring amino acid
VARIANT                 238
                        note = Gln can be Ser
VARIANT                 241
                        note = Tyr can be Phe
VARIANT                 242
                        note = Glu can be Ala
VARIANT                 246
                        note = X can be any naturally occurring amino acid
VARIANT                 247
                        note = Phe can be Pro
VARIANT                 257
                        note = Lys can be Glu
VARIANT                 259
                        note = Gln can be Asp
VARIANT                 269
                        note = Met can be Gln
VARIANT                 271
                        note = X can be any naturally occurring amino acid
VARIANT                 272
                        note = Ala can be Ser
VARIANT                 273
                        note = Val can be Ala or Ile
VARIANT                 277
                        note = Ala can be Asp or Gly or His
VARIANT                 278
                        note = Gly can be Asn
VARIANT                 279
                        note = Lys can be Ala or Gln
VARIANT                 280
                        note = Phe can be Thr
VARIANT                 282
                        note = Tyr can be Ile
VARIANT                 284
                        note = Thr can be His
VARIANT                 294
                        note = X can be any naturally occurring amino acid
source                  1..295
                        mol_type = protein
                        note = consensus sequence
                        organism = synthetic construct
VARIANT                 291..292
                        note = X can be any naturally occurring amino acid
VARIANT                 274
                        note = Pro can be Asn
VARIANT                 256
                        note = Lys can be Gln
VARIANT                 248
                        note = Asp can be Glu
VARIANT                 217
                        note = X can be any naturally occurring amino acid
VARIANT                 289
                        note = X can be any naturally occurring amino acid
VARIANT                 141
                        note = Leu can be Thr or Ala
VARIANT                 109
                        note = Asp can be Asn
VARIANT                 155
                        note = X can be any naturally occurring amino acid
VARIANT                 258
                        note = Asp can be Gly
SEQUENCE: 61
MHAALXPLXX XXXXIXVQPL TGVLGAEITG VDLREPLDDS TWNEILDAFH TYQVIYFPGQ  60
AITNEQHIAF SRRFGPVDPV PXLKSIEGYP EVQMIRREAN ESXRXIGDDW HXDSTFLDAP  120
PAAVVMRAIE VPEYGGDTGF LSMYXAWXTL SXTMXATIEG LNVVHSATXV FGSLYQAXNX  180
RFSNTSVKVM DVDAGDRETV HPLVVTHPXT GRXXLYXNQV YCQXIXGMTD AESKXLLQFL  240
YEHATXFDFT CRVRWKKDQV LVWDNLCTMH XAVPDYAGKF RYLTRTTVXG XXPXR       295
```

HERBICIDE TOLERANCE GENES AND METHODS OF USE THEREOF

CROSS REFERENCE TO RELATED APPLICATIONS

This application is a continuation of U.S. patent application Ser. No. 18/301,106, filed Apr. 14, 2023, which is a continuation of U.S. patent application Ser. No. 17/150,604, filed Jan. 15, 2021, now U.S. Pat. No. 11,655,480, which is a continuation of U.S. patent application Ser. No. 16/016,364, filed Jun. 22, 2018, now U.S. Pat. No. 10,900,050, which is a continuation of U.S. patent application Ser. No. 14/871,768, filed Sep. 30, 2015, now U.S. Pat. No. 10,023,874, which claims the benefit of U.S. Provisional Patent Application No. 62/064,343, filed on Oct. 15, 2014, each of which is herein incorporated by reference in its entirety.

INCORPORATION OF SEQUENCE LISTING

The sequence listing that is contained in the file named "MONS378USC4_ST26.xml", which is 135,357 bytes (measured in MS-WINDOWS®) and created on Jun. 13, 2024, is filed herewith by electronic submission and incorporated herein by reference.

BACKGROUND OF THE INVENTION

Field of the Invention

The present invention generally relates to the field of biotechnology. More specifically, the invention relates to recombinant DNA molecules encoding enzymes that degrade herbicides. The invention also relates to transgenic plants, parts, seeds, cells, and plant parts containing the recombinant DNA molecules, as well as methods of using the same.

Description of Related Art

Agricultural crop production often utilizes transgenic traits created using the methods of biotechnology. A heterologous gene, also known as a transgene, is introduced into a plant to produce a transgenic trait. Expression of the transgene in the plant confers a desirable trait, such as herbicide tolerance, on the plant. Examples of transgenic herbicide tolerance traits include glyphosate tolerance, glufosinate tolerance, and dicamba tolerance. With the increase of weed species resistant to the most commonly used herbicides, new herbicide tolerance traits are needed in the field. Herbicides of particular interest are the aryloxyphenoxypropionate (AOPP) herbicides, phenoxy acid herbicides, and pyridinyloxy acid herbicides. AOPP herbicides, phenoxy acid herbicides, and pyridinyloxy acid herbicides provide control of a spectrum of glyphosate-resistant weeds, thus making a trait conferring tolerance these herbicides particularly useful in a cropping system combined with other herbicide tolerance trait(s).

The *Sphingobium herbicidovorans* strain MH isolated from a dichloroprop-degrading soil sample was identified as being capable of cleaving the ether bond of various phyenoxyalkanoic acid herbicides, utilizing this as its sole carbon and energy source for growth (HPE Kohler, Journal of Industrial Microbiology & Biotechnology (1999) 23:336-340). Catabolismof the herbicides is carried out by two different enantioselective alpha-ketoglutarate-dependent dioxygenases, RdpA (R-dichloroprop dioxygenase) and SdpA (S-dichloroprop dioxygenasc). (A Westendorf, et al., Microbiological Rescarch (2002) 157:317-322; Westendorf, et al., Acta Biotechnologica (2003) 23 (1): 3-17). RdpA has been isolated from *Sphingobium herbicidovorans* (GenBank Accessions AF516752 (DNA) and AAM90965 (protein)) and *Delftia acidovorans* (GenBank Accessions NG_036924 (DNA) and YP_009083283 (protein)) (TA Mueller, et al., Applied and Environmental Microbiology (2004) 70 (10): 6066-6075. ) The RdpA and SdpA genes have been used for plant transformation to confer herbicide tolerance to crops (TR Wright, et al., Proceedings of the National Academy of Sciences USA, (2010) 107 (47): 20240-5). Improving the activity of the RdpA enzyme using protein engineering techniques to create a protein for use in transgenic plants would permit higher rates of herbicide application, thus improving transgenic crop safety and weed control measures.

BRIEF SUMMARY OF THE INVENTION

The invention provides a polypeptide that has at least about 92% sequence identity to an amino acid sequence selected from the group consisting of SEQ ID NO:1, 4, 7, 9, 11, 14, 18, 22, 25, 28, 31, 34, 37, 40, 43, and 46-52. In one embodiment, the polypeptide has oxygenase activity against at least one herbicide selected from the group consisting of AOPP herbicides, phenoxy acid herbicides, and pyridinyloxy acid herbicides.

The invention provides a recombinant DNA molecule comprising a nucleic acid sequence encoding a polypeptide that has at least about 92% sequence identity to an amino acid sequence selected from the group consisting of SEQ ID NO: 1, 4, 7, 9, 11, 14, 18, 22, 25, 28, 31, 34, 37, 40, 43, and 46-52. In one embodiment, the recombinant DNA molecule comprises a nucleic acid sequence selected from the group consisting of SEQ ID NO:2, 3, 5, 6, 8, 10, 12, 13, 15, 16, 17, 18, 19, 20, 21, 23, 24, 26, 27, 29, 30, 32, 33, 35, 36, 38, 39, 41, 42, 44, 45, and 53-59. In another embodiment, the recombinant DNA molecule encodes a polypeptide with oxygenase activity against at least one herbicide selected from the group consisting of AOPP herbicides, phenoxy acid herbicides, and pyridinyloxy acid herbicides. In another embodiment, the recombinant DNA molecule is operably linked to a heterologous promoter functional in a plant cell. In another embodiment, the recombinant DNA molecule is operably linked to a DNA molecule encoding a chloroplast transit peptide that functions to localize an operably linked polypeptide within a cell.

The invention provides a DNA construct comprising a heterologous promoter functional in a plant cell operably linked to a recombinant DNA molecule comprising a nucleic acid sequence encoding a polypeptide that has at least about 92% sequence identity to an amino acid sequence selected from the group consisting of SEQ ID NO: 1, 4, 7, 9, 11, 14, 18, 22, 25, 28, 31, 34, 37, 40, 43, and 46-52. In one embodiment, the recombinant DNA molecule is operably linked to a DNA molecule encoding a chloroplast transit peptide that functions to localize an operably linked polypeptide within a cell. In another embodiment, the recombinant DNA molecule encodes a polypeptide that has an amino acid sequence selected from the group consisting of SEQ ID NO:1, 4, 7, 9, 11, 14, 18, 22, 25, 28, 31, 34, 37, 40, 43, and 46-52 and the expression of the polypeptide in a transgenic plant confers herbicide tolerance to the plant. In another embodiment, the DNA construct is present in the genome of a transgenic plant.

The invention provides a transgenic plant, seed, cell, or plant part comprising a recombinant DNA molecule comprising a nucleic acid sequence encoding a polypeptide that has at least about 92% sequence identity to an amino acid sequence selected from the group consisting of SEQ ID NO: 1, 4, 7, 9, 11, 14, 18, 22, 25, 28, 31, 34, 37, 40, 43, and 46-52. In one embodiment, the transgenic plant, seed, cell, or plant part comprises a transgenic trait for tolerance to at least one herbicide selected from the group consisting of AOPP herbicides, phenoxy acid herbicides, and pyridinyloxy acid herbicides. In another embodiment, the transgenic plant, seed, cell, or plant part comprises a DNA construct of the invention. In another embodiment, the transgenic plant, seed, cell, or plant part comprises a polypeptide of the invention.

The invention provides a method for conferring herbicide tolerance to a plant, seed, cell, or plant part comprising expressing in the plant, seed, cell, or plant part a polypeptide of the invention. In one embodiment, the method for conferring herbicide tolerance is used with a transgenic plant, seed, cell, or plant part that comprises a transgenic trait comprising a recombinant DNA molecule of the invention. In one embodiment, the method for conferring herbicide tolerance is used with an herbicide selected from the group consisting of AOPP herbicides, phenoxy acid herbicides, and pyridinyloxy acid herbicides.

The invention provides a method of plant transformation, comprising introducing a DNA construct of the invention into a plant cell and regenerating a plant therefrom that comprises the DNA construct and is tolerant to at least one herbicide selected from the group consisting of AOPP herbicides, phenoxy acid herbicides, and pyridinyloxy acid herbicides. In one embodiment, the method of plant transformation includes crossing the regenerated plant with itself or with a second plant and collecting seed from the cross.

The invention provides a method for controlling weeds in a plant growth area by contacting a plant growth area comprising a transgenic plant or seed of the invention with at least one herbicide selected from the group consisting of AOPP herbicides, phenoxy acid herbicides, and pyridinyloxy acid herbicides, where the transgenic plant or seed is tolerant to the herbicide.

BRIEF DESCRIPTION OF THE DRAWINGS

FIG. 1A shows control and transgenic maize plants either untreated or treated with 1× quizalofop-P (0.08 lb ai/acre). FIG. 1B shows F1 hybrid control maize plants and FIG. 1C shows F1 hybrid MON-HT55 transgenic maize plants. Plants were grown at daytime/night-time temperatures of (1) 20° C./20° C., (2) 28° C./20° C., or (3) 38° C./30° C. prior to being sprayed with 2× quizalofop-P.

FIG. 2A shows activity of MON-HT55 (SEQ ID NO:11) and the wild-type RdpA enzyme when tested with quizalofop-P as the substrate. FIG. 2B shows activity of MON-HTI (SEQ ID NO:14), MON-HT2 (SEQ ID NO:18), MON-HT7 (SEQ ID NO:34), MON-HT8 (SEQ ID NO:37) and the wild-type RdpA when tested with quizalofop-P as the substrate. FIG. 2C shows activity of MON-HT1, MON-HT2, MON-HT7, MON-HT8 and the wild-type RdpA when tested with 2,4-D as the substrate. Data are normalized to the activity of each protein at 25° C.

FIG. 3. The protein sequence of wild-type RdpA (SEQ ID NO:60) with exemplary amino acid positions useful for protein engineering boxed.

FIG. 4B shows data from plants acclimated at daytime temperature of 28° C. and night time temperature of 20° C. (28° C./20° C.) prior to application of 2× quizalofop-P; FIG. 4C shows data from plants acclimated at daytime temperature of 38° C. and night time temperature of 30° C. (38° C./30° C.) prior to application of 2× quizalofop-P (FIG. 4C) or 4× 2,4-D (FIG. 4E).

FIG. 5A and FIG. 5B: Control and transgenic maize plants comprising MON-HT2 (SEQ ID NO:20, encoding SEQ ID NO:18) with a CTP or without a CTP where the plants received quizalofop-P at 16× rates (1.28 lb ai/acre) applied at V2 followed by V4 and the photos taken 10 to 14 days after quizalofop-P application.

BRIEF DESCRIPTION OF THE SEQUENCES

Figure 1A:
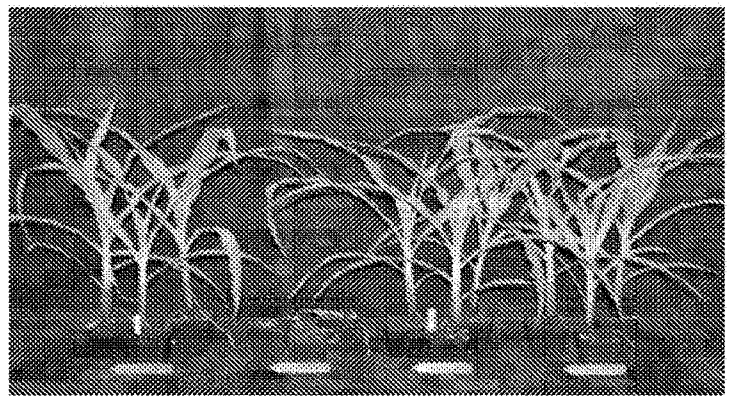
FIGS. 1A-1C. Control and MON-HT55 (SEQ ID NO:11) transgenic maize plants following treatment with quizalofop-P.

SEQ ID NO:1-3 are the amino acid sequence, bacterial codon polynucleotide sequence, and monocot codon optimized polynucleotide sequence of MON-HT51.

SEQ ID NO:4-6 are the amino acid sequence, bacterial codon polynucleotide sequence, and monocot codon optimized polynucleotide sequence of MON-HT52.

SEQ ID NO:7-8 are the amino acid sequence and bacterial codon polynucleotide sequence of MON-HT53.

SEQ ID NO:9-10 are the amino acid sequence and bacterial codon polynucleotide sequence of MON-HT54.

SEQ ID NO:11-13 are the amino acid sequence, bacterial codon polynucleotide sequence, and monocot codon optimized polynucleotide sequence of MON-HT55.

SEQ ID NO:14-17 are the amino acid sequence, bacterial codon polynucleotide sequence, monocot codon optimized polynucleotide sequence, and dicot codon optimized polynucleotide sequence of MON-HT1.

SEQ ID NO:18-21 are the amino acid sequence, bacterial codon polynucleotide sequence, monocot codon optimized polynucleotide sequence, and dicot codon optimized polynucleotide sequence of MON-HT2.

SEQ ID NO:22-24 are the amino acid sequence, bacterial codon polynucleotide sequence, and monocot codon optimized polynucleotide sequence of MON-HT3.

SEQ ID NO:25-27 are the amino acid sequence, bacterial codon polynucleotide sequence, and monocot codon optimized polynucleotide sequence of MON-HT4.

SEQ ID NO:28-30 are the amino acid sequence, bacterial codon polynucleotide sequence, and monocot codon optimized polynucleotide sequence of MON-HT5.

SEQ ID NO:31-33 are the amino acid sequence, bacterial codon polynucleotide sequence, and monocot codon optimized polynucleotide sequence of MON-HT6.

SEQ ID NO:34-36 are the amino acid sequence, bacterial codon polynucleotide sequence, and monocot codon optimized polynucleotide sequence of MON-HT7.

SEQ ID NO:37-39 are the amino acid sequence, bacterial codon polynucleotide sequence, and monocot codon optimized polynucleotide sequence of MON-HT8.

SEQ ID NO:40-42 are the amino acid sequence, bacterial codon polynucleotide sequence, and monocot codon optimized polynucleotide sequence of MON-HT9.

SEQ ID NO:43-45 are the amino acid sequence, bacterial codon polynucleotide sequence, and monocot codon optimized polynucleotide sequence of MON-HT10.

SEQ ID NO:46-52 are the amino acid sequences of MON-HT11, MON-HT13, MON-HT14, MON-HT15, MON-HT16, MON-HT17, and MON-HT18.

SEQ ID NO:53-59 are the dicot codon optimized polynucleotide sequences of MON-HT11, MON-HT13, MON-HT14, MON-HT15, MON-HT16, MON-HT17, and MON-HT18.

SEQ ID NO:60 is the amino acid sequence for wild-type RdpA from Sphingobium herbicidovorans.

SEQ ID NO:61 is the consensus sequence of FIG. 6A-FIG. 6E.

DETAILED DESCRIPTION OF THE INVENTION

The following definitions and methods are provided to better define the invention and to guide those of ordinary skill in the art in the practice of the invention. Unless otherwise noted, terms are to be understood according to conventional usage by those of ordinary skill in the relevant art.

The invention overcomes the limitations of the prior art by providing novel, engineered proteins, referred to herein as MON-HT proteins, and the recombinant DNA molecules that encode them as well as compositions and methods using these. The MON-HT proteins are oxygenases that can inactivate aryloxyphenoxypropionate (AOPP) herbicides, phenoxy acid herbicides, and pyridinyloxy acid herbicides. As used herein, inactivating an herbicide means making the herbicide no longer have its herbicidal activity against a plant. The MON-HT proteins exhibit novel substrate selectivity, useful enzyme kinetics, and increased enzyme stability at elevated temperature. Transgenic plants expressing a MON-HT protein demonstrate improved tolerance to application of AOPP, phenoxy acid herbicides, and pyridinyloxy acid herbicides.

Engineered Proteins and Recombinant DNA Molecules

The invention provides novel, engineered proteins and the recombinant DNA molecules that encode them. As used herein, the term "engineered" refers to a non-natural DNA, protein, or organism that would not normally be found in nature and was created by human intervention. An "engineered protein" is a protein whose polypeptide sequence was conceived of and created in the laboratory using one or more of the techniques of protein engineering, such as protein design using site-directed mutagenesis and directed evolution using random mutagenesis and DNA shuffling. For example, an engineered protein may have one or more deletions, insertions, or substitutions relative to the coding sequence of the wild-type protein and each deletion, insertion, or substitution may consist of one or more amino acids. Examples of engineered proteins are provided herein as SEQ ID NO:1, 4, 7, 9, 11, 14, 18, 22, 25, 28, 31, 34, 37, 40, 43, and 46-52.

Engineered proteins provided by the invention are enzymes that have oxygenase activity. As used herein, the term "oxygenase activity" means the ability to oxidize a substrate by transferring the oxygen from molecular oxygen to the substrate, co-product, or an intermediary. The oxygenase activity of the engineered proteins provided by the invention can inactivate one or more of AOPP herbicides, phenoxy acid herbicides, and pyridinyloxy acid herbicides.

As used herein, "wild-type" means naturally-occurring. As used herein, a "wild-type DNA molecule", "wild-type polypeptide", or a "wild-type protein" is a naturally-occurring DNA molecule, polypeptide, or protein, that is, a DNA molecule, polypeptide, or protein pre-existing in nature. A wild-type version of a polypeptide, protein, or DNA molecule may be useful for comparison with an engineered protein or gene. An example of a wild-type protein useful for comparison with the engineered proteins provided by the invention is the RdpA enzyme from *Sphingobium herbicidovorans* strain MH. An example of a wild-type DNA molecule useful for comparison with the recombinant DNA molecules provided by the invention is the RdpA gene from *Sphingobium herbicidovorans* strain MH. A wild-type version of a protein or DNA molecule may be useful as a control in an experiment.

As used herein, "control" means an experimental control designed for comparison purposes. For example, a control plant in a transgenic plant analysis is a plant of the same type as the experimental plant (that its, the plant to be tested) but does not contain the transgenic insert, recombinant DNA molecule, or DNA construct of the experimental plant. An example of a control plant useful for comparison with transgenic maize plants is non-transgenic LH244 maize (U.S. Pat. No. 6,252,148) and with transgenic soy plants is non-transgenic A3555 soybean (U.S. Pat. No. 7,700,846).

As used herein, the term "recombinant" refers to a non-natural DNA, polypeptide, or protein that is the result of genetic engineering and as such would not normally be found in nature and was created by human intervention. A "recombinant DNA molecule" is a DNA molecule comprising a DNA sequence that does not naturally occur and as such is the result of human intervention, for example, a DNA molecule that encodes an engineered protein. Another example is a DNA molecule comprised of a combination of at least two DNA molecules heterologous to each other, such as a protein-coding DNA molecule and an operably linked heterologous promoter. An example of a recombinant DNA molecule is a DNA molecule comprising at least one sequence selected from SEQ ID NO:2, 3, 5, 6, 8, 10, 12, 13, 15, 16, 17, 18, 19, 20, 21, 23, 24, 26, 27, 29, 30, 32, 33, 35, 36, 38, 39, 41, 42, 44, 45 and 53-59. A "recombinant polypeptide" or "recombinant protein" is a polypeptide or protein comprising an amino acid sequence that does not naturally occur and as such is the result of human intervention, for example, an engineered protein.

The term "transgene" refers to a DNA molecule artificially incorporated into the genome of an organism as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the invention comprise the recombinant DNA molecules and engineered proteins provided by the invention.

As used herein, the term "heterologous" refers to the relationship between two or more things derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell or organism into which it is inserted when it would not naturally occur in that particular cell or organism.

As used herein, the term "protein-coding DNA molecule" or "polypeptide-coding DNA molecule" refers to a DNA molecule comprising a nucleotide sequence that encodes a protein or polypeptide. A "protein-coding sequence" or "polypeptide-coding sequence" means a DNA sequence that encodes a protein or polypeptide. A "sequence" means a sequential arrangement of nucleotides or amino acids. The boundaries of a protein-coding sequence or polypeptide-coding sequence are usually determined by a translation start codon at the 5'-terminus and a translation stop codon at the 3'-terminus. A protein-coding molecule or polypeptide-coding molecule may comprise a DNA sequence encoding a protein or polypeptide sequence. As used herein, "transgene expression", "expressing a transgene", "protein expression", "polypeptide expression", "expressing a protein", and "expressing a polypeptide" mean the production of a protein or polypeptide through the process of transcribing a DNA molecule into messenger RNA (mRNA) and translating the mRNA into polypeptide chains, which may be ultimately folded into proteins. A protein-coding DNA molecule or polypeptide-coding DNA molecule may be operably linked to a heterologous promoter in a DNA construct for use in expressing the protein or polypeptide in a cell transformed with the recombinant DNA molecule. As used herein, "operably linked" means two DNA molecules linked in manner so that one may affect the function of the other. Operably-linked DNA molecules may be part of a single contiguous molecule and may or may not be adjacent. For example, a promoter is operably linked with a protein-coding DNA molecule or polypeptide-coding DNA molecule in a DNA construct where the two DNA molecules are so arranged that the promoter may affect the expression of the transgene.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of transformation, that is the introduction of heterologous DNA into a host cell, in order to produce transgenic plants and cells, and as such may also be contained in the plastid DNA or genomic DNA of a transgenic plant, seed, cell, or plant part. As used herein, a "vector" means any recombinant DNA molecule that may be used for the purpose of plant transformation. Recombinant DNA molecules as set forth in the sequence listing, can, for example, be inserted into a vector as part of a construct having the recombinant DNA molecule operably linked to a promoter that functions in a plant to drive expression of the engineered protein encoded by the recombinant DNA molecule. Methods for constructing DNA constructs and vectors are well known in the art. The components for a DNA construct, or a vector comprising a DNA construct, generally include, but are not limited to, one or more of the following: a suitable promoter for the expression of an operably linked DNA, an operably linked protein-coding DNA molecule, and a 3' untranslated region (3'-UTR). Promoters useful in practicing the present invention include those that function in a plant for expression of an operably linked polynucleotide. Such promoters are varied and well known in the art and include those that are inducible, viral, synthetic, constitutive, temporally regulated, spatially regulated, and/or spatio-temporally regulated. Additional optional components include, but are not limited to, one or more of the following elements: 5'-UTR, enhancer, leader, cis-acting element, intron, chloroplast transit peptides (CTP), and one or more selectable marker transgenes.

The DNA constructs of the invention may include a CTP molecule operably linked to the protein-coding DNA molecules provided by the invention. A CTP useful in practicing the present invention includes those that function to facilitate localization of the engineered protein molecule within the cell. By facilitating protein localization within the cell, the CTP may increase the accumulation of engineered protein, protect it from proteolytic degradation, enhance the level of herbicide tolerance, and thereby reduce levels of injury after herbicide application. CTP molecules for use in the present invention are known in the art and include, but are not limited to the *Arabidopsis thaliana* EPSPS CTP (Klee et al., 1987), the *Petunia hybrida* EPSPS CTP (della-Cioppa et al., 1986), the maize cab-m7 signal sequence (Becker et al., 1992; PCT WO 97/41228) and the pea glutathione reductase signal sequence (Creissen et al., 1991; PCT WO 97/41228).

Recombinant DNA molecules of the present invention may be synthesized and modified by methods known in the art, either completely or in part, especially where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes recombinant DNA molecules and engineered proteins having at least about 80% (percent) sequence identity, about 85% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, and about 99% sequence identity to any of the recombinant DNA molecule or engineered protein sequences provided herein, for instance, to a recombinant DNA molecule comprising a sequence selected from the group consisting of SEQ ID NO:2, 3, 5, 6, 8, 10, 12, 13, 15, 16, 17, 18, 19, 20, 21, 23, 24, 26, 27, 29, 30, 32, 33, 35, 36, 38, 39, 41, 42, 44, 45, and 53-59. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, CA), MEGAlign (DNAStar, Inc., 1228 S. Park St., Madison, Wis. 53715), and MUSCLE (version 3.6) (RC Edgar, Nucleic Acids Research (2004) 32 (5): 1792-1797) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

Engineered proteins may be produced by changing (that is, modifying) a wild-type protein to produce a new protein with a novel combination of useful protein characteristics, such as altered Vmax, Km, substrate specificity, substrate selectivity, and protein stability. Modifications may be made at specific amino acid positions in a protein and may be a substitution of the amino acid found at that position in nature (that is, in the wild-type protein) with a different amino acid. Exemplary amino acid positions relative to the protein sequence of wild-type protein RdpA (SEQ ID NO: 60) useful for protein engineering are depicted in FIG. 3. FIGS. 6A, 6B, 6C, 6D, 6E provide a multi-sequence alignment of the wild-type RdpA protein sequence and engineered protein sequences SEQ ID NO:1, 4, 7, 9, 11, 14, 18, 22, 25, 28, 31, 34, 37, 40, 43, and 46-52. An engineered protein can be designed that has at least about 92% sequence identity to an amino acid sequence selected from the group consisting of SEQ ID NO:1, 4, 7, 9, 11, 14, 18, 22, 25, 28, 31, 34, 37, 40, 43, and 46-52 and comprises at least one of these amino acid mutations. Engineered proteins provided by the invention thus provide a new protein with one or more altered protein characteristics relative to the wild-type protein found in nature. In one embodiment of the invention, an engineered protein has altered protein characteristics such as improved or decreased activity against one or more herbicides or improved protein stability as compared to a similar wild-type protein, or any combination of such characteristics. In one embodiment, the invention provides an engineered protein, and the recombinant DNA molecule encoding it, having at least about 80% sequence identity, about 85% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, and about 99% sequence identity to an engineered protein sequence selected from the group consisting of SEQ ID NO:1, 4, 7, 9, 11, 14, 18, 22, 25, 28, 31, 34, 37, 40, 43, and 46-52. Amino acid mutations may be made as a single amino acid substitution in the protein or in combination with one or more other mutation(s), such as one or more other amino acid substitution(s), deletions, or additions. Mutations may be made as described herein or by any other method known to those of skill in the art.

Transgenic Plants

An aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit herbicide tolerance to one or more of aryloxyphenoxypropionate (AOPP) herbicides, phenoxy acid herbicides, and pyridinyloxy acid herbicides.

Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, typically using a SNP assay, DNA sequencing, or a thermal amplification assay that allows for the distinction between heterozygotes and homozygotes, referred to as a zygosity assay.

Plants, seeds, plant parts, plant tissues, and cells provided by the invention exhibit herbicide tolerance to one or more of AOPP herbicides, phenoxy acid herbicides, and pyridinyloxyl acid herbicides. AOPP herbicides target the plant's acetyl-coenzyme A carboxylase (ACCasc), which is part of the fatty acid biosynthetic pathway. Grass plants are sensitive to these herbicides because they contain herbicide-sensitive ACCase in their plastids and cytosol. AOPP herbicides are well-known in the art and commercially available. Examples of AOPP herbicides include, but are not limited to, clodinafop, cyhalofop, diclofop, fenoxaprop, fenoxaprop-P, fenthiaprop, fluazifop, fluazifop-P, haloxyfop, isoxapyrifop, metamifop, propaquizafop, quizalofop, quizalofop-P, and trifop. The phenoxy acid and pyridinyloxy acid herbicides are synthetic auxins similar to the plant growth hormone indoleacetic acid (IAA). Broad-leaf plants are sensitive to these herbicides, which induce rapid, uncontrolled growth, eventually killing the plant. Examples of phenoxy acid herbicides include, but are not limited to, 2,4-D; 2,4-DB; clomeprop; dichlorprop; fenoprop; MCPA; MCPB, and mecoprop. Examples of pyridinyloxy acid herbicides include, but are not limited to, triclopyr; fluroxypyr; aminopyralid, clopyralid, and picloram.

Herbicides may be applied to a plant growth area comprising the plants and seeds provided by the invention as a method for controlling weeds. Plants and seeds provided by the invention comprise an herbicide tolerance trait and as such are tolerant to the application of one or more AOPP herbicides, or phenoxy acid herbicides, or pyridinyloxyl acid herbicides. The herbicide application may be the recommended commercial rate (1×) or any fraction or multiple thereof, such as twice the recommended commercial rate (2×). Herbicide rates may be expressed as acid equivalent per pound per acre (lb ac/acre) or pounds active ingredient per acre (lb ai/acre). The herbicide application comprises at least one herbicide selected from the group consisting of AOPP herbicides, and phenoxy acid herbicides, and pyridinyloxy acid herbicides. The plant growth arca may or may not comprise weed plants at the time of herbicide application. An herbicidally effective dose of AOPP herbicides for use in the area for controlling weeds should consist of a range from about 0.01 lb ai/acre to about 16 lb ai/acre over a growing season. For example, a 1× rate of quizalofop-P would be a rate of 0.08 lb ai/acre. An herbicidally effective dose of phenoxy acid herbicides for use in the area for controlling weeds should consist of a range from about 0.01 lb ac/acre to about 16 lb ac/acre over a growing season. For example, a 1× rate of 2,4-D would be a rate of about 0.75 lb ac/acre to 1.0 lb ac/acre. An herbicidally effective dose of pyridinyloxy acid herbicides for use in the area for controlling weeds should consist of a range from about 0.01 lb ac/acre to about 16 lb ac/acre over a growing season. For example, a 1× rate of fluroxypyr would be a rate of about 0.13 to 0.48 lb ac/acre.

The herbicide application may be sequentially or tank mixed with one, two, or a combination of several AOPP herbicides, phenoxy acid herbicides, pyridinyloxy acid herbicides, or any other compatible herbicide. Multiple applications of one herbicide or of two or more herbicides, in combination or alone, may be used over a growing season to areas comprising transgenic plants of the invention for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, "tolerance" or "herbicide tolerance" means a plant, seed, plant tissue, plant part, or cell's ability to resist the toxic effects of one or more herbicide(s). The herbicide tolerance of a plant, seed, plant tissuc, plant part, or cell may be measured by comparing the plant, seed, plant tissue, plant part, or cell to a suitable control. For example, the herbicide tolerance may be measured or assessed by applying an herbicide to a plant comprising a recombinant DNA molecule encoding a protein capable of conferring herbicide tolerance (the test plant) and a plant not comprising the recombinant DNA molecule encoding the protein capable of conferring herbicide tolerance (the control plant) and then comparing the plant injury of the two plants, where herbicide tolerance of the test plant is indicated by a decreased injury rate as compared to the injury rate of the control plant. An herbicide tolerant plant, seed, plant tissue, plant part, or cells exhibits a decreased response to the toxic effects of an herbicide when compared to a control plant, seed, plant tissue, plant part, or cell. As used herein, an "herbicide tolerance trait" is a transgenic trait imparting improved herbicide tolerance to a plant as compared to a wild-type plant or control plant.

The transgenic plants, progeny, seeds, plant cells, and plant parts of the invention may also contain one or more additional transgenic traits. Additional transgenic traits may be introduced by crossing a plant containing a transgene comprising the recombinant DNA molecules provided by the invention with another plant containing an additional transgenic trait(s). As used hercin, "crossing" means breeding two individual plants to produce a progeny plant. Two transgenic plants may thus be crossed to produce progeny that contain the transgenic traits. As used herein "progeny" means the offspring of any generation of a parent plant, and transgenic progeny comprise a DNA construct provided by the invention and inherited from at least one parent plant. Alternatively, additional transgenic trait(s) may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation on a transgenic plant or plant cell). Such additional transgenic traits include, but are not limited to, increased insect resistance, increased water use efficiency, increased yield performance, increased drought resistance, increased seed quality, improved nutritional quality, hybrid seed production, and herbicide tolerance, in which the trait is measured with respect to a wild-type plant or control plant. Such additional transgenic traits are known to one of skill in the art; for example, a list of such traits is provided the United States Department of Agriculture's (USDA) Animal and Plant Health Inspection Service (APHIS) and can be found on their website at www.aphis.usda.gov.

Transgenic plants and progeny that contain a transgenic trait provided by the invention may be used with any breeding methods that are commonly known in the art. In plant lines comprising two or more transgenic traits, the transgenic traits may be independently segregating, linked, or a combination of both in plant lines comprising three or more transgenic traits. Back-crossing to a parental plant and out-crossing with a non-transgenic plant are also contemplated, as is vegetative propagation. Descriptions of breeding methods that are commonly used for different traits and crops are well known to those of skill in the art. To confirm the presence of the transgene(s) in a particular plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and Western blots) or by enzymatic function; plant part assays, such as leaf or root assays; and also, by analyzing the phenotype of the whole plant.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly a plant genotype lacking the desired transgenic trait may be referred to as an unconverted genotype, line, inbred, or hybrid.

As used herein, the term "comprising" means "including but not limited to".

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit, and scope of the invention. More specifically, it will be apparent that certain agents which are both chemically and physiologically related may be substituted for the agents described herein with the same or similar result achieved. All such similar substitutes and modifications apparent to those skilled in the art are deemed to be within the spirit, scope, and concept of the invention as defined by the appended claims.

Example 1

Initial Protein Engineering and Enzyme Analysis

Novel, engineered proteins and recombinant DNA molecules encoding these proteins were conceived of and created in the laboratory using the techniques of protein engineering. The engineered proteins are enzymes that have oxygenase activity and were engineered to have altered abilities to inactivate AOPP herbicides, phenoxy acid herbicides, or both relative to the wild-type protein.

Sixteen known proteins with oxygenase activity were selected and used to create a consensus homology sequence alignment. This was used in combination with structure-guided analyses to inform rational design strategies. From these analyses, five regions cach from 13 to 21 amino acids in length, referred to herein as "islands", were selected for mutatagenesis. Mutations in each of these regions were created using techniques known to those of skill in the art, such as Alanine-Scanning Mutations; Homology-Scanning Mutations; Pro/Gly Scanning Mutations; Region Swaps or Mutations; and combinations of these various techniques (see, M Lehmann and M Wyss, Current Opinion in Biotechnology (2001) 12(4):371-375; B Van den Burg and VGH Eijsink, Current Opinion in Biotechnology (2002) 13(4): 333-337; and Weiss et al., Proc Natl Acad Sci USA (2000) 97(16):8950-8954). Using these methods, more than 1,200 unique engineered proteins and the recombinant DNA molecules that encode them were generated for further analysis and characterization. Because of the large number of engineered proteins produced for testing, and the need to test and compare the enzymatic activity of each protein, a high-throughput bacterial protein expression and enzyme assay system was developed for rapid analysis using crude bacterial extracts.

The high-throughput bacterial protein expression was achieved by synthesizing a recombinant DNA molecule encoding each engineered protein and cloning this into a bacterial expression vector with a C-terminal histidine tag (His-tag) operably linked to the recombinant DNA molecule. The vectors were used to transform *Escherichia coli* (*E. coli*), and bacterial expression of the engineered proteins was induced. Overnight *E. coli* cultures were grown in 96-well plates and the cultures were centrifuged to pellet the bacteria. The bacterial pellets were lysed by adding 100 ul lysis master mix (10 ml of Bacteria Protein Extraction Reagent (B-PER®) II (Pierce Biotechnology, Rockford, IL; cat. no. 78260); 10 ul Lysozyme (10 ug/ml final; Lysozyme American Bioanalytical, Natick, MA; cat. no. AB011780-00005); and 40 ul Benzonase® Nuclease (100 Units/ml final, Novagen, Darmstadt, Germany; cat no 71206-3)) to each well. The plates were vortexed then incubated for 30 minutes at 4° C. 400 ul of MOPS buffer (pH 6.57) was added to cach well and the debris pelleted by centrifugation. The lysate supernatant was carefully removed and used as the crude bacterial extract for subsequent enzymatic analysis.

The high-throughput herbicide degradation enzyme assay was designed to assay the enzymatic activity of the engineered proteins towards various herbicides using crude bacterial extract. The engineered protein's oxygenase activity (that is, its enzymatic activity) was measured by an end point colorimetric assay utilizing detection of phenol products through measurement of absorbance at 510 nm from 4-aminoantipyrine and potassium ferricyanide. This assay was based on the assay described in Fukomori and Hausinger, Journal of Biological Chemistry (1993) 268(32): 24311-24317. Enzyme reactions were assayed in 96-well plates in a total volume of 150ul that contained: 20 mM MOPS pH 6.75, 50-200 uM NH4FeSO4, 50-200 uM sodium ascorbate, 1 mM alpha-ketoglutarate (aKG), 10 ul of *E. coli* cell lysate containing expressed engineered protein, and substrate (either an AOPP herbicide or phenoxy acid herbicide). Upon initiation of the reaction with substrate, the plate was incubated at various temperatures for various times and quenched (terminated) by the addition of EDTA to a final concentration of 6.25 mM or by the addition of 15 ul of pH 10 buffer (50 mM boric acid, 50 mM KCl) followed by 15 ul of 0.2% 4-aminoantipyrine and 15 ul of 0.8% potassium ferricyanide. Absorbance measurements were made on a standard laboratory spectrometer. Assays were scaled as needed to enhance throughput. Standard curves were generated using purified protein or product standards.

Using this high-throughput bacterial protein expression and enzyme assay system, activities of approximately 1200 engineered proteins were measured relative to the activity of a selected wild-type protein, RdpA. In a 96 well plate assay, there were 3 controls (crude bacterial extract without an engineered protein) and 3 positive controls (crude bacterial extract with wild-type protein). The absorbance of the wells was measured and the protein activity was calculated using the following formula:

$$\text{Activity}_i = \left(\frac{(\text{Absorbance}_i - \text{Absorbance}_{\overline{pET}}}{(\text{Absorbance}_{\overline{WT}} - \text{Absorbance}_{\overline{pET}})}\right) \times 100$$

where, $\text{Activity}_i$ is the activity of the sample, $\text{Absorbance}_i$ is the absorbance of the sample, $\text{Absorbance}_{WT}$ is the absorbance of the wells containing extract from *E. coli* expressing the wild-type enzyme, and $\text{Absorbance}_{pET}$ is the absorbance of the wells containing extract from *E. coli* without an engineered protein. Activity for each unique engineered protein was measured in duplicate and was reported as an average of the two measurements.

Based on the results from the high-throughput enzyme assay system, approximately 545 unique engineered proteins were selected for further analysis using purified engineered protein. In the purified engineered protein prep assay, crude bacterial expression lysates were prepared using QUIAGEN® Ni-NTA Agarose (Qiagen, Valencia, CA, cat. no. 30230) following manufacturer's protocol.

The purified engineered proteins were assayed using the herbicide degradation enzyme assay described in this Example 1 with the AOPP herbicide quizalofop as the substrate. The results of the purified engineered protein assays largely confirmed the results from the high-throughput enzyme assay. Assay results for seven of the approximately 545 engineered proteins are shown in Table 1, where the enzymatic activity is expressed as the activity of the sample relative to the activity of the wild-type RdpA enzyme (calculated as described in this Example 1). These data from these assays yielded the surprising result that combinations of specific mutations performed significantly better than others and demonstrated that the enzymatic activity of the engineered proteins could be altered significantly.

TABLE 1

| Replicate Number | Island 1-2-3 | Island 1-2-5 | Island 1-3-4 | Island 2-3-4 | Island 2-3-5 | Island 2-4-5 | Island 3-4-5 |
|---|---|---|---|---|---|---|---|
| 1 | −5.94 | −4.14 | −4.86 | −2.84 | 138.99 | 48.12 | 4.06 |
| 2 | −3.54 | −2.64 | −3.9 | −0.05 | 117.67 | 48.84 | 5.56 |
| 3 | | −3.85 | | | 140.75 | | |
| 4 | | −0.65 | | | 113.77 | | |
| 5 | | −0.05 | | | 150.58 | | |
| 6 | | 2.14 | | | 141.27 | | |

Using the information learned from the first assays, protein engineering was then done as described previously to produce additional engineered proteins, which were tested as described in this Example 1. The results of the high-throughput enzyme assay with quizalofop-P as the substrate for five of these additional engineered proteins are provided in Table 2.

TABLE 2

| SEQ ID NO | MON-HT | Replicate 1 | Replicate 2 | Replicate 3 | Average quizalofop-P activity |
|---|---|---|---|---|---|
| 1 | MON-HT51 | 117.02 | 124.87 | 110.17 | 117.35 |
| 4 | MON-HT52 | 92.17 | 54.46 | 89.75 | 78.79 |
| 7 | MON-HT53 | 105.34 | 105.31 | 106.13 | 105.60 |
| 9 | MON-HT54 | 131.85 | 149.77 | 130.56 | 137.39 |
| 11 | MON-HT55 | 118.48 | 99.79 | | 109.13 |

Further protein characterization, such as Km, Vmax, and crystal structure analysis, was performed using the five engineered proteins from Table 2. For this detailed analysis, purified protein was prepared as follows: 2 ml overnight cultures of *E. coli* expressing a transgene encoding a given MON-HT protein were used to inoculate 500 ml of broth and grown at 37° C. for 4 hours followed by culture at 15° C. for approximately 36 hours. Then 250 ml of the 500 ml bacterial culture was pelleted by centrifugation and resuspended in 25 ml of extraction buffer (20 mM Tris, pH 7.8, 300 mM NaCl, 5 mM beta-mercaptoethanol (BME), 20 mM imidazole (Fluka/Sigma-Aldrich, St. Louis, MO), 125 units/ml of benzonase and 10K units/ml of lysozyme (Novagen, Darmstadt, Germany). The cell slurry was passed through a cell disruptor once at 20000 psi and then this cell lysate was clarified by centrifugation at 35,000×g for 20 min at 4° C. The supernatant containing the soluble His-tagged proteins was used for protein purification. For this purification, the supernatant was applied to a 1 ml HisTrap™ FF column (Nickel Sepharose) (GE Healthcare, Piscataway, NJ) using an AKTaxpress™ system (GE Healthcare, Piscataway, NJ) following the standard manufacturer's protocol. The wash buffer consisted of: 20 mM Tris pH 7.8, 300 mM NaCl, 20 mM imidazole and 5 mM BME. The composition of elution buffer was the same as the wash buffer except with 500 mM imidazole. The eluate from the nickel column was desalted on a Quick Spin Protein Sephadex G-25 fine column (Roche Applied Science, Indianapolis, IN) following the manufacturer's protocol. The eluted protein was in buffer consisting of: 20 mM Tris pH 7.8, 50 mM NaCl and 5 mM BME. Protein extract purity was assessed by SDS-PAGE analysis. Protein concentration was determined by Bradford assay using Bio-Rad Protein Assay dye reagent (Biorad, Hercules, CA, cat no 500-0006).

Purified protein for the five engineered proteins was analyzed using the enzyme assay described in this Example 1, but with four different AOPP herbicides as substrates: quizalofop-P, haloxyfop, fenoxaprop, and fluazifop. Standard curves were generated using 2,4-dichlorophenol (2,4-DCP), which was used to produce a general phenol standard curve. The amount of phenol generated in the assay by the engineered proteins was calculated based on this standard curve. The controls were purified wild-type enzyme, no enzyme, and no substrate. Enzyme kinetic measurements of the five engineered proteins was done using 0, 20, 40, 80, 160, 320, 640, or 1280 uM of quizalofop-P, haloxyfop, fenoxaprop, or fluazifop herbicides. Table 3 shows the Km and Vmax (expressed as relative values) measured for the five proteins with the four AOPP herbicide substrates. The protein characteristics of these five engineered proteins with each of the four AOPP herbicides as substrates demonstrated that the enzymatic activity, namely Km and Vmax, of the engineered proteins could be altered significantly through protein engineering.

TABLE 3

| | Quizalofop-P | | Haloxyfop | | Fenoxaprop | | Fluazifop | |
|---|---|---|---|---|---|---|---|---|
| | Km (uM) | Vmax | Km (uM) | Vmax | Km (uM) | Vmax | Km (uM) | Vmax |
| MON-HT51 | 570 | 120 | 250 | 48 | 870 | 180 | 4.0 | 12 |
| MON-HT52 | 420 | 39 | 280 | 45 | 490 | 420 | 14 | 43 |
| MON-HT53 | 690 | 95 | 290 | 64 | 1100 | 640 | 1.0 | 40 |
| MON-HT54 | 560 | 32 | 380 | 40 | 2100 | 630 | ND | ND |
| MON-HT55 | 250 | 320 | 450 | 190 | 200 | 450 | 50 | 320 |

Example 2

Expression of Engineered Proteins in Maize

Plant transformation vectors were constructed each comprising a recombinant DNA molecule encoding one of three engineered proteins with the protein-coding sequence optimized for monocot expression, MON-HT51 (SEQ ID NO:3), MON-HT52 (SEQ ID NO:6), and MON-HT55 (SEQ ID NO:13). The vectors were created using different combinations of promoter, leader, intron, and 3'UTR and with and without a CTP operably linked to the protein-coding sequence. Also included in the vectors was a second DNA cassette comprising a cp4-EPSPS coding sequence to be used in transgenic plants for glyphosate tolerance. Immature maize (LH244) embryos were transformed with these vectors using *Agrobacterium tumifaciens* and standard methods known in the art. Regenerated R0 transgenic plantlets were grown in the green house and sprayed at approximately V2-V4 growth stage with 0.04 or 0.08 lb ai/acre quizalofop-P (AssureTM II, E.I. DuPont), representing 0.5× and 1× rates, respectively. Leaf samples were used to identify transgenic plants with a single copy of the transgenic DNA insert (that is, single event plants). R0 plants that contained only a single copy and passed either 0.5× or 1× quizalofop-P spray testing were selfed to produce R1 seed. No events were obtained with the constructs containing MON-HT52. Only one event was regenerated from the construct containing MON-HT51 with a CTP and from the construct containing MON-HT51 without a CTP. Two pairs of vectors containing MON-HT55 were transformed, with each pair differing only in containing a CTP or not containing a CTP.

R1 plants expressing MON-HT55 with and without an operably linked CTP were grown in the green house and quizalofop-P herbicide was applied at the V2 growth stage at a rate of 0.08Ib ac/acre (1×). Plants were evaluated for injury eleven days after treatment. The R1 plants werc segregating for the trait in typical Mendelian ratio, and the expected numbers (~25%) of null segregants (progeny plants not containing the transgenic trait) were seen that did not survive the herbicide treatment. All R1 transgenic plants expressing MON-HT55 with an operably linked CTP, with the exception of those representing one event, showed only minor chlorotic speckling on the youngest exposed leaves following application of quizalofop-P. No injury scores over 5% were recorded for these plants after herbicide application. The unsprayed transgenic plants also did not differ phenotypically from the unsprayed control plants. FIG. 1A shows control LH244 plants and transgenic plants comprising MON-HT55 (SEQ ID NO:13) 18 days after application of quizalofop-P.

To assess the effect of using a CTP to target the engineered protein to the plant cell chloroplast, transgenic plants comprising a transgene insert with and without a CTP operably linked to the protein-coding sequence were compared. The plants comprising a CTP operably linked to the protein-coding sequence showed better tolerance to quizalofop-P compared to those without a CTP. In the R1 green house testing described in this Example 2, most of the transgenic plants comprising a CTP operably linked to the protein-coding sequence showed complete quizalofop-P tolerance. The plants not comprising a CTP operably linked to the protein-coding sequence showed quizalofop-P tolerance but with some moderate injury phenotypes. These results demonstrated that the use of a CTP to target the engineered protein to the plant cell chloroplast enhanced the transgenic plant's quizalofop-P tolerance. This unexpected finding was tested again in trait efficacy field trials with R1 plants comprising either MON-HT51 with or without a CTP operably linked to the protein-coding sequence or MON-HT55 with or without a CTP operably linked to the protein-coding sequence. These R1 plants were single-copy, but were still segregating. In this field trial, seed was planted in the field and treated as follows: 2× (0.16 lb ai/acre) quizalofop-P at pre-plant, 2× (0.14 lb ai/acre) haloxyfop at V4 growth stage, then 2× quizalofop-P at V8 growth stage. A higher percentage of plants comprising a CTP operably linked to the protein-coding sequence survived quizalofop-P and haloxyfop applications and had lower injury scores compared to plants not comprising a CTP operably linked to the protein-coding sequence. Data are provided in Table 4. This confirmed the unexpected finding that a CTP operably linked to the protein-coding sequence confers higher plant tolerance to herbicide application for the engineered proteins.

TABLE 4

| Protein | CTP | Unique events | Average % Herbicide Injury |
|---|---|---|---|
| MON-HT51 | No | 1 | 95% |
| MON-HT51 | Yes | 1 | 35% |
| MON-HT55 | No | 12 | 49% |
| MON-HT55 | Yes | 3 | 25% |
| MON-HT55 | No | 2 | 90% |
| MON-HT55 | Yes | 7 | 24% |

Inbred trait efficacy field trials were conducted to assess tolerance to the AOPP herbicides and sensitivity to the cyclohexanediones (CHD) herbicides in an inbred background. R2 inbred plants were generated by selfing a homozygous transgenic R1 plant and collecting seed. R2 inbred plants containing MON-HT55 with or without a CTP or MON-HT51 with a CTP and were evaluated at two field locations. Herbicide treatment was 2× quizalofop-P at 0.16 lb ai/acre applied PRE (after planting but before emergence) followed by quizalofop-P at 0.16 lb ai/acre applied at V4 growth stage followed by quizalofop-P at 0.16 lb ai/acre applied at V8 growth stage. Plots were rated for crop injury 7-10 days after herbicide application on a scale of 0-100 with zero being no injury and 100 being complete crop death. All data were subjected to analysis of variance and means separated at LSD (0.05). Most of the inbred R1 plants showed no injury, confirming that both MON-HT55 and MON-HT51, with or without a CTP, confer quizalofop-P tolerance to maize. To test for sensitivity to CHD herbicides, which is desirable for use in volunteer control, plants were treated with a 1× rate of clethodim (0.25 lb ai/acre) at V8 growth stage. Volunteer control using a 1× rate of clethodim was 100% effective for all transgenic plants tested. Hybrid trait efficacy field trials were conducted to assess tolerance to the AOPP herbicides and sensitivity to the cyclohexanediones (CHD) herbicides in a hybrid background. F1 hybrid plants were produced by crossing an R1 inbred plant with a non-transgenic plant and collecting seed. The resulting F1 plants containing MON-HT55 (SEQ ID NO:13) with or without a CTP or MON-HT51 (SEQ ID NO: 3) without a CTP were evaluated at six field locations. The hybrid trait efficacy field trials were conducted at six locations under a range of environmental conditions, including high heat and drought conditions during the field season. This permitted the engineered protein to be evaluated in maize under high temperature and water stress conditions. Data are provided in Table 5. Initial injury from 2× applications of quizalofop-P were higher than desired (>10% injury) at 7-10 days after application. Plants eventually grew out of most of the injury, with generally less injury from the V8 growth stage application as compared to the V4 growth stage application. Excessive injury was also noted when quizalofop-P was applied very early (for example, at VE-V2 growth stage).

TABLE 5

| Protein | CTP | Unique events evaluated | % injury after V4 spray | % injury after V8 spray |
|---|---|---|---|---|
| MON-HT51 | Yes | 4 | 51.8 | 33.3 |
| MON-HT55 | No | 9 | 46.8 | 78.8 |
| MON-HT55 | Yes | 17 | 42.6-48.3 | 14.2-38.8 |

Figure 1B:
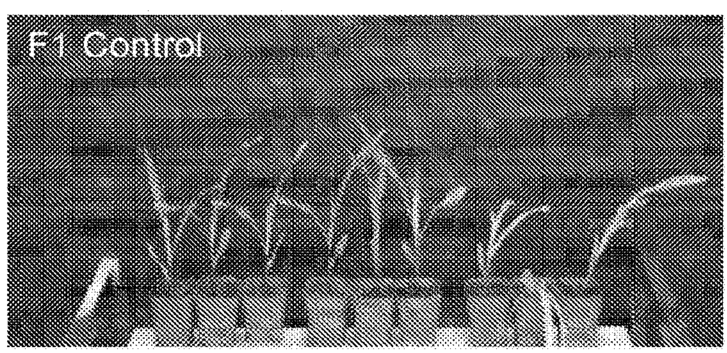
Figure 1C:
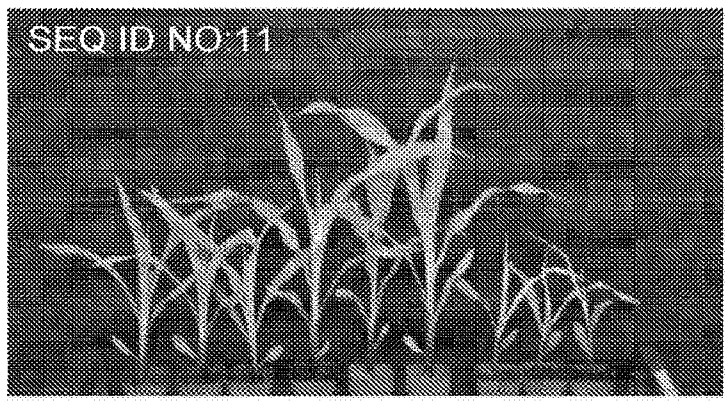

The finding that hybrid plants expressing the engineered proteins MON-HT55 or MON-HT51 were sensitive to quizalofop-P application when grown in field conditions of high temperature was confirmed using a plant-based assay. The plant-based assay was designed to test tolerance to quizalofop-P of F1 hybrids in the growth chamber prior to field testing. The assay was developed using F1 hybrids of plants containing maize events NK603 (U.S. Pat. No. 8,273,959)×MON89034 (U.S. Pat. No. 8,581,047) and F1 hybrids of plants containing MON-HT55×MON89034. F1 hybrid seed was germinated in a growth chamber for 1 week and then moved to one of three different growth chambers to acclimate for two days at day/night temperatures of 20° C./20° C., 28° C./20° C., and 38° C./30° C. prior to application of 2× (0.16 lb ai/acre) quizalofop-P. As expected, the plants not containing MON-HT55 at all temperature regimens were severely injured by 2× quizalofop-P application (FIG. 1B). The transgenic plants containing MON-HT55 showed good tolerance to the 2× quizalofop-P application when acclimated to day/night temperatures of 20° C./20° C. or 28° C./20° C., but showed significant sensitivity when acclimated to day/night temperatures of 38° C./30° C. (FIG. 1C). This confirmed that the plant-based assay could be used to screen proteins in plants in the growth chamber for temperature-sensitive activity.

The data demonstrated that the engineered proteins could be expressed in transgenic plants to confer herbicide tolerance and that unsprayed transgenic plants did not differ phenotypically from the unsprayed control plants. The data also confirmed that expression of the engineered proteins in plants permitted use of CHD herbicides for volunteer control. Unexpectedly, the data showed that use of a CTP for chloroplast targeting of the engineered protein enhanced the herbicide tolerance trait and that the herbicide tolerance provided by the engineered proteins was temperature-sensitive, decreasing under high temperature conditions.

Example 3

Optimizing Engineered Proteins

The finding that hybrid events expressing the engineered proteins MON-HT55 or MON-HT51 were sensitive to quizalofop-P application when grown in field conditions of high temperature was surprising and provided an additional protein characteristic capable of being altered through protein engineering. A new series of in vitro enzyme assays and a plant-based enzyme activity assay were developed to test proteins for sensitivity to high temperatures.

To create engineered proteins optimized for activity in higher temperatures, the protein motif analysis used in the first two rounds of protein engineering was combined with crystal structure data for several of the engineered proteins. This was used to inform additional rounds of mutagenesis, performed as described previously, and approximately 1400 additional engineered proteins were thus generated. These were combined with the approximately 1200 engineered proteins described in Example 1 for a total of approximately 2600 engineered proteins for screening with the new temperature sensitivity assay to identify proteins optimized for activity in higher temperatures.

Figures 2A, 2B, 2C:
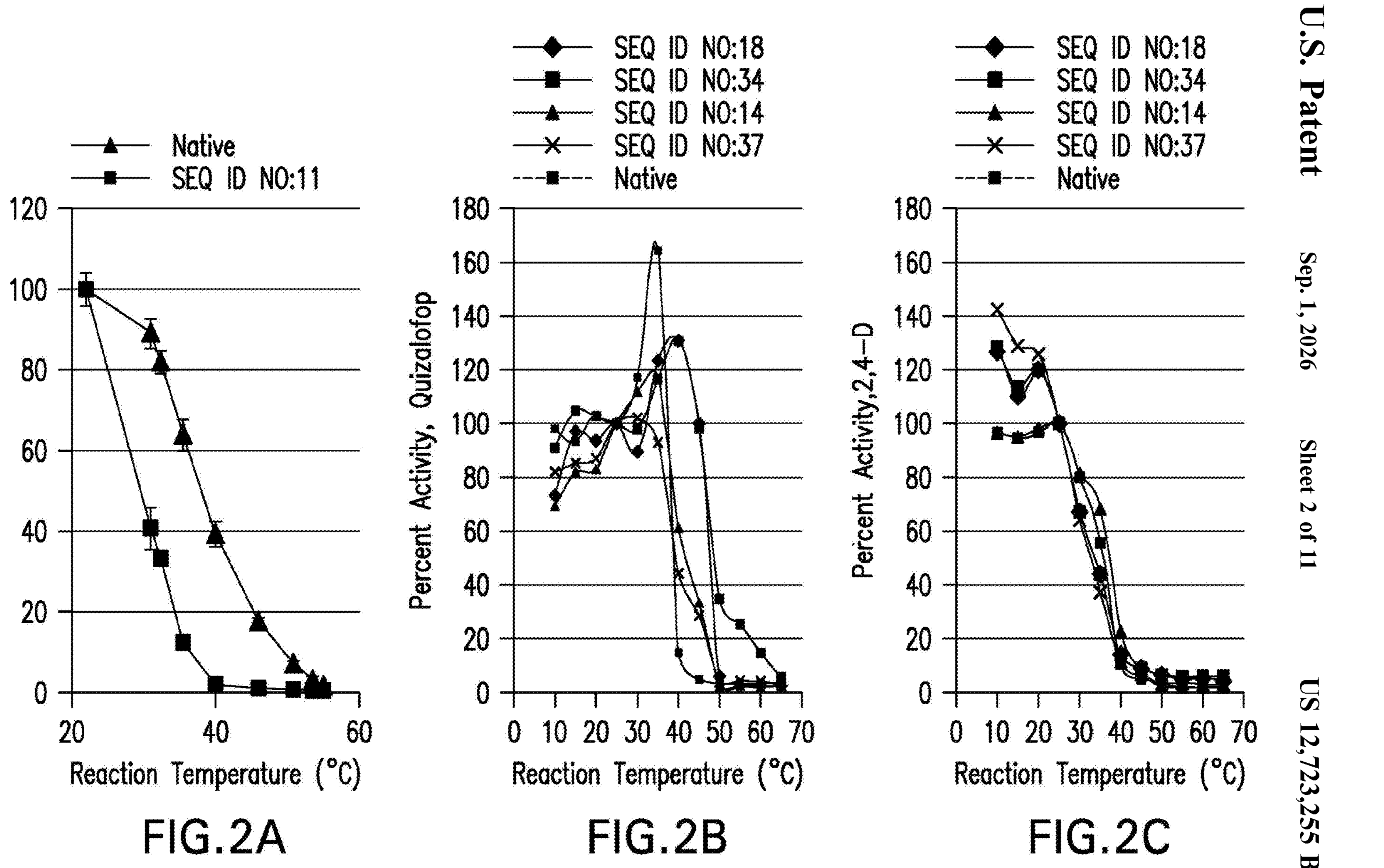
FIGS. 2A-2C. Graphs showing temperature-dependent activity of engineered proteins.

To analyze these engineered proteins for activity in higher temperatures, the in vitro enzyme assay in Example 1 was modified to specify pre-heating all of the assay components to the desired temperature for 5 minutes before combining the components and then maintaining the reaction at the desired temperature for the duration of the reaction. To normalize the assay measurements, quizalofop-P was used as the substrate for the reaction and enzyme activity was normalized based on the 25° C. readings. Using these parameters, the temperature at which the enzyme activity was half of maximum ($T_{1/2}$) was calculated. The $T_{1/2}$ for MON-HT55 was calculated to be 29° C., and the $T_{1/2}$ for wild-type RdpA was calculated to be 38° C. (FIG. 2A).

Because of the large number of variants to test, a five-level screening process was used. Table 6 shows the approximate number of variants tested in the different screenings.

TABLE 6

| | Engineered proteins tested |
|---|---|
| First screen | ~2600 |
| Second screen | ~1250 |
| Third screen | 94 |
| Fourth screen | 47 |
| Fifth screen | 11 |

The first screen was performed with approximately 2600 engineered proteins and used the high-throughput bacterial protein expression and enzyme assay system with crude bacterial lysates as described in Example 1 but modified to be conducted at the desired temperatures of 25° C. and 40° C. with the post-quenching color development done at 25° C. From this screen, approximately 1250 engineered proteins were selected and advanced. The second screen was similar, but included protein normalization across samples. From this screen, 94 engineered proteins were selected and advanced. The third screen used purified protein with the herbicide degradation enzyme assay as described in Example 1, but modified to be conducted at the desired temperatures of 25° C. and 40° C. with the post-quenching color development done at 25° C. From this screen, 47 engineered proteins were selected and advanced. The fourth screen was done using purified protein, the protein concentrations were normalized, and the screening included quizalofop-P and (for a subset of the proteins variants) 2,4-D as substrates with end-point assays done at 23° C. and 40° C. From this screen, thirteen engineered proteins were selected and advanced.

For the fifth screen, recombinant protein for each of the eleven engineered proteins was produced and purified for an in-depth biochemical analysis. This biochemical analysis included: (1) kinetic analysis (Vmax and Km), (2) activity assays over a range of temperatures, (3) protein melting analysis, (4) activity on additional AOPP herbicides substrates, and (5) mass spectrometry analysis on peptides to confirm identity. The biochemical analyses were also done with purified recombinant wild-type protein and MON-HT55 protein for comparison. For the kinetic analysis, a non-endpoint assay was conducted at 23° C. with either quizalofop-P or 2,4-D as substrate. The recombinant proteins for these assays were produced in bacteria and purified using a 6-His tag fused at the C-terminal end of the protein. Results of the kinetic analysis with either quizalofop-P or 2,4-D as substrate are presented for ten of the engineered proteins, wild-type protein, and MON-HT55 protein in Table 7 (standard error is shown in parenthetical). Vmax is expressed as specific activity, umol herbicide product mg enzyme-1 min-1; Km expressed as mM herbicide substrate. NDB indicates that enzyme activity may be evident at higher concentrations of herbicide, but activity under the concentrations tested was not robust enough to provide proper kinetic characterization. For MON-HT55, low activity levels (Vmax) with 2,4-D as the substrate resulted in low confidence in the reported value. MON-HT7 had a Vmax with quizalofop-P that is approximately 40% greater than the wild-type enzyme and a Vmax for 2,4-D that is only about half of that of the wild-type enzyme. MON-HT1 had a Vmax for quizalofop-P that is about half that of the wild-type enzyme and a Vmax for 2,4-D that is 9.5-fold higher than that of the wild-type enzyme. The differentiation of the protein kinetics for MON-HTI and MON-HT7 were surprising because there are only four amino acid differences between MON-HT1 and MON-HT7. Specifically, MON-HT1 has the following amino acids at the indicated position: 182; F105; T112; and V273, and MON-HT7 has the following amino acids at the indicated position: L82; V105; S112; and A273.

TABLE 7

| Protein | Vmax Quizalofop | Km Quizalofop | Vmax 2,4-D | Km 2,4-D |
|---|---|---|---|---|
| MON-HT55 (SEQ ID NO: 11) | 0.44 (−0.04) | 0.32 (−0.07) | 0.03 (−0.02) | 0.69 (−0.66) |
| MON-HT1 (SEQ ID NO: 14) | 0.76 (−0.04) | 0.17 (−0.03) | 0.95 (−0.03) | 0.03 (0.00) |
| MON-HT2 (SEQ ID NO: 18) | 1.41 (−0.11) | 0.41 (−0.06) | 0.23 (−0.01) | 0.04 (−0.01) |
| MON-HT3 (SEQ ID NO: 22) | 0.77 (−0.04) | 0.38 (−0.05) | 0.10 (−0.01) | 0.27 (−0.06) |
| MON-HT4 (SEQ ID NO: 25) | 0.30 (−0.02) | 0.24 (−0.05) | NDB | NDB |
| MON-HT5 (SEQ ID NO: 28) | 0.57 (−0.03) | 0.17 (−0.03) | NDB | NDB |
| MON-HT6 (SEQ ID NO: 31) | 0.39 (−0.03) | 0.10 (−0.03) | NDB | NDB |
| MON-HT7 (SEQ ID NO: 34) | 1.94 (−0.12) | 0.33 (−0.05) | 0.04 (−0.01) | 0.06 (−0.04) |
| MON-HT8 (SEQ ID NO: 37) | 0.46 (−0.02) | 0.11 (−0.02) | 0.11 (−0.01) | 0.14 (−0.05) |
| MON-HT9 (SEQ ID NO: 40) | 0.53 (−0.02) | 0.10 (−0.01) | NDB | NDB |
| MON-HT10 (SEQ ID NO: 43) | 0.78 (−0.05) | 0.13 (−0.03) | NDB | NDB |
| Wild-type RdpA | 1.38 (−0.06) | 0.27 (−0.03) | 0.10 (−0.01) | 0.03 (−0.01) |

Enzyme activity over a range of temperatures was analyzed in-depth for MON-HT1, MON-HT2, MON-HT7, and MON-HT8. These assays were conducted as described above. Quizalofop-P or 2,4-D was used as the substrate for these reactions and activity was normalized based on the activity of the wild-type enzyme at 25° C. The activity curves obtained are presented in FIG. 2B (with quizalofop-P as the substrate) and FIG. 2C (with 2,4-D as the substrate). Using quizalofop-P as the substrate, MON-HT55 was the most temperature sensitive, with a $T_{1/2}$ of 29° C. The wild-type enzyme had a $T_{1/2}$ of 38° C. MON-HTI and MON-HT8 were less temperature sensitive than the wild-type enzyme with a $T_{1/2}$ of 42° C. and 41° C., respectively, at which temperatures the wild-type enzyme is 90% inactive. MON-HT2 and MON-HT7 were much less temperature sensitive with a $T_{1/2}$ of 46° C. and 47° C., respectively, at which temperatures the wild-type enzyme is completely inactive. When 2,4-D was used as the substrate, the wild-type enzyme had a $T_{1/2}$ of 36° C. MON-HT2, MON-HT7, and MON-HT8 were all slightly more temperature sensitive with a lower $T_{1/2}$ than the wild-type enzyme. MON-HTI was slightly less temperature sensitive, with a $T_{1/2}$ about 1° C. higher than the wild-type enzyme.

A protein melting analysis was also conducted. For the protein melting determinations, purified enzyme was added to 96-well microtiter plates in standard storage buffer (30 mM Tris pH7.5, 150 mM NaCl) with or without 50 uM Fe2+ and 1.0 mM aKG. Protein unfolding was then detected with SYPRO® orange protein gel stain (Invitrogen™ catalog #S6651, Life Technologies, Grand Island, NY) in a BioRad CFX96™ Real time PCR machine (BioRad, Hercules, CA) with readings taken between 10° C. to 95° C. in 0.5° C. steps. The $T_{1/2}$ (here, the temperature where 50% of the protein was unfolded) is shown in Table 8. The wild-type enzyme showed stabilization with 50 uM Fe2+ and 1.0 mM aKG. In contrast, 50 uM Fe2+ and 1.0 mM aKG had little effect on the stability of any of the engineered proteins. MON-HT55, MON-HT3, MON-HT4, MON-HT6, and MON-HT10 had melting temperatures in the range of 41° C. to 48° C., which is below the melting temperature of the wild-type enzyme. MON-HT1, MON-HT2, MON-HT5, MON-HT7, MON-HT8, and MON-HT9 had melting temperatures between 58° C. and 67° C., which is 8° C. to 17° C. higher than the wild-type enzyme. For MON-HT7 and MON-HT1, the difference in melting point was 11° C. in buffer without Fe2+ and aKG and 8° C. in buffer with Fe2+ and aKG. This was surprising since there are only four amino acid differences between the two enzymes. This data on the melting point of the enzymes confirms that the engineered proteins have been optimized for protein stability at higher temperatures. This data also matches the enzyme activity assay results for the proteins conducted at different temperatures.

TABLE 8

| Protein | Buffer | Buffer plus Fe2+ and aKG |
|---|---|---|
| MON-HT55 (SEQ ID NO: 11) | 41° C. | 41° C. |
| MON-HT1 (SEQ ID NO: 14) | 56° C. | 59° C. |
| MON-HT2 (SEQ ID NO: 18) | 55° C. | 58° C. |
| MON-HT3 (SEQ ID NO: 22) | 46° C. | 48° C. |
| MON-HT4 (SEQ ID NO: 25) | 43° C. | 44° C. |
| MON-HT5 (SEQ ID NO: 28) | 60° C. | 61° C. |
| MON-HT6 (SEQ ID NO: 31) | 44° C. | 44° C. |
| MON-HT7 (SEQ ID NO: 34) | 67° C. | 67° C. |
| MON-HT8 (SEQ ID NO: 37) | 61° C. | 61° C. |
| MON-HT9 (SEQ ID NO: 40) | 61° C. | 60° C. |
| MON-HT10 (SEQ ID NO: 43) | 44° C. | 44° C. |
| Wild-type RdpA | 42° C. | 50° C. |

The enzyme activity of MON-HT protein variants with haloxyfop, fenoxaprop, fluazifop, and dichlorprop as substrates was determined using the enzyme activity assay conducted at 23° C. with purified enzyme. The activity was recorded as the maximum activity as a percentage of the wild-type enzyme's activity, which was set at 100%. Data are provided in Table 9. MON-HT55, MON-HT3, MON-HT4, MON-HT5, and MON-HT9 had maximum activities for all four substrates lower than, or equal to, the maximum activity of the wild-type enzyme with the same substrate. With haloxyfop as the substrate MON-HT1, MON-HT2, MON-HT7, and MON-HT10 had a maximum activity that was greater than that of the wild-type enzyme. With fenoxaprop as the substrate MON-HT1, MON-HT2, MON-HT6, MON-HT7, MON-HT8, and MON-HT10 had a maximum activity that was greater than that of the wild-type enzyme. With fluazifop as the substrate MON-HT2 and MON-HT7 had a maximum activity that was greater than that of the wild-type enzyme. With dichlorprop as the substrate MON-HT1, MON-HT7, and MON-HT8 had a maximum activity that was greater than that of the wild-type enzyme.

TABLE 9

| Protein | Haloxy-fop | Fenoxaprop | Fluazifop | Dichlor-prop |
|---|---|---|---|---|
| MON-HT55 (SEQ ID NO: 11) | 58 | 34 | 38 | 31 |
| MON-HT1 (SEQ ID NO: 14) | 134 | 175 | 67 | 175 |
| MON-HT2 (SEQ ID NO: 18) | 142 | 121 | 124 | 92 |
| MON-HT3 (SEQ ID NO: 22) | 67 | 83 | 60 | 100 |
| MON-HT4 (SEQ ID NO: 25) | 49 | 53 | 52 | 39 |

TABLE 9-continued

| Protein | Haloxy-fop | Fenoxaprop | Fluazifop | Dichlor-prop |
|---|---|---|---|---|
| MON-HT5 (SEQ ID NO: 28) | 100 | 92 | 46 | 36 |
| MON-HT6 (SEQ ID NO: 31) | 75 | 333 | 47 | 37 |
| MON-HT7 (SEQ ID NO: 34) | 193 | 210 | 161 | 210 |
| MON-HT8 (SEQ ID NO: 37) | 99 | 106 | 50 | 106 |
| MON-HT9 (SEQ ID NO: 40) | 91 | 67 | 41 | 19 |
| MON-HT10 (SEQ ID NO: 43) | 124 | 233 | 48 | 29 |
| Wild-type RdpA | 100 | 100 | 100 | 100 |

The enzyme identities were confirmed using mass spectroscopy. For this analysis, purified protein was separated on a PAGE gel and stained. The stained bands were then cut out, destained, and trypsin digested using standard protocols. Trypsin digested protein preparations were separated on a Dionox UltiMat® 3000 RSLCnano LC System (Thermo Scientific, Sunnyvale, CA) using a Thermo Scientific™ AQUASIL™ C-18 Javelin™ Guard column under standard conditions and injected for MS-MS analysis using a Thermo Scientific™ Q Exactive™ Hybrid Quadrupole-Orbitrap Mass Spectrometer (Thermo Scientific, Sunnyvale, CA).

To optimize proteins for increased activity in the presence of phenoxy acid herbicides, computational protein engineering was performed on the crystal structure for several of the engineered proteins. This was used to inform additional rounds of mutagenesis, performed as described previously but using the bacterial sequence, SEQ ID NO:15, encoding the protein sequence MON-HT1 (SEQ ID NO:14) as the starting sequence. Approximately 472 additional engineered proteins were generated. These were combined with the approximately 2600 engineered proteins described in Example 1 and Table 6 for a total of approximately 3072 engineered proteins to identify proteins optimized for activity in the presence of 2,4-D. The first screen of the new variants was the high-throughput (HTP) bacterial protein expression and enzyme assay system with crude bacterial lysates as described in Example 1, but modified to be conducted at the desired temperatures of 25° C. and 40° C. with the post-quenching color development done at 25° C. Following this HTP screen, approximately 34 engineered proteins were selected and advanced into screening with protein normalization across all of the samples. From this screen, 12 engineered proteins were selected and advanced to screening with purified protein assayed with the herbicide degradation enzyme assay as described in Example 1. Enzyme heat stability was assayed with limited protein melting assays. From this screen, 7 engineered proteins were selected and advanced for in plant testing. Three enzyme variants were selected for detailed characterization using purified protein, where the protein concentrations were normalized, and the screening included quizalofop-P and 2,4-D as substrates, as well as additional herbicides shown in Table 10 and Table 12 and protein melting characterization.

Kinetic analysis using a non-endpoint assay was conducted at 23° C. with either quizalofop-P or 2,4-D as substrate, as detailed above for purified protein of the wild-type enzyme, MON-HT1, MON-HT13, MON-HT15, and MON-HT17. The data demonstrate a significant and unexpected enhancement of enzymatic activity of MON-HT13, MON-HT15, and MON-HT17 relative to both the wild-type RdpA enzyme and the MON-HTI enzyme when tested with 2,4-D as a substrate. Specifically, all three variants showed a roughly 2.5 to 3-fold increase in activity (Vmax) relative to MON-HT1. Enzymatic activity of MON-HT13, MON-HT15, and MON-HT17 variants with quizalofop as the substrate was roughly similar to the activity of MON-HT1. See Table 10.

TABLE 10

| | Quizalofop | | 2,4-D | |
|---|---|---|---|---|
| Protein | Vmax | Km | Vmax | Km |
| Wild-type RdpA | 2.76 (0.11) | 0.09 (0.013) | 0.25 (0.01) | 0.13 (0.017) |
| MON-HT1 (SEQ ID NO: 14) | 1.62 (0.05) | 0.12 (0.012) | 1.17 (0.01) | 0.03 (0.002) |
| MON-HT13 (SEQ ID NO: 47) | 1.51 (0.05) | 0.12 (0.013) | 3.38 (0.05) | 0.08 (0.004) |
| MON-HT15 (SEQ ID NO: 49) | 1.52 (0.06) | 0.12 (0.017) | 3.53 (0.04) | 0.07 (0.004) |
| MON-HT17 (SEQ ID NO: 51) | 1.53 (0.05) | 0.14 (0.014) | 2.91 (0.04) | 0.07 (0.004) |

A protein melting analysis was conducted as detailed above. The melting temperatures of MON-HT13, MON-HT15, and MON-HT17 was similar to the melting temperature of MON-HT1 with $T_{1/2}$ in buffer in the range of 55-58° C., and with $T_{1/2}$ in buffer plus Fe2+ and aKG in the range of 60-62° C. These data indicate that the MON-HT13, MON-HT15, and MON-HT17 variants have a similar enzyme heat stability compared to MON-HT1. This data on the melting point of the enzyme variants confirms that the engineered proteins have been optimized for protein stability at higher temperatures. See Table 11.

TABLE 11

| | Melting temp ° C. | |
|---|---|---|
| Protein | Buffer | Buffer plus Fe2+ and aKG |
| Wild-type RdpA | 43 | 53 |
| MON-HT1 (SEQ ID NO: 14) | 58 | 62 |
| MON-HT13 (SEQ ID NO: 47) | 57 | 62 |
| MON-HT15 (SEQ ID NO: 49) | 55 | 60 |
| MON-HT17 (SEQ ID NO: 51) | 57 | 61 |

The enzyme activity of MON-HT protein variants with triclopyr, fluroxypyr, MCPA, MCPB, mecoprop, as substrates was determined using the enzyme activity assay conducted at 23° C. with purified enzyme. The activity was recorded as the maximum activity as a percentage of the wild-type RdpA enzyme's activity, which was set at 100%. Data are provided in Table 12. For each of the proteins assayed (MON-HT1, MON-HT13, MON-HT15, and MON-HT17) with the herbicides triclopyr and fluroxypyr as the substrate, there was detectable activity, especially in the engineered variants, but activity was not robust enough to quantify. There was no detectable activity for each of the proteins assayed (MON-HT1, MON-HT13, MON-HT15, and MON-HT17) with the herbicide MCPB as the substrate. The enzymatic activity with mecoprop as a substrate was reduced for each of the MON-HT1, MON-HT13, MON-HT15, and MON-HT17 variants compared to the wild-type RdpA enzyme. An unexpected result was that enzymatic activity with MCPA as a substrate was roughly 6-fold greater for MON-HT1, and approximately 10-fold greater for MON-HT13, MON-HT15, and MON-HT17 compared to the wild-type RdpA enzyme. See Table 12.

TABLE 12

| | Mecoprop | | MCPA | |
|---|---|---|---|---|
| Protein | Vmax | Km | Vmax | Km |
| Wild-type RdpA | 100 | 100 | 100 | 100 |
| MON-HT1 (SEQ ID NO: 14) | 63 | 142 | 600 | 21 |
| MON-HT13 (SEQ ID NO: 47) | 37 | 92 | 1800 | 68 |
| MON-HT15 (SEQ ID NO: 49) | 25 | 57 | 1300 | 59 |
| MON-HT17 (SEQ ID NO: 51) | 27 | 65 | 1400 | 62 |

Example 4

Expression of Optimized Engineered Proteins in Maize

Ten unique engineered proteins optimized for activity at higher temperatures were selected for maize transformation and analysis in plants. DNA constructs were produced for expressing these engineered proteins with codon usage optimized for monocot expression using methods known to those skilled in the art. Enhancers, promoters, leaders, introns, CTPs, and 3'UTRs were tested in various combinations with the engineered proteins in these DNA constructs. The DNA constructs were used to transform immature maize (LH244) embryos with these vectors using Agrobacterium tumifaciens and standard methods known in the art. Regenerated R0 transgenic plantlets were grown in the green house.

Transgenic R0 maize plants were screened by the application of quizalofop-P (2×) plus 2,4-D (2×) at 7 to 10 days following transplant into plugs (generally corresponding to V3-V4 growth stage). All constructs tested produced plants containing unique events that passed the RO screen. The R0 plants were selfed to generate R1 homozygous seed and the R0 was also used as the male to cross with inbred plants containing maize event MON89034 to generate segregating F1 hybrid seed for efficacy field trials.

An efficacy field trial was conducted with segregating F1 hybrid plants, with 50% hemizygous and 50% null for the transgene. Tolerance to quizalofop-P (2×) plus 2,4-D (2×) was assessed using two herbicide application regimens: (1) quizalofop-P (Assure II) at 0.16 lb ai/acre (2×) plus 0.25% v/v non-ionic surfactant (NIS) applied at VE-V2 growth stage followed by the same at V4 growth stage followed by the same at V8 growth stage and (2) 2,4-D amine at 2 lb ae/acre (2×) plus quizalofop-P at 0.04 lb ai/acre (0.5×) plus 0.25% v/v NIS applied at VE-V2 growth stage followed by 2,4-D amine at 2 lb ae/acre (2×) plus 0.25% v/v NIS applied at V4 growth stage followed by the same at V8 growth stage. The 50% of the plants that were null for transgene were removed by the first quizalofop-P application at VE-V2 growth stage. Plots were visually rated 10-14 days after application for crop injury on a scale of 0 to 100 with "0" being none and "100" being complete crop destruction. Table 13 shows the average injury rating at V4 and V8 growth stages for both spray regimens. Injury ratings of <10% were considered very good tolerance and injury ratings of <20% were considered good to fair tolerance. The percentage injury rating with 2× application of 2,4-D at V8 growth stage ranged from a high of 40% to a low of 0. Similarly, the percentage injury rating with 2× application of quizalofop-P at V8 growth stage ranged from a high of 90% to a low of 0. Variation in injury rating between plants expressing the same protein is likely due to variations in construct design or transgene insertion location. This data confirmed that plants expressing the engineered proteins exhibited tolerance to 2,4-D and quizalofop herbicide application at the 2× rate.

TABLE 13

| Protein | CTP | % Injury from V4 Quizalofop | % Injury from V8 Quizalofop | % Injury from V4 2,4-D | % Injury from V8 2,4-D |
|---|---|---|---|---|---|
| MON-HT1 | A | 8.33 | 8.33 | 7.5 | 5.83 |
| MON-HT1 | None | 7.14 | 7.86 | 12.86 | 10.71 |
| MON-HT1 | B | 7.5 | 8.75 | 10 | 10 |
| MON-HT1 | C | 0.45 | 0.91 | 14.09 | 11.36 |
| MON-HT2 | A | 0 | 0 | 20 | 34.17 |
| MON-HT2 | None | 0 | 0 | 20 | 33.75 |
| MON-HT2 | B | 11.67 | 11.67 | 10.56 | 13.33 |
| MON-HT2 | C | 14.33 | 14.33 | 12 | 12 |
| MON-HT3 | A | 1.6 | 0.5 | 21.7 | 9.2 |
| MON-HT4 | A | 6.1 | 0 | 22.3 | 12.3 |
| MON-HT5 | A | 6.8 | 1.7 | 27.2 | 17.4 |
| MON-HT6 | A | 8 | 1.7 | 27 | 12.7 |
| MON-HT7 | A | 31.2 | 5 | 21.6 | 16.6 |
| MON-HT8 | A | 1.25 | 1.25 | 10 | 10 |
| MON-HT8 | None | 85 | 90 | 0 | 0 |
| MON-HT8 | B | 9.17 | 8.33 | 12.5 | 11.67 |
| MON-HT8 | C | 30 | 32.5 | 20 | 21.25 |
| MON-HT9 | A | 5 | 5 | 20 | 40 |
| MON-HT10 | A | 0 | 0 | 28 | 38.33 |
| MON-HT3 + MON-HT1 | A + none | 6.67 | 5.56 | 20.56 | 18.89 |
| MON-HT4 + MON-HT8 | A + none | 11.25 | 11.88 | 9.38 | 4.38 |

Figure 4A:
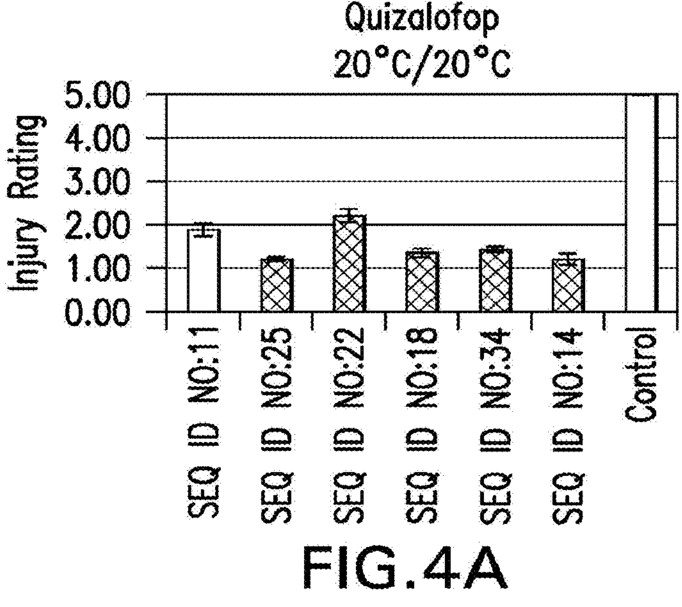
FIGS. 4A-4E. The average injury rating after 2× quizalofop-P (0.16 lb ai/acre) (4A, 4B, and 4C) or 4× 2,4-D (4 lb ac/acre) (4D and 4E) application to F1 hybrid maize plants (homozygous R1 expressing MON-HT×MON89034 inbred) expressing MON-HT55 (SEQ ID NO: 11), MON-HT 1 (SEQ ID NO:14), MON-HT2 (SEQ ID NO:18), MON-HT3 (SEQ ID NO:22), MON-HT4 (SEQ ID NO:25), MON-HT7 (SEQ ID NO:34), or F1 hybrid control (NK603× MON89034). Data from plants acclimated at daytime and night time temperatures set at 20° C. (20° C./20° C.) prior to application of 2× quizalofop-P (FIG. 4A) or 4× 2,4-D (FIG. 4D)
Figure 4B:
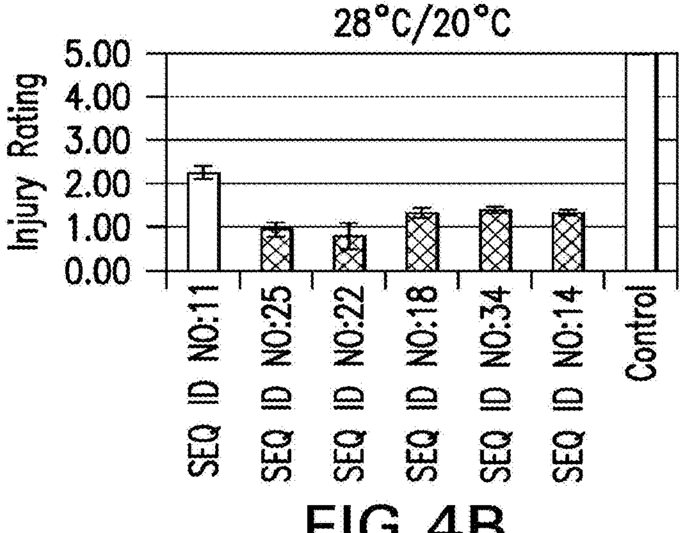
Figure 4C:
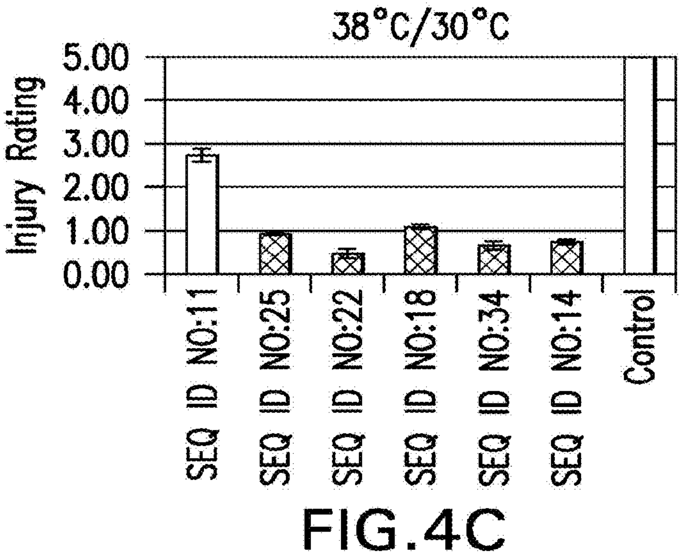

A plant-based enzyme activity assay for heat sensitivity was used to determine the effect of elevated growth temperatures on the herbicide tolerance of transgenic plants containing the optimized engineered proteins. To test for quizalofop-P tolerance at elevated growth temperatures, F1 hybrid (produced by crossing an R1 homozygous plant expressing one of the MON-HT proteins with inbred maize event MON89034) maize seed was grown in a growth chamber for 10 days at a day temperature of 28° C. and a night temperature of 20° C. with 50% humidity. After 10 days, the plants were moved to acclimate for 3 days at one of three different day and night temperature regimens: (1)

both day and night temperatures set at 20° C.; (2) day temperature at 28° C. and night temperature at 20° C.; or (3) day temperature at 38° C. and night temperature at 30° C. At the end of the acclimation period, the plants were generally at V4 growth stage and were sprayed with 2× quizalofop-P. Ten days post treatment the plants were scored for injury on a rating scale of 1 to 5 where '0' is no visible injury observed, '1' is chlorotic speckling, '2' is chlorotic streaking, '3' there are leaf gaps or tears, '4' are plants with stunted growth and/or twisted leaves, and '5' are dead plants or no growth observed. Results are presented in FIG. 4. F1 hybrid maize plants expressing MON-HT55 showed good tolerance (injury ratings of around 2) to the spray treatments when day/night temperatures were 20° C./20° C. (FIG. 4A) or 28° C./20° C. (FIG. 4B) relative to the F1 hybrid control plants (maize events NK603 × MON89034) (injury rating of 5). When the day/night temperatures were 38° C./30° C. F1 hybrid control plants had an injury rating of 5, F1 hybrid plants expressing MON-HT55 had an average injury rating of 3, and F1 hybrid plants expressing MON-HT1, MON-HT2, MON-HT3, MON-HT4, or MON-HT7 had injury ratings of ≤ 1 (FIG. 4C). The engineered proteins optimized for activity in higher temperatures provided AOPP herbicide tolerance when plants expressing these engineered proteins were exposed to high temperatures.

Figure 4D:
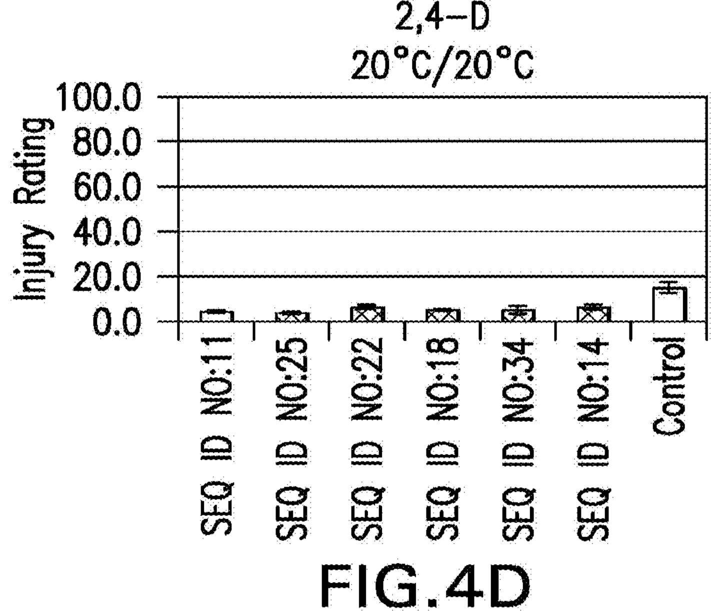
Figure 4E:
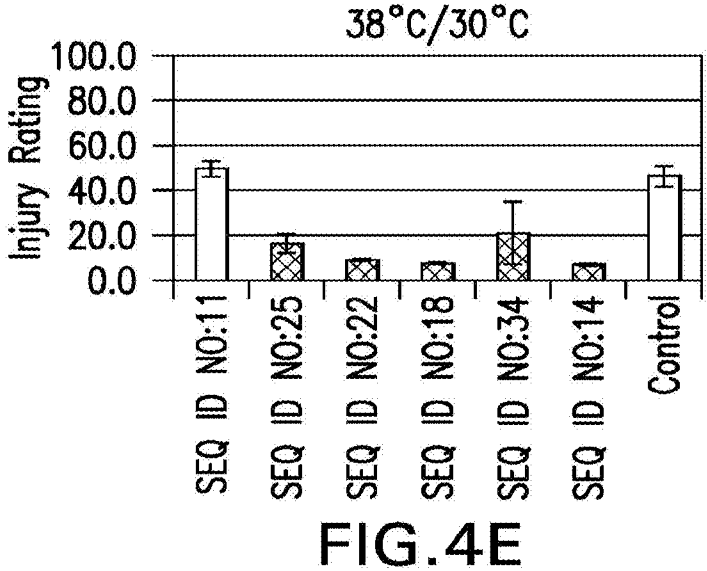

To test for 2,4-D tolerance at elevated growth temperatures, F1 hybrid plants were produced by crossing an R1 plant containing MON-HTI, MON-HT2, MON-HT3, MON-HT4, MON-HT7, or MON-HT55 with an inbred plant containing maize event MON89034. The F1 hybrid plants were grown in a greenhouse for one week at a minimum temperature of 20° C. and a maximum temperature of 28° C. with 50 to 80% humidity. After 1 week, the plants were moved to acclimate for three days at one of two different day and night temperature regimens: (1) both day and night temperatures set at 20° C. or (2) day temperature at 38° C. and night temperature at 30° C. At the end of the acclimation period, the plants were generally at V4 growth stage and were sprayed with 4× 2,4-D amine. Ten days after treatment the plants were scored for injury using an injury scale of 0 to 100 with "0" being no injury and "100" being a dead plant. When plants were acclimated at day/night temperatures of 20° C./20° C. prior to application of 4× 2,4-D amine, F1 plants containing MON-HT1, MON-HT2, MON-HT3, MON-HT4, MON-HT7, or MON-HT55 had injury rating averages of <10%, and the control plants had injury rating averages of <20% (FIG. 4D). When plants were acclimated at day/night temperatures of 38° C./30° C. prior to application of 4× 2,4-D amine, F1 plants containing MON-HT4 or MON-HT7 had injury rating averages of <20%, F1 plants containing MON-HT1, MON-HT2 or MON-HT3 had injury rating averages of <10% (FIG. 4E), and the control plants and plants containing MON-HT55 F1 plants had injury rating averages of 50% (FIG. 4E). These results demonstrated that the engineered proteins optimized for activity in higher temperatures provided 2,4-D herbicide tolerance when plants expressing these engineered proteins were exposed to high temperatures.

Separate trait efficacy field trials for quizalofop-P and 2,4-D were conducted at two locations cach with F1 hybrid transgenic plants produced by crossing an inbred plant containing maize event MON89034 with an R1 plant containing MON-HT55 (with a CTP), MON-HTI (with or without a CTP), MON-HT2 (with or without a CTP), MON-HT3 (with a CTP), MON-HT4 (with a CTP), MON-HT5 (with a CTP), MON-HT6 (with a CTP), or MON-HT7 (with a CTP). Transgenic F1 hybrid plants containing maize events NK603×MON89034 were used for comparison as a control.

In the efficacy field trial for quizalofop-P tolerance and clethodim sensitivity, one of four herbicide treatments was used: (1) quizalofop-P (Assure II) at 0.32 lb ai/acre (4×) plus 0.25% v/v non-ionic surfactant (NIS) applied at VE-V2 growth stage followed by the same at V4 growth stage followed by the same at V8 growth stage; (2) quizalofop-P at 0.64 lb ai/acre (8×) plus 0.25% v/v NIS applied at VE to V2 growth stage followed by the same at V4 growth stage followed by the same at V8 growth stage; (3) quizalofop-P at 1.28 lb ai/acre (16×) plus 0.25% v/v NIS applied at VE to V2 growth stage followed by the same at V4 growth stage followed by the same at V8growth stage; or (4) clethodim at 0.25 lb ai/acre (1×) plus 0.25% v/v NIS applied at V8 growth stage. Plots were visually rated 10-14 days after application for crop injury on a scale of 0 to 100with "0" being none and "100" being complete crop destruction. Tables 14 and 15 show the average injury ratings after herbicide application at V4 or V8 growth stage, respectively.

Plants containing MON-HTI, MON-HT2, MON-HT3, MON-HT4, MON-HT5, MON-HT6, or MON-HT7 (all operably linked to a CTP) showed very good tolerance to quizalofop-P with injury ratings of less than 15% across all application rates and at both V4 and V8 growth stages. Plants containing MON-HT55 operably linked to a CTP showed moderate to poor tolerance with injury ratings from 0.8% to 78.8%. The injury ratings for the control plants after quizalofop-P application were 99.5%. These results indicate that plants containing MON-HTI, MON-HT2, MON-HT3, MON-HT4, MON-HT5, MON-HT6, or MON-HT7 operably linked to a CTP had very good tolerance to sequential applications of quizalofop-P.

Figure 5A:
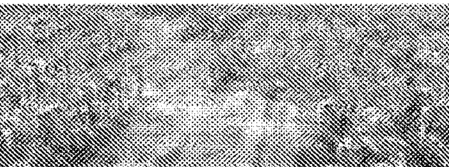
FIGS. 5A-5B.
Figure 5A:
Figure 5B:
Figure 6A:
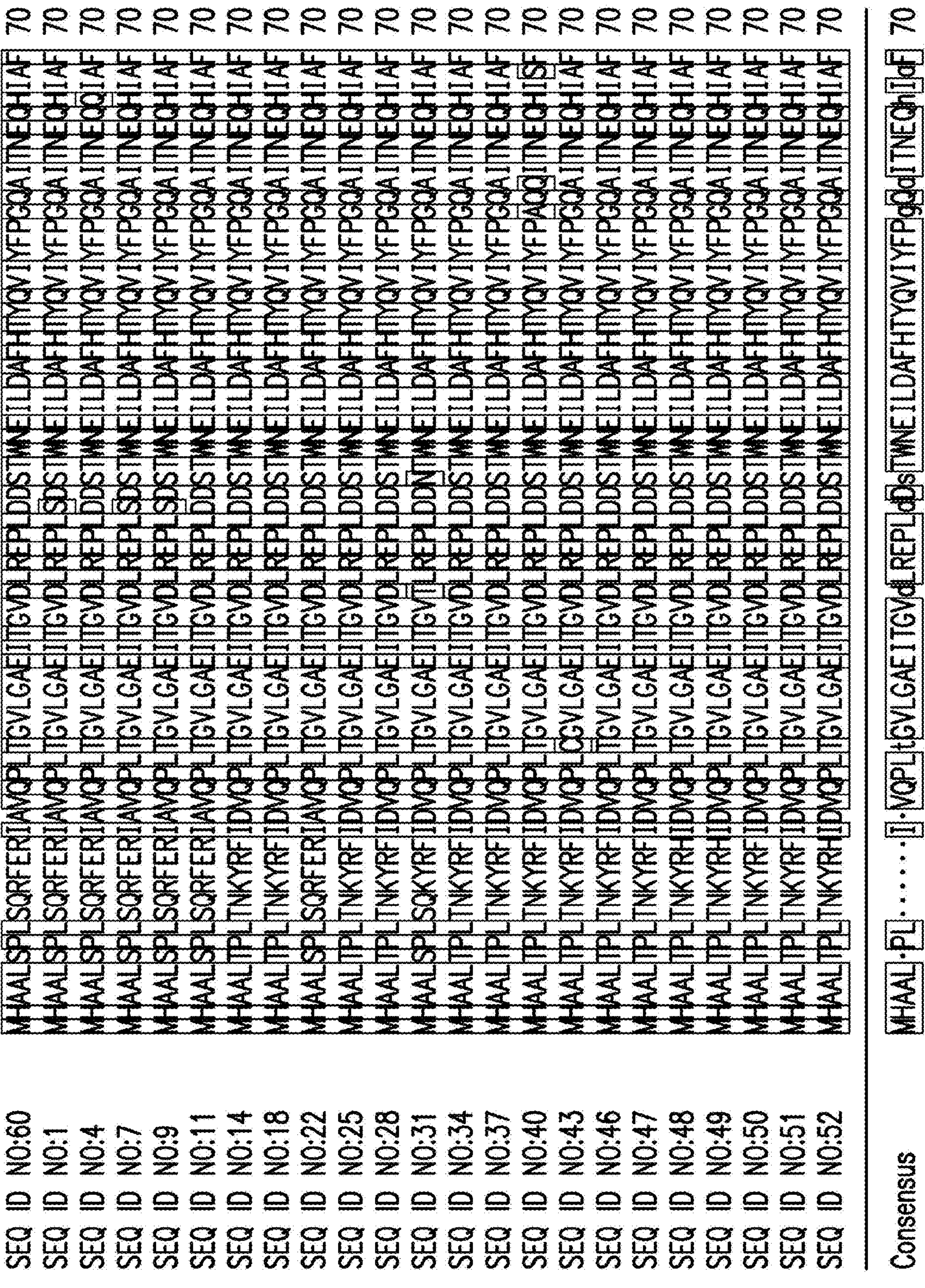
FIGS. 6A-6E. Multi-sequence alignment of protein sequences for wild-type RdpA from *S. herbicidovorans* (SEQ ID NO:60) and SEQ ID NO:1, 4, 7, 9, 11, 14, 18, 22, 25, 28, 31, 34, 37, 40, 43, and 46-52 with the consensus sequence (provided as SEQ ID NO:61) provided at the bottom of each of FIGS. 6A, 6B, 6C, 6D, 6E.
Figure 6B:
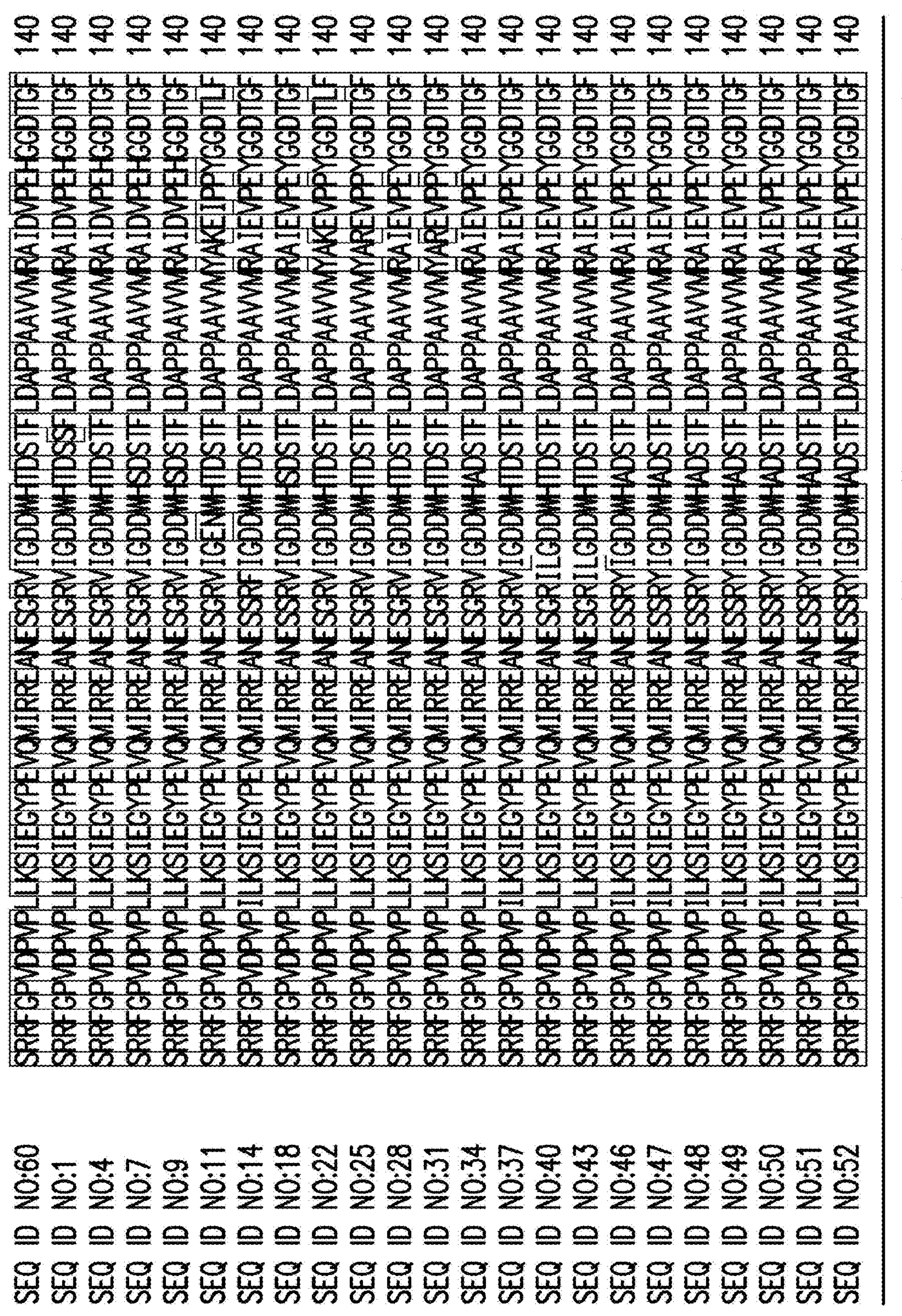
Figure 6C:
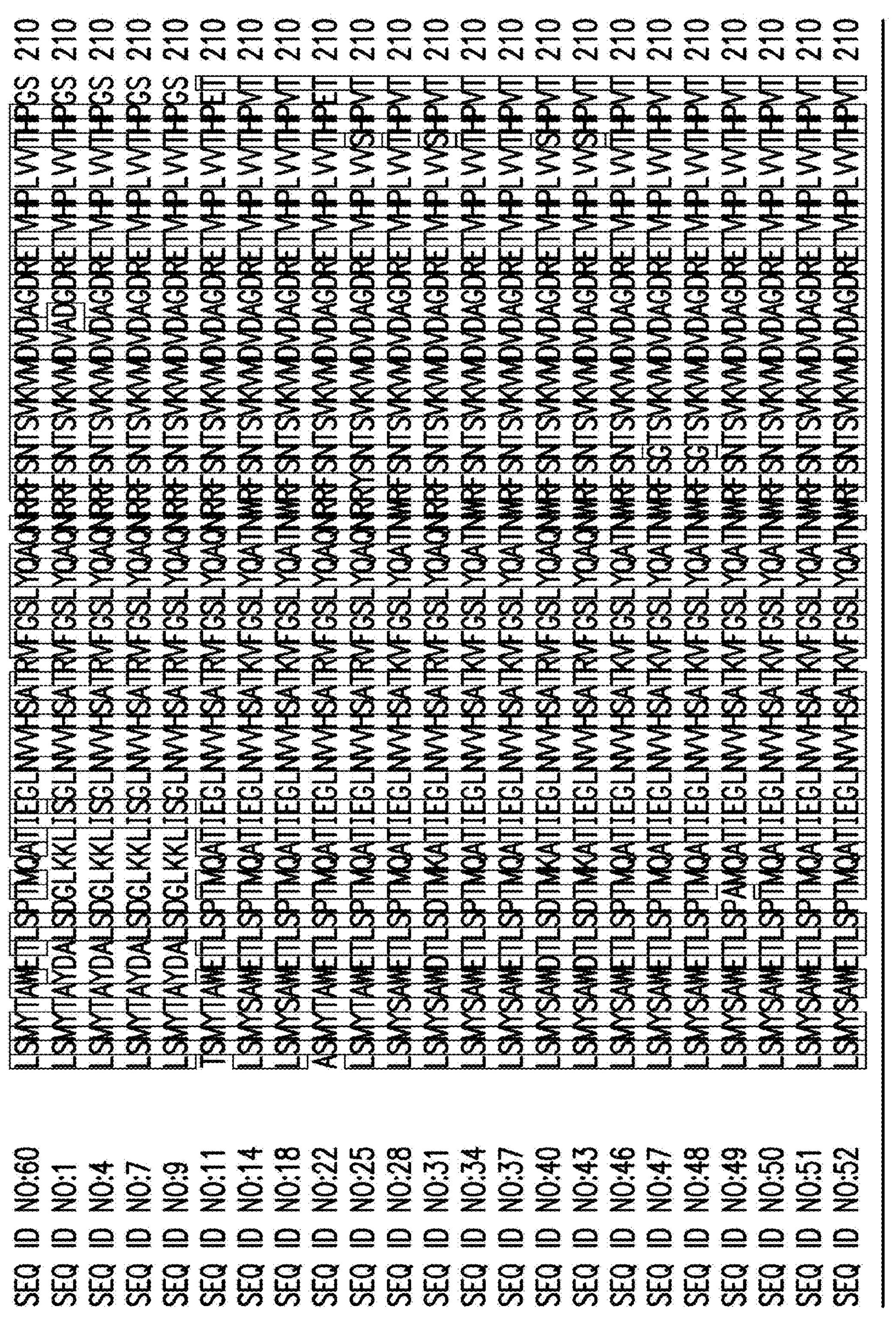
Figure 6D:
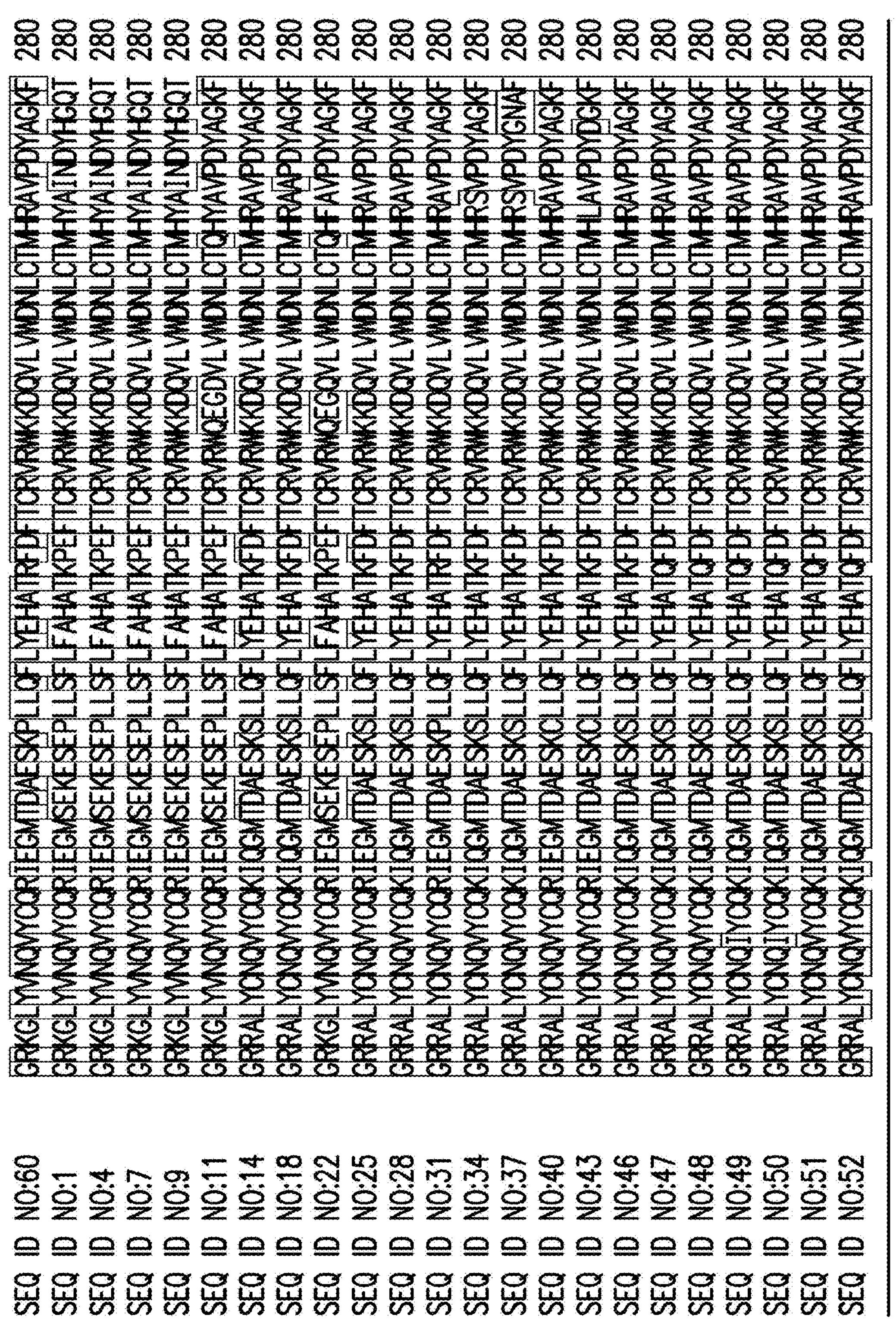
Figure 6E:

Plants containing MON-HTI or MON-HT2 with an operably linked CTP had better tolerance to quizalofop-P than plants containing MON-HTI or MON-HT2 without an operably linked CTP. Plants containing MON-HTI with an operably linked CTP had 0 to 5.5% injury rating across all quizalofop-P applications compared to the 3.3% to 18.8% injury ratings of plants containing MON-HTI without an operably linked CTP. Plants containing MON-HT2 with an operably linked CTP had 1.5% to 10% injury rating across all quizalofop-P applications compared to the 16.3% to 82.5% injury ratings of plants containing MON-HT2 without an operably linked CTP. FIG. 5 shows plants containing MON-HT2 operably linked to a CTP (FIG. 5A) and plants containing MON-HT2 without a CTP (FIG. 5B) 10 to 14 days after quizalofop-P application (treatment 3) at 1.28 lb ai/acre (16×) plus 0.25% v/v NIS applied at VE to V2 growth stage followed by the same at V4 growth stage followed by the same at V8 growth stage. The control plants did not survive, the plants containing MON-HT2 without a CTP had moderate to poor tolerance, and the plants containing the MON-HT2 operably linked to a CTP had robust tolerance to the quizalofop-P application. These results confirmed that the use of an operably linked CTP greatly improves quizalofop-P tolerance.

All transgenic plants had injury ratings above 90% to an application of 1× clethodim (0.25 lb ai/acre) applied at the V8 growth stage, demonstrating the use of this herbicide for volunteer control in transgenic plants containing the engineered proteins.

In the efficacy field trial for 2,4-D tolerance, one of four herbicide treatments was used: (1) 2,4-D amine at 2 lb ac/acre (2×) plus 0.25% v/v non-ionic surfactant (NIS) applied to VE to V2 followed by V4 followed by V8; (2)

2,4-D amine at 4 lb ac/acre (4×) plus 0.25% v/v NIS applied to VE to V2 followed by V4 followed by V8; (3) 2,4-D amine at 8 lb ac/acre (8×) plus 0.25% v/v NIS applied to VE to V2 followed by V4 followed by V8 maize; or (4) 2,4-D amine at 16 lb ac/acre (16×) plus 0.25% v/v NIS applied to VE to V2 followed by V4 followed by V8. Plots were visually rated as above. Tables 14 and 15 show the average injury ratings after herbicide application at V4 or V8 growth stage, respectively.

Plants containing MON-HT1, MON-HT2, or MON-HT6 (all operably linked to a CTP) showed very good tolerance to 2,4-D with injury ratings of less than 10% and less than 17% across all application rates at V4 and V8 growth stages, respectively. Plants containing MON-HT3, MON-HT4, MON-HT5, or MON-HT7 (all operably linked to a CTP) showed good tolerance to 2,4-D with injury ratings of less than 20% and less than 22% across all application rates at V4 and V8 growth stages, respectively. Plants containing MON-HT55 operably linked to a CTP showed moderate to poor tolerance with injury ratings from 7.5% to 66%. The injury ratings for the control plants after 2,4-D application ranged from 40% to 82.2%. These results indicate that plants containing MON-HT1, MON-HT2, MON-HT3, MON-HT4, MON-HT5, MON-HT6, or MON-HT7 had good tolerance to sequential applications of 2,4-D.

Plants containing MON-HTI or MON-HT2 with an operably linked CTP in general did not show the marked differences in tolerance to 2,4-D compared to plants containing MON-HTI or MON-HT2 without an operably linked CTP as was seen with the quizalofop-P application.

Plants containing MON-HT1 with an operably linked CTP had 0 to 16.3% injury rating across all 2,4-D applications compared to the 0 to 13.8% injury ratings of plants containing MON-HT1 without an operably linked CTP. Plants containing MON-HT2 with an operably linked CTP had 1.3% to 15% injury rating across all 2,4-D applications compared to the 1.3% to 21.3% injury ratings of plants containing MON-HT2 without an operably linked CTP. However, the difference was notable after 2,4-D application at V4 growth stage for plants containing MON-HT2 with an operably linked CTP (4.5% injury rating at 8× and 7.5% at 16×) compared to plants without the CTP (13.75% injury rating at 8× and 21.25% at 16×).

TABLE 14

| V4 Growth Stage | 2x 2,4-D | 4x 2,4-D | 8x 2,4-D | 16x 2,4-D | 4x Quizalofop | 8x Quizalofop | 16x Quizalofop |
|---|---|---|---|---|---|---|---|
| Control | 52.5 | 64.4 | 73.8 | 74.7 | 99.5 | 99.5 | 99.5 |
| MON-HT55 | 30.0 | 41.3 | 43.8 | 66.3 | 37.5 | 67.5 | 77.5 |
| MON-HT55 | 20.0 | 23.1 | 50.0 | 55.0 | 12.5 | 43.8 | 62.5 |
| MON-HT55 | 15.0 | 30.0 | 58.8 | 53.8 | 2.0 | 7.5 | 20.0 |
| MON-HT55 | 12.5 | 30.0 | 48.8 | 52.5 | 8.0 | 18.8 | 48.8 |
| MON-HT55 | 13.8 | 31.3 | 45.0 | 61.3 | 6.0 | 10.0 | 21.3 |
| MON-HT55 | n/a | n/a | n/a | n/a | 0.8 | 13.8 | 16.3 |
| MON-HT55 | 7.5 | 22.5 | 53.8 | 63.8 | 5.5 | 12.5 | 13.8 |
| MON-HT1 (no CTP) | 0.0 | 0.0 | 5.8 | 12.5 | 5.8 | 11.3 | 18.8 |
| MON-HT1 | 0.0 | 0.0 | 5.0 | 6.3 | 0.0 | 0.8 | 4.5 |
| MON-HT2 (no CTP) | 1.3 | 2.5 | 13.8 | 21.3 | 42.5 | 76.3 | 82.5 |
| MON-HT2 | 1.3 | 0.0 | 4.5 | 7.5 | 1.5 | 0.8 | 10.0 |
| MON-HT3 | 3.8 | 6.3 | 8.8 | 11.3 | 0.8 | 0.0 | 4.3 |
| MON-HT4 | 0.0 | 1.3 | 8.8 | 18.8 | 2.8 | 3.3 | 13.8 |
| MON-HT5 | 2.5 | 2.5 | 7.5 | 17.5 | 1.3 | 4.5 | 4.5 |
| MON-HT6 | 0.0 | 2.0 | 5.8 | 8.8 | 0.0 | 1.3 | 2.8 |
| MON-HT7 | 1.3 | 1.3 | 5.8 | 12.5 | 0.8 | 1.3 | 3.3 |

TABLE 15

| V8 Growth Stage | 1x Clethodim | 2x 2,4-D | 4x 2,4-D | 8x 2,4-D | 16x 2,4-D | 4x Quizalofop | 8x Quizalofop | 16x Quizalofop |
|---|---|---|---|---|---|---|---|---|
| Control | 93.6 | 40.0 | 52.8 | 64.1 | 82.2 | 99.5 | 99.5 | 99.5 |
| MON-HT55 | 93.3 | 16.3 | 28.8 | 36.3 | 55.0 | 25.0 | 45.0 | 78.8 |
| MON-HT55 | 93.3 | 14.4 | 20.0 | 39.4 | 56.9 | 10.0 | 31.3 | 41.3 |
| MON-HT55 | 93.3 | 11.3 | 16.3 | 30.0 | 47.5 | 3.8 | 3.8 | 16.3 |
| MON-HT55 | 93.3 | 11.3 | 20.0 | 35.0 | 47.5 | 3.8 | 20.0 | 38.8 |
| MON-HT55 | 94.5 | 15.0 | 18.8 | 33.8 | 57.5 | 4.3 | 5.0 | 18.8 |
| MON-HT55 | 93.3 | n/a | n/a | n/a | n/a | 2.5 | 6.3 | 18.8 |
| MON-HT55 | 94.5 | 12.5 | 13.8 | 36.3 | 52.5 | 2.0 | 5.5 | 11.8 |
| MON-HT1 (no CTP) | 94.5 | 2.5 | 4.0 | 8.8 | 13.8 | 3.3 | 7.5 | 16.3 |
| MON-HT1 | 93.3 | 1.3 | 1.5 | 8.3 | 16.3 | 2.0 | 2.0 | 5.5 |
| MON-HT2 (no CTP) | 92.0 | 5.0 | 8.8 | 13.8 | 25.0 | 16.3 | 52.5 | 77.5 |
| MON-HT2 | 93.3 | 2.5 | 3.3 | 10.0 | 15.0 | 2.5 | 3.8 | 4.8 |
| MON-HT3 | 94.5 | 5.5 | 5.5 | 11.3 | 13.8 | 2.5 | 2.0 | 6.0 |
| MON-HT4 | 94.5 | 2.0 | 8.8 | 12.5 | 21.3 | 3.3 | 3.3 | 8.0 |
| MON-HT5 | 92.0 | 3.3 | 4.0 | 10.0 | 21.3 | 2.5 | 0.0 | 8.0 |
| MON-HT6 | 93.3 | 6.3 | 4.3 | 11.3 | 12.5 | 1.3 | 2.0 | 5.0 |
| MON-HT7 | 93.3 | 2.0 | 2.8 | 9.3 | 20.0 | 1.5 | 0.8 | 5.5 |

Example 5

Evaluation of Chloroplast Targeting Peptides on Expression of Optimized Engineered Proteins in Maize To evaluate different chloroplast targeting peptides (CTP), plant transformation vectors were constructed, each comprising a recombinant DNA molecule optimized for monocot expression and encoding MON-HTI (SEQ ID NO: 16), MON-HT2 (SEQ ID NO:20), and MON-HT8 (SEQ ID NO:39), MON-HT9 (SEQ ID NO:42), or MON-HT10 (SEQ ID NO:45). The vectors were created using the same combination of promoter, leader, intron, and 3'-UTR, but with one of three separate CTPs (A, B, or C) or without a CTP operably linked to the protein-coding sequence. See Table 16. The DNA constructs were used to transform immature maize (LH244) embryos using Agrobacterium tumifaciens and standard methods known in the art. Regenerated RO transgenic plantlets were grown in the green house. The R0 plants were selfed to generate R1 homozygous seed. The R0 plants were also used as the male to cross with inbred plants containing maize event MON89034 to generate segregating F1 hybrid seed for trait efficacy field trials.

Separate trait efficacy field trials for quizalofop-P and 2,4-D were conducted at two locations each with the homozygous inbred transgenic plants (R2 or R4 generation). In these field trials, one of two herbicide treatments was used: (1) quizalofop-P (Assure II) at 0.16 lb ai/acre (2×) plus 0.25% v/v non-ionic surfactant (NIS) applied at V4 growth stage followed by the same at V8 growth stage; or (2) 2,4-D amine at 2 lb ae/acre (2×) plus 0.25% v/v non-ionic surfactant (NIS) applied to V4 followed by V8. Injury ratings (crop injury percentage at V4 (CIPV4) or V8 (CIPV8)) were taken 10 to 14 days after the V4 and V8 applications. Error was calculated using LSD (0.05). The results demonstrated that these plants had tolerance to 2× sequential applications of either quizalofop-P or 2,4-D with injury ratings below 10% following V4 and V8 applications. See Table 16.

TABLE 16

| | | 2X Quizalofop-P | | 2X 2,4-D | |
|---|---|---|---|---|---|
| Protein | CTP | CIPV4 LSD (0.05) = 1.45 | CIPV8 LSD (0.05) = 2.2 | CIPV4 LSD (0.05) = 0.95 | CIPV8 LSD (0.05) = 1.6 |
| MON-HT1 | A | 0 | 2.125 | 0 | 2.5 |
| MON-HT1 | B | 0 | 1.75 | 0 | 1.25 |
| MON-HT1 | C | 0 | 1.75 | 1.25 | 1.25 |
| MON-HT1 | no CTP | 0 | 1.25 | 0 | 1.25 |
| MON-HT2 | A | 0 | 1.875 | 0.875 | 1.25 |
| MON-HT2 | B | 0 | 0 | 0 | 2.5 |
| MON-HT2 | C | 0 | 2 | 0 | 1.25 |
| MON-HT2 | no CTP | 1.25 | 3.5 | 0 | 2.5 |
| MON-HT8 | A | 0 | 1.25 | 1.75 | 1.25 |
| MON-HT8 | B | 0.75 | 2.5 | 0 | 1.25 |
| MON-HT8 | C | 0 | 1.25 | 1.25 | 0 |
| MON-HT9 | A | 0 | 0 | 3.75 | 1.25 |
| MON-HT10 | A | 0 | 0 | 0 | 1.25 |

Leaf samples were collected from the plants containing transgene cassettes encoding MON-HT1, MON-HT2, and MON-HT8 with and without CTP sequences to determine expression of the mRNA transcribed from the transgene cassette encoding the engineered proteins. Quantigene® analysis was done on the leaf sample extracts to determine mRNA expression of the transgene cassette. For these assays, the probe was to the common 3'-UTR sequence present in each expression cassette used to generate the transgenic plants. Relative expression was calculated by normalizing to maize housekeeping genes. A leaf sample was collected from each of eight plants for each construct configuration used to make the transgenic plants, and the reported relative mRNA expression data is an average of the eight samples with standard error.

Plants containing the transgene construct encoding either MON-HT1 (SEQ ID NO:14) or MON-HT2 (SEQ ID NO:18) had higher relative transgene mRNA expression for constructs containing either the 'A' or 'B' CTP than for constructs without a CTP or with the 'C' CTP. Plants containing the transgene construct encoding MON-HT8 (SEQ ID NO:37) had similar high relative transgene mRNA expression for constructs containing any of the three CTPs (A, B, or C). See Table 17.

TABLE 17

| MON-HT variant | CTP | Relative Expression | Standard Error |
|---|---|---|---|
| MON-HT1 | A | 7.80 | 1.20 |
| MON-HT1 | B | 5.95 | 1.63 |
| MON-HT1 | C | 3.82 | 0.44 |
| MON-HT1 | no CTP | 4.31 | 0.68 |
| MON-HT2 | A | 6.96 | 0.66 |
| MON-HT2 | B | 6.16 | 0.65 |
| MON-HT2 | C | 4.11 | 0.29 |
| MON-HT2 | no CTP | 4.66 | 0.45 |
| MON-HT8 | A | 8.06 | 0.48 |
| MON-HT8 | B | 7.62 | 0.46 |
| MON-HT8 | C | 4.87 | 0.47 |
| LH244 Control | none | 0.00 | 0.00 |

Separate trait efficacy field trials for quizalofop-P and 2,4-D pressure screening were conducted at one location each with F1 hybrid transgenic plants produced by crossing an inbred plant containing maize event MON89034 with an R1 plant containing MON-HT1, MON-HT2, MON-HT8, MON-HT9, and MON-HT10 with and without operably linked CTP sequences. Transgenic F1 hybrid plants containing maize events NK603×MON89034 were used for comparison as a control.

In the trait efficacy field trial for quizalofop-P tolerance, one of three herbicide treatments was used: (1) quizalofop-P (Assure II) at 0.32 lb ai/acre (4×) plus 0.25% v/v non-ionic surfactant (NIS) applied at VE-V2 growth stage followed by the same at V4 growth stage followed by the same at V8 growth stage; (2) quizalofop-P at 0.64 lb ai/acre (8×) plus 0.25% v/v NIS applied at VE-V2 growth stage followed by the same at V4 growth stage followed by the same at V8 growth stage; or (3) quizalofop-P at 1.28 lb ai/acre (16×) plus 0.25% v/v NIS applied at VE-V2 growth stage followed by the same at V4 growth stage followed by the same at V8 growth stage. Plots were visually rated as above. Table 18 shows the average injury ratings after herbicide application at V4 (CIPV4) or V8 (CIPV8) growth stage, respectively. The injury rating for the control plants after all quizalofop-P application was 100%. Error was calculated using LSD (0.05).

TABLE 18

| | | 4X Qizalofop-P | | 8X Qizalofop-P | | 16X Qizalofop-P | |
|---|---|---|---|---|---|---|---|
| MON-HT variant | CTP | CIPV4 LSD (0.05) = 1.92 | CIPV8 LSD (0.05) = 2.3 | CIPV4 LSD (0.05) = 4.7 | CIPV8 LSD (0.05) = 5.3 | CIPV4 LSD (0.05) = 5.0 | CIPV8 LSD (0.05) = 5.4 |
| none | none | 100 | 100 | 100 | 100 | 100 | 100 |
| MON-HT1 | A | 0 | 7.5 | 2.5 | 10 | 5 | 15 |
| MON-HT1 | B | 2.5 | 5 | 2.5 | 7.5 | 2.5 | 20 |
| MON-HT1 | C | 0 | 5 | 2.5 | 10 | 5 | 20 |
| MON-HT1 | no CTP | 2.5 | 10 | 10 | 22.5 | 22.5 | 37.5 |
| MON-HT2 | A | 0 | 5 | 2.5 | 7.5 | 5 | 15 |
| MON-HT2 | B | 0 | 5 | 0 | 10 | 0 | 20 |
| MON-HT2 | C | 0 | 5 | 5 | 12.5 | 12.5 | 20 |
| MON-HT2 | no CTP | 35 | 45 | 50 | 37.5 | 70 | 55 |
| MON-HT8 | A | 15 | 15 | 37.5 | 35 | 60 | 50 |
| MON-HT8 | B | 5 | 7.5 | 32.5 | 35 | 27.5 | 30 |
| MON-HT8 | C | 55 | 45 | 75 | 55 | 85 | 72.5 |
| MON-HT9 | A | 0 | 5 | 2.5 | 15 | 7.5 | 20 |
| MON-HT10 | A | 0 | 5 | 2.5 | 10 | 5 | 21 |

Plants containing MON-HT1 with any of the three operably linked CTPs (A, B, or C) had better tolerance to quizalofop-P than plants containing MON-HT1 without an operably linked CTP. Plants containing MON-HT1 with the operably linked ‘A’ CTP had 0 to 15% injury rating across all quizalofop-P applications. Plants containing MON-HTI with the operably linked ‘B’ CTP had 2.5% to 20% injury rating across all quizalofop-P applications. Plants containing MON-HT1 with the operably linked ‘C’ CTP had 0 to 20% injury rating across all quizalofop-P applications compared to plants containing MON-HTI without an operably linked CTP that had 2.5% to 37.5% injury ratings across all quizalofop-P applications.

Plants containing MON-HT2 with any of the three operably linked CTPs (A, B, or C) had better tolerance to quizalofop-P than plants containing MON-HT2 without an operably linked CTP. Plants containing MON-HT2 with the operably linked ‘A’ CTP had 0 to 15% injury rating across all quizalofop-P applications. Plants containing MON-HT2 with the operably linked ‘B’ CTP had 0 to 20% injury rating across all quizalofop-P applications. Plants containing MON-HT2 with the operably linked ‘C’ CTP had 0 to 20% injury rating across all quizalofop-P applications compared to plants containing MON-HT2 without an operably linked CTP that had 35% to 70% injury ratings across all quizalofop-P applications.

Plants containing MON-HT8 with either the operably linked ‘A’ or ‘B’ CTP had better tolerance to quizalofop-P than plants containing MON-HT8 with the operably linked ‘C’ CTP. Plants containing MON-HT8 with the operably linked ‘A’ CTP had 15% to 60% injury rating across all quizalofop-P applications. Plants containing MON-HT8 with the operably linked ‘B’ CTP had 5% to 35% injury rating across all quizalofop-P applications, compared to plants containing MON-HT8 with the operably linked ‘C’ CTP that had 45% to 85% injury rating across all quizalofop-P applications.

Plants containing MON-HTI or MON-HT2 with any of the three operably linked CTPs and plants containing MON-HT9 or MONOHT10 with the operably linked ‘A’ CTP had better tolerance to quizalofop-P than plants containing MON-HT8 with any of the three operably linked CTPs. Plants containing MON-HT9 or MON-HT10 with the operably linked ‘A’ CTP had tolerance to quizalofop-P across all applications that was comparable to plants containing MON-HT1 or MON-HT2 with any of the three operably linked CTPs. At the highest rate (16×) of quizalofop application, plants containing MON-HTI or MON-HT2 with an operably linked ‘A’ CTP had a slightly higher tolerance than plants containing MON-HTI or MON-HT2 with an operably linked ‘B’ or ‘C’ CTP.

Three herbicide treatments were used in the trait efficacy field trial for 2,4-D tolerance: (1) 2,4-D amine at 4 lb ac/acre (4×) plus 0.25% v/v NIS applied to VE-V2 followed by V4 followed by V8; (2) 2,4-D amine at 8 lb ac/acre (8×) plus 0.25% v/v NIS applied to VE-V2 followed by V4followed by V8 maize; or (3) 2,4-D amine at 16 lb ac/acre (16×) plus 0.25% v/v NIS applied to VE-V2 followed by V4 followed by V8. Plots were visually rated as above.

Table 19 shows the average injury ratings in maize after 2,4-D herbicide application at V4 (CIPV4) or V8 (CIPV8) growth stage, respectively. The injury rating for the control plants after all 2,4-D applications ranged from 80% to 96.25%. At the highest rate of 2,4-D (16×) applied through V8, the plants containing MON-HT1 or MON-HT2 operably linked to any of the three CTPs (A, B, or C) had better tolerance than plants containing MON-HT1 or MON-HT2 not operably linked to a CTP. Plants containing MON-HT1, MON-HT2, or MON-HT8 with or without an operably linked CTP had better tolerance to 2,4-D at all applications tested compared to plants containing either MON-HT9 or MON-HT10 with an operably linked ‘A’ CTP. Over the range of 2,4-D applications the relative ranking of tolerance was: plants containing MON-HT1 had better tolerance than plants containing MON-HT2 which were in turn better than plants containing MON-HT8. Consistent with the data from the quizalofop-P pressure testing trial, plants containing MON-HT1, MON-HT2, or MON-HT8 operably linked to the ‘A’ CTP showed a slight mathematical, but not statistically significant, advantage over the ‘B’ and ‘C’ transit peptide. Error was calculated using LSD (0.05).

TABLE 19

| MON-HT variant | CTP | 4X 2,4-D CIPV4 LSD (0.05) = 3.4 | 4X 2,4-D CIPV8 LSD (0.05) = 3.33 | 8X 2,4-D CIPV4 LSD (0.05) = 2.1 | 8X 2,4-D CIPV8 LSD (0.05) = 3.5 | 16X 2,4-D CIPV4 LSD (0.05) = 3.4 | 16X 2,4-D CIPV8 LSD (0.05) = 3.5 |
|---|---|---|---|---|---|---|---|
| None-Control | none | 80 | 88.75 | 82.5 | 95 | 87.5 | 96.25 |
| MON-HT1 | A | 5 | 5 | 5 | 10 | 7.5 | 15 |
| MON-HT1 | B | 5 | 5 | 5 | 10 | 10 | 15 |
| MON-HT1 | C | 5 | 5 | 5 | 10 | 10 | 17.5 |
| MON-HT1 | no CTP | 5 | 5 | 7.5 | 10 | 10 | 22.5 |
| MON-HT2 | A | 5 | 5 | 10 | 7.5 | 10 | 20 |
| MON-HT2 | B | 5 | 5 | 5 | 10 | 10 | 25 |
| MON-HT2 | C | 10 | 15 | 10 | 10 | 15 | 20 |
| MON-HT2 | no CTP | 7.5 | 7.5 | 17.5 | 42.5 | 25 | 45 |
| MON-HT8 | A | 7.5 | 5 | 10 | 12.5 | 15 | 30 |
| MON-HT8 | B | 5 | 7.5 | 10 | 27.5 | 10 | 20 |
| MON-HT8 | C | 10 | 7.5 | 10 | 17.5 | 17.5 | 25 |
| MON-HT9 | A | 17.5 | 55 | 25 | 75 | 45 | 90 |
| MON-T10 | A | 32.5 | 70 | 55 | 87.5 | 45 | 90 |

Example 6

Expression of Optimized Engineered Proteins in Soy

Two engineered proteins were selected for analysis in transgenic soybean. DNA constructs were produced for expressing MON-HT1 (SEQ ID NO:14) and MON-HT2 (SEQ ID NO:18) with codon usage optimized for dicot expression using methods known to those skilled in the art. Enhancers, promoters, leaders, introns, CTPs, and 3'UTRs in various combinations were operably linked to the engineered proteins in these DNA constructs. The DNA constructs were used to transform soybean using Agrobacterium tumifaciens and standard methods known in the art. Regenerated R0 transgenic plantlets were grown in the green house. Approximately 9 weeks after transformation at the 1-2 trifoliate leaf stage, single copy R0 events were identified and sprayed with 2,4-D herbicide at a rate of 0.5× (0.375 lb ae/acre), 2× (1.5 lb ae/acre), or 4× (3.0 lb ae/acre). Approximately 2 weeks after herbicide application, the plants were rated for herbicide injury on a scale of 1 to 3, where 1=little to no injury (<20%), 2=moderate injury (20-50%) and 3=severe injury (>50%).

R0 soy plants containing each of the constructs showed tolerance to 2,4-D with little to no injury (<20% injury) or moderate injury (20-50%). Data are provided in Table 20. This indicated that the engineered proteins MON-HT1 and MON-HT2 can confer tolerance to 2,4-D in soybean plants.

TABLE 20

| Protein | CTP | 2,4-D rate | Single copy events | Events with <20% injury | Events with 20-50% injury | Events with injury >50% |
|---|---|---|---|---|---|---|
| MON-HT1 | No | 0.5X | 130 | 120 | 10 | 0 |
| MON-HT1 | No | 2X | 36 | 6 | 30 | 0 |
| MON-HT1 | Yes | 2X | 136 | 101 | 35 | 0 |
| MON-HT2 | No | 0.5X | 22 | 3 | 19 | 0 |
| MON-HT1 | Yes | 4X | 11 | 5 | 6 | 0 |

An additional five engineered proteins optimized for activity for 2,4-D were then selected for analysis in transgenic soybean. DNA constructs were produced for expressing MON-HT13 (SEQ ID NO:47), MON-HT14 (SEQ ID NO:48), MON-HT15 (SEQ ID NO:49), MON-HT17 (SEQ ID NO:51), and MON-HT18 (SEQ ID NO:52) with codon usage optimized for dicot expression. The operably linked expression elements (promoter, leader, intron, CTP, and 3'UTR) were identical in all of the constructs. Leaf samples were taken from R0 plantlets and single copy plants were identified using a PCR-based assay. When the single-copy R0 plants had approximately two to three trifoliate leaves, they were treated with either 1.5 lb ae/acre (2×) or 3.0 lb ae/acre (4×) of 2,4-D. Seven days after herbicide application, the plants were scored for herbicide injury based on the percent area of the plant showing injury, as indicated above.

At the 2× application rate, soy plants containing any of six MON-HT variants (MON-HT1, MON-HT13, MON-HT14, MON-HT15, MON-HT17, and MON-HT18) showed excellent tolerance to 2,4-D treatment, as evidenced by all but two of the single copy plants having injury rating of <20%; these two events (one for MON-HT13 and one for MON-HT18) had an injury rating of 20-30%. At the 4× application rate, of the eleven single-copy plants containing MON-HT1, five plants had an injury score of <20%, and six plants had an injury score of 20-50%. Of the eleven single-copy plants containing MON-HT13, ten plants had an injury score of <20% and one plant had an injury score of 20-50%. Of the eight single-copy plants containing MON-HT14, six plants had an injury score of <20%, one plant had an injury score of 20-50%, and one plant had an injury score of >50%. Of the seven single-copy plants containing MON-HT15, five plants had an injury score of <20%, one plant had an injury score of 20-50%, and one plant had an injury score of >50%. Of the eleven single-copy plants containing MON-HT17, all eleven plants had an injury score of <20%. Of the twelve single-copy plants containing MON-HT18, nine plants had an injury score of <20% and three plants had an injury score of 20-50%. These results indicate that soy plants containing MON-HT1 (SEQ ID NO:14), MON-HT13 (SEQ ID NO:47), MON-HT14 (SEQ ID NO:48), MON-HT15 (SEQ ID NO:49), MON-HT17 (SEQ ID NO:51), or MON-HT18 (SEQ ID NO:52) had tolerance to 2,4-D at the 4× application rate. Furthermore, this demonstrated that soy plants containing MON-HT13 (SEQ ID NO:47), MON-HT14 (SEQ ID NO:48), MON-HT15 (SEQ ID NO:49), MON-HT17 (SEQ ID NO:51), or MON-HT18 (SEQ ID NO:52) had improved 2,4-D tolerance at the 4× application rate compared to MON-HT1 (SEQ ID NO:14). Based on the percentage of single-copy plants with an injury score of <20%, soy plants containing either MON-HT13 or MON-HT17 had better tolerance to 2,4-D applied at the 4× rate compared to soy plants containing MON-HT1, MON-HT14, MON-HT15, or MON-HT18. See Table 21.

TABLE 21

| MON-HT | SEQ ID NO | 2,4-D rate | Single copy events | Events with <20% injury | Events with 20-50% injury | Events with injury >50% |
|---|---|---|---|---|---|---|
| MON-HT1 | 14 | 2X | 12 | 12 | — | — |
| MON-HT13 | 47 | 2X | 13 | 12 | 1 | — |
| MON-HT14 | 48 | 2X | 9 | 9 | — | — |
| MON-HT15 | 49 | 2X | 5 | 5 | — | — |
| MON-HT17 | 51 | 2X | 12 | 12 | — | — |
| MON-HT18 | 52 | 2X | 12 | 11 | 1 | — |
| MON-HT1 | 14 | 4X | 11 | 5 | 6 | — |
| MON-HT13 | 47 | 4X | 11 | 10 | 1 | — |
| MON-HT14 | 48 | 4X | 8 | 6 | 1 | 1 |
| MON-HT15 | 49 | 4X | 7 | 5 | 1 | 1 |
| MON-HT17 | 51 | 4X | 11 | 11 | — | — |
| MON-HT18 | 52 | 4X | 12 | 9 | 3 | — |

Example 7

Tolerance to Synthetic Auxins Fluroxypyr, Triclopyr, and MCPA

Tolerance of maize and soy plants containing MON-HTI to applications of 2,4-D, fluroxypyr, triclopyr, and MCPA was determined. F1 hybrid maize seed for three unique events containing MON-HT1 with the 'A' CTP and R2 soy seed were planted in pots. Hybrid maize seed containing NK603×MON89034 and the same soybean germplasm used for plant transformation were used as controls. Plants were grown in a green house and four plants were used for each treatment. The plants were sprayed with herbicide in a growth chamber when the plants were between 6-8 inches (soy) and 10-12 inches (corn) tall, then transferred to a greenhouse programmed to maintain optimum growth conditions.

For soy, a 2× herbicide application rate of each of the following was used: (1) 2,4-D Amine 4 (1680 g ae/ha) (2) triclopyr (840 g ae/ha, GARLON®); (3) fluroxypyr (840 g ae/ha, Starane®); or (4) MCPA (g ae/ha 1680). Following application of triclopyr, fluroxypyr, or MCPA the primary symptomology on soy was severe necrosis and epinasty. Visual plant injury ratings were made for all treatments on a rating scale from 0% to 100%, where 0% represented plants equivalent to untreated controls and 100% represented plants that were completely dead. All ratings were taken at seven days after treatment. Plants for all three soy MON-HTI events showed good tolerance to 2,4-D Amine (2,4-D) averaging less than 7% crop injury compared to controls at 90-97% crop injury. No soybean events showed tolerance to triclopyr or fluroxypyr, with injury ratings across all three events averaged 81-97% crop injury compared to controls at 91% crop injury. One of the three soy events showed a low level of tolerance to MCPA with an average injury rating of 72% while the other two events had 90% crop injury compared to the controls at 90% injury. See Table 22.

TABLE 22

| | | | Average soy % crop injury for 4 reps | | | |
|---|---|---|---|---|---|---|
| TRT # | Herbicide | 2X Rate (g ae/ha) | MON-HT1 Event 1 | MON-HT1 Event 2 | MON-HT1 Event 3 | Control |
| 1 | 2,4-D Amine | 1680 | 4.5 | 6.5 | 5.3 | 90.0 |
| 2 | triclopyr | 840 | 81.3 | 90.0 | 90.0 | 91.3 |
| 3 | fluroxypyr | 840 | 96.3 | 93.8 | 97.5 | 91.3 |
| 4 | MCPA | 1680 | 90.0 | 90.0 | 72.5 | 90.0 |
| 5 | Controls | 0 | 0.0 | 0.0 | 0.0 | 0.0 |

For maize, a 4× herbicide application rate of each of the following was used: (1) 2,4-D Amine 4 (3360 g ae/ha); (2) triclopyr (1680 g ae/ha, GARLON®); (3) fluroxypyr (1680 g ae/ha, Starane®); or (4) MCPA (g ae/ha 3360). Following application of triclopyr, fluroxypyr, or MCPA to maize, the primary symptomology was lodging. Plants for all three maize MON-HT1 events were tolerant of 2,4-D averaging less than 15% injury compared to controls at 43% crop injury. The three MON-HT1 maize events appeared to show some low level tolerance to triclopyr with crop injury averaging 26%-37% compared to controls with 47% crop injury. The three MON-HT1 maize events appeared to show some low level tolerance to fluroxypyr with crop injury averaging 20%-21% compared to controls with 55% crop injury. Two of the MON-HT1 maize events showed good tolerance to MCPA with an average crop injury of less than 6% compared to controls at 31% crop injury. The third maize MON-HTlevent had an average injury rating of 20%. See Table 23. These results of low tolerance to triclopyr and fluroxypyr and good tolerance to MCPA were consistent with the in vitro enzymatic data with purified MON-HT1 enzyme.

TABLE 23

| | | | Average maize % crop injury for 4 reps | | | |
|---|---|---|---|---|---|---|
| # TRT | Herbicide | 4X Rate (g ae/ha) | MON-HT1 Event 1 | MON-HT1 Event 2 | MON-HT1 Event 3 | LH244 |
| 1 | 2,4-D Amine | 3360 | 5.8 | 15.0 | 5.3 | 43.8 |
| 2 | triclopyr | 1680 | 26.3 | 37.5 | 35.0 | 47.5 |
| 3 | fluroxypyr | 1680 | 20.0 | 20.0 | 21.3 | 55.0 |
| 4 | MCPA | 3360 | 3.8 | 5.0 | 20.0 | 31.3 |
| 5 | Controls | 0 | 0.0 | 0.0 | 0.0 | 0.0 |

What is claimed is:

1. A soybean plant, seed, plant tissue, plant part, or cell comprising a recombinant DNA molecule comprising a nucleic acid sequence encoding a polypeptide having at least 92% identity to the amino acid sequence of SEQ ID NO: 51.

2. The soybean plant, seed, plant tissue, plant part, or cell of claim 1, wherein the plant, seed, plant tissue, plant part, or cell comprises tolerance to at least one herbicide selected from the group consisting of AOPP herbicides, phenoxy acid herbicides, and pyridinyloxy acid herbicides.

3. The soybean plant, seed, plant tissue, plant part, or cell of claim 1, wherein the nucleic acid sequence comprises SEQ ID NO: 58.

4. A soybean plant, seed, plant tissue, plant part, or cell comprising a polypeptide having at least 92% identity to the amino acid sequence of SEQ ID NO: 51.

5. The soybean plant, seed, plant tissue, plant part, or cell of claim 1, wherein the polypeptide comprises the amino acid sequence of SEQ ID NO:51.

6. The soybean plant, seed, plant tissue, plant part, or cell of claim 4, wherein the polypeptide comprises the amino acid sequence of SEQ ID NO:51.

* * * * *